United States Patent [19]

Wagnon et al.

[11] Patent Number: 5,397,801
[45] Date of Patent: Mar. 14, 1995

[54] N-SULFONYLINDOLINE DERIVATIVES, THEIR PREPARATION AND THE PHARMACEUTICAL COMPOSITIONS IN WHICH THEY ARE PRESENT

[75] Inventors: Jean Wagnon, Montpellier; Paul de Cointet, Toulouse; Dino Nisato; Claude Plouzane, both of Saint Georges D'Orques; Claudine Serradeil-Legal, Escalquens; Bernard Tonnerre, Vailhauques, all of France

[73] Assignee: Sanofi, Paris, France

[21] Appl. No.: 240,360

[22] Filed: May 10, 1994

Related U.S. Application Data

[60] Division of Ser. No. 923,839, Aug. 3, 1992, Pat. No. 5,338,755, which is a continuation-in-part of Ser. No. 737,655, Jul. 30, 1991, abandoned.

[30] Foreign Application Priority Data

Jul. 31, 1990 [FR]  France ................. 90 09778
Aug. 2, 1991 [FR]  France ................. 91 09908

[51] Int. Cl.⁶ ............... A61K 31/40; C07D 209/10; C07D 413/06; C07D 417/06
[52] U.S. Cl. .................. 514/418; 514/414; 514/369; 548/483; 548/484; 548/485; 548/490; 548/491; 548/181; 548/182; 548/183; 548/468; 544/62; 544/255; 544/144; 544/373; 544/228.2; 544/235.2; 546/201; 546/273; 540/597
[58] Field of Search ............... 548/483, 484, 485, 490, 548/491, 181, 182, 183, 468; 514/414, 418, 369; 544/62, 144, 228.2, 235.2, 255; 540/597

[56] References Cited

U.S. PATENT DOCUMENTS 3,838,167  9/1974  Jones ..................... 548/491
4,479,963  10/1984  Gruenfeld ............... 548/49

FOREIGN PATENT DOCUMENTS 0469984  2/1992  European Pat. Off. ......... 548/491

OTHER PUBLICATIONS

CA 116:214341z Preparation . . . Ligands. Wagnon et al., p. 728, 1992.
CA 119:139091z Preparation . . . Antagonists. Wagnon et al., p. 864, 1993.

*Primary Examiner*—Mary C. Lee
*Assistant Examiner*—Joseph K. McKane
*Attorney, Agent, or Firm*—Bacon & Thomas

[57] ABSTRACT

The invention relates to N-sulfonyl derivatives of formulae (I) and (I)′

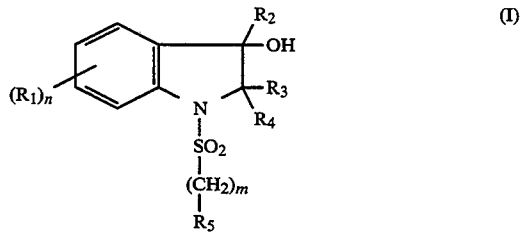

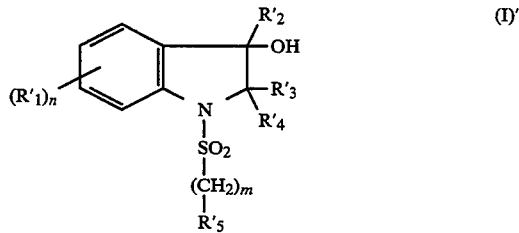

to their preparation, and to pharmaceutical compositions in which they are present. The compounds of formulae (I) and (I)′ have an affinity for the vasopressin and ocytocin receptors.

4 Claims, 6 Drawing Sheets

RMN EXAMPLE 19a

RMN EXAMPLE 20a

RMN EXAMPLE 23a

RMN EXAMPLE 24a

RMN EXAMPLE 34a

RMN EXAMPLE 32b

N-SULFONYLINDOLINE DERIVATIVES, THEIR PREPARATION AND THE PHARMACEUTICAL COMPOSITIONS IN WHICH THEY ARE PRESENT

This application is a division of application Ser. No. 07/923,839, filed Aug. 3, 1992, now U.S. Pat. No. 5,338,755, which is a continuation-in-part of application Ser. No. 07/737,655, filed Jul. 30, 1991, now abandoned.

The present invention relates to N-sulfonylindoline derivatives, to their preparation and to the compositions in which they are present.

U.S. Pat. No. 3 838 167 describes some N-sulfonylindole derivatives of the formula

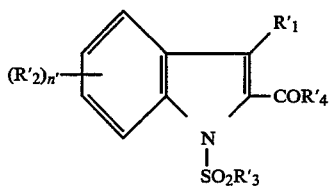

in which
- $R'_1$ is hydrogen, an alkyl or a substituted or unsubstituted phenyl;
- $R'_2$ is a halogen, an alkyl, an alkoxy, a nitro or trifluoromethyl;
- $R'_3$ is an alkyl, a phenyl or an alkylphenyl;
- $R'_4$ is an alkyl, a substituted or unsubstituted phenyl, an alkoxy or a phenoxy; and
- $n' = 0$, 1 or 2.

These compounds 1 are synthesis intermediates for the preparation of indole derivatives active on the central nervous system, said derivatives having the formula

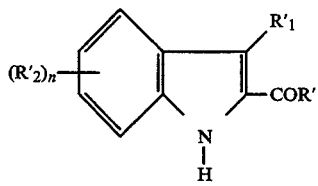

in which R' is an alkyl, a substituted or unsubstituted phenyl or a hydroxyl.

The N-sulfonylindoline derivatives according to the present invention have an affinity for the vasopressin and ocytocin receptors.

Vasopressin is a hormone known for its antidiuretic effect and its effect in the regulation of the arterial pressure. It stimulates several types of receptors—$V_1$, $V_2$, $V_{1a}$, $V_{1b}$—and thus exerts cardiovascular, central, hepatic, antidiuretic and aggregating effects. Vasopressin receptor antagonists can affect the regulation of the central and peripheral circulation, especially the coronary, renal and gastric circulation, as well as the metabolism of water and the release of adrenocorticotrophic hormone (ACTH). The vasopressin receptors, like the ocytocin receptors, are also found on the smooth muscle of the uterus. Ocytocin has a peptide structure similar to that of vasopressin. Its receptors are also found on the myoepithelial cells of the mammary gland and in the central nervous system (Presse Médicale, 1987, 16(10), 481–485, J. Lab. Clin. Med., 1989, 114(6), 617–632, and Pharmacol. Rev., 1991, 43(1), 73–108).

Thus the compounds according to the invention are useful especially in the treatment of complaints of the central nervous system, the cardiovascular system and the gastric sphere in humans and animals.

According to a first aspect, the present invention relates to compounds of the formula

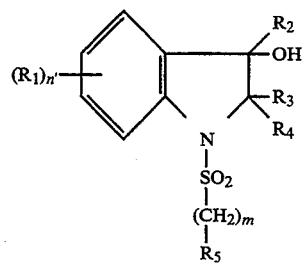

in which
- $R_1$ is a halogen atom, a $C_1$–$C_4$ alkyl, a hydroxyl, a $C_1$–$C_4$ alkoxy, a benzyloxy group, a cyano group, a trifluoromethyl group, a nitro group or an amino group;
- $R_2$ is a $C_1$–$C_6$ alkyl, a $C_3$–$C_7$ cycloalkyl, a $C_5$–$C_7$ cycloalkene or a phenyl which is unsubstituted or monosubstituted or polysubstituted by a $C_1$–$C_4$ alkyl, a $C_1$–$C_4$ alkoxy, a halogen, a trifluoromethyl group, a nitro group or an amino group;
- $R_3$ is a hydrogen atom or a $C_1$–$C_4$ alkyl;
- $R_4$ is a carboxyl group, an alkoxycarbonyl group in which the alkyl group is $C_1$–$C_6$, a benzyloxycarbonyl group or a carboxamide group of the formula $CONR_6R_7$;
- $R_5$ is a $C_1$–$C_4$ alkyl, a 1-naphthyl, a 2-naphthyl, a 5-dimethylamino-1-naphthyl or a phenyl which is unsubstituted or substituted by one or more substituents selected from a halogen atom, a $C_1$–$C_4$ alkyl, a trifluoromethyl group, a nitro group, an amino group which is free or substituted by one or 2 $C_1$–$C_4$ alkyls, a hydroxyl, a $C_1$–$C_4$ alkoxy, a $C_1$–$C_4$ alkenoxy, a $C_1$–$C_4$ alkylthio, a trifluoromethoxy group, a benzyloxy group, a cyano group, a carboxyl group, a $C_1$–$C_4$ alkoxycarbonyl group, a carbamoyl group or a $C_1$–$C_4$ alkylamido group, or, when $m=0$, $R_5$ can be a group

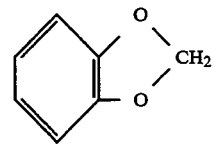

$R_6$ and $R_7$ are each independently hydrogen, a $C_1$–$C_6$ alkyl or a phenylalkyl in which the alkyl is $C_1$–$C_4$, or $R_6$ and $R_7$ together form a group $—(CH_2)_p—$;
n is 0, 1 or 2;
m is 0, 1 or 2; and
p is 4, 5 or 6;
and their salts, where appropriate.

The compounds (I) exhibit cis-trans isomerism around the 2,3 bond of the indoline. The different isomers form an integral part of the invention.

By convention, the compounds (I) in which $R_2$ and $R_4$ are on the same side of the ring are called the cis isomers.

By convention, the compounds (I) in which $R_2$ and $R_4$ are on opposite sides of the ring are called the trans isomers.

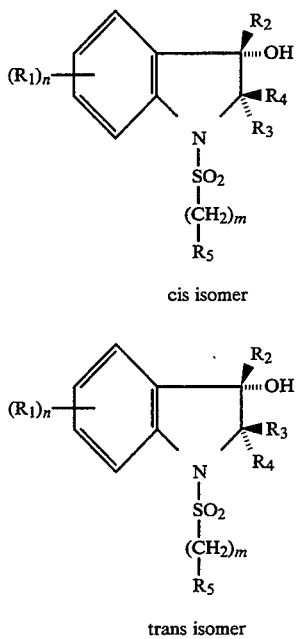

cis isomer trans isomer

Moreover, the compounds according to the invention have 2 asymmetric carbon atoms. The optical isomers of the compounds (I) form part of the invention.

In the present description and in the claims which follow, halogen is understood as meaning a fluorine, chlorine, bromine or iodine atom; alkyl group is understood as meaning linear or branched hydrocarbon groups.

Preferred compounds (I) according to the invention are those in which at least one of the following conditions is satisfied:

$R_1$ is a chlorine or bromine atom or a methoxy group and n=0;

$R_2$ is a chlorophenyl, a methoxyphenyl or a cyclohexyl;

$R_3$ is hydrogen;

$R_4$ is an alkoxycarbonyl in which the alkyl group is $C_1$-$C_6$, or $R_4$ is a carboxamide group $NR_6R_7$ in which $R_6$ and $R_7$ are $C_1$-$C_6$ alkyls;

$R_5$ is a phenyl substituted in the 3 and 4 positions or in the 2 and 4 positions by a methoxy group, or $R_5$ is a phenyl substituted in the 4 position by a methyl group; and m is 0.

The compounds (I) which are in the form of the cis isomers are particularly preferred.

BRIEF DESCRIPTION OF THE DRAWINGS

FIG. 1 is the nuclear magnetic resonance spectrum of the compound of Example 19a.

FIG. 2 is the nuclear magnetic resonance spectrum of the compound of Example 20a.

FIG. 3 is the nuclear magnetic resonance spectrum of the compound of Example 23a.

FIG. 4 is the nuclear magnetic resonance spectrum of the compound of Example 24a.

FIG. 5 is the nuclear magnetic resonance spectrum of the compound of Example 34a.

Figure 1:
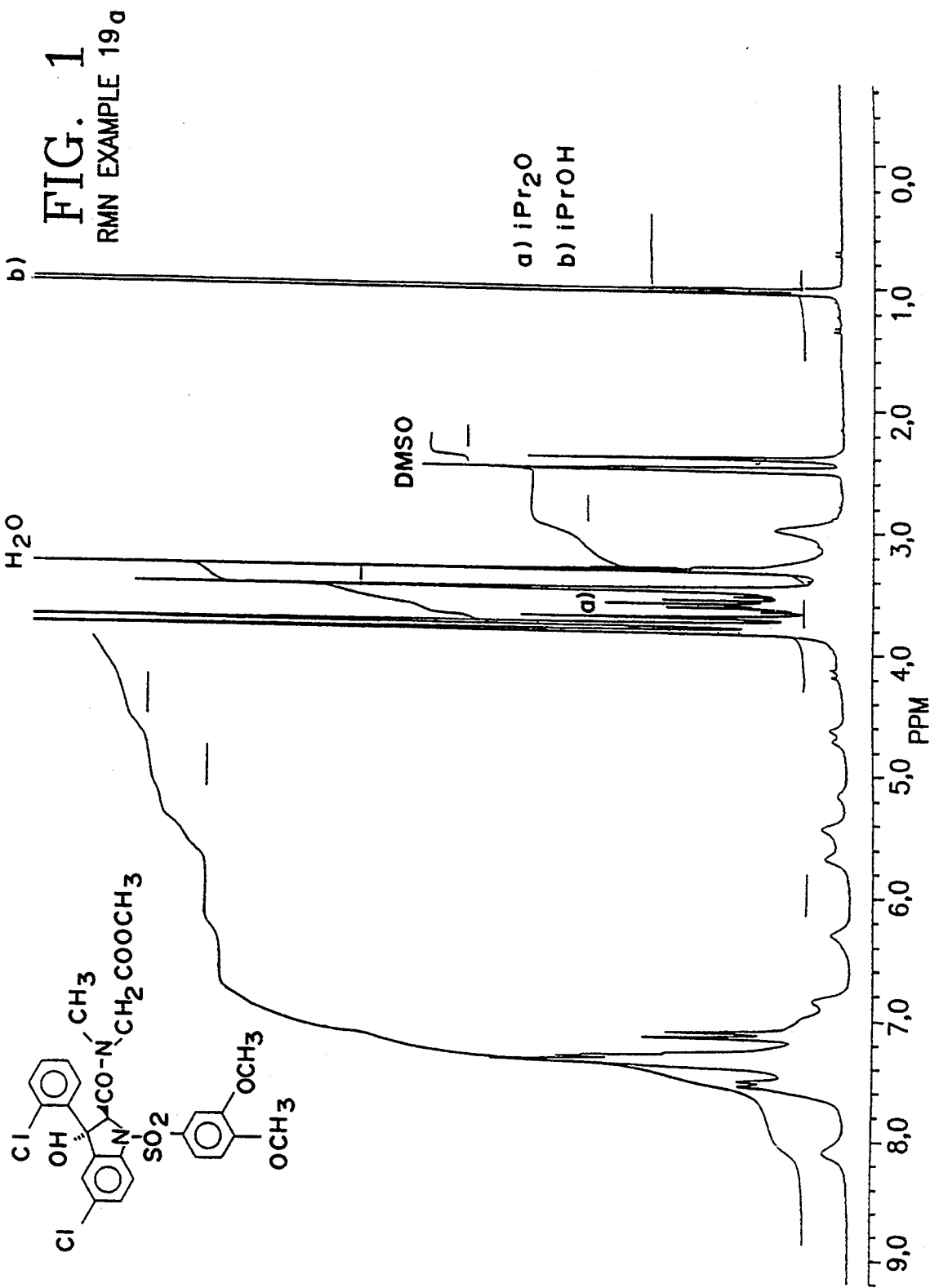

DETAILED DESCRIPTION OF THE PREFERRED EMBODIMENTS-.

The following abbreviations are used in the description and the Examples:

DCM: dichloromethane
AcOEt: ethyl acetate
MeOH: methanol
EtOH: ethanol
Ether: ethyl ether
DMF: dimethylformamide
THF: tetrahydrofuran
TEA: triethylamine
DMSO: dimethyl sulfoxide
DIPEA: diisopropylethylamine
DCC: N,N'-dicyclohexylcarbodiimide
DBU: 1,8-diazabicyclo[5.4.0]undec-7-ene
TBD: 1,5,7-triazabicyclo[4.4.0]dec-5-ene
DBN: 1,5-diazabicyclo[4.3.0]non-5-ene
DMAP: 4-dimethylaminopyridine
DMPU: 1,3-dimethyl-2-oxohexahydropyrimidinone
TMEDA: tetramethylethylenediamine
LDA: lithium diisopropylamide
HMPA: hexamethylphosphoramide
HOBT: 1-hydroxybenzotriazole hydrate
BOP: benzotriazolyloxytrisdimethylaminophosphonium hexafluorophosphate
TFA: trifluoroacetic acid
Lawesson's reagent: 2,4-bis(4-methoxyphenyl)-1,3-dithia-2,4-diphosphetane-2,4-disulfide
M.p.: melting point
Saline solution: water saturated with sodium chloride
Dry ice: solid carbon dioxide
TLC: thin layer chromatography
HPLC: high performance liquid chromatography
NMR: nuclear magnetic resonance
s: singlet
m: multipier
bs: broad singlet
d: doublet
Hydrochloric water: dilute hydrochloric acid, about 1N
80% NaH: dispersion of sodium hydride in mineral oil (Janssen Chemica)
Me: methyl
Et: ethyl
iPr: isopropyl, Pr: propyl
iPentyl: isopentyl
iBu: isobutyl
tBu:tert-butyl, Bu: butyl
Bz: benzyl
Ph: phenyl
RT: room temperature The present invention further relates to the method of preparing the compounds (I).

This method comprises a) reacting a sulfonyl derivative of the formula $$Hal-SO_2-(CH_2)_m-R_5 \qquad (III)$$

in which Hal is a halogen, preferably chlorine or bromine, and $R_5$ is as defined above for (I), with a 2-aminophenone derivative of the formula

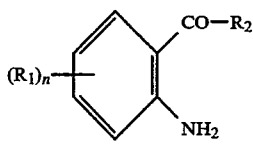 (II)

in which $R_1$, $R_2$ and n are as defined above for (I);

b) treating the resulting compound of the formula

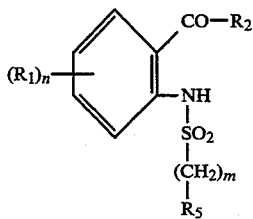 (IV)

with a halogenated derivative of the formula

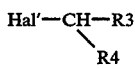 (V)

in which Hal' is a halogen, preferably bromine, and $R_3$ and $R_4$ are as defined above for (I);

c) cyclizing the resulting compound of the formula

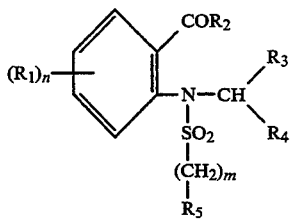 (VI)

in a basic medium in order to prepare the compound (I) according to the invention; and d) separating the cis and trans isomers of the compound (I), if appropriate.

The 2-aminophenone derivatives (II) are known or prepared by known methods such as those described by A. K. Singh et al., Synth. Commun., 1986, 16(4), 485, and G. N. Walker, J. Org. Chem., 1962, 27, 1929.

The halogenosulfonyl derivatives (III) are known or prepared by known methods. Thus, for example, 4-dimethylaminophenylsulfonyl chloride is prepared according to C. N. SUKENIK et al., J. Amer. Chem. Soc., 1977, 99, 851-858; p-benzyloxysulfonyl chloride is prepared according to European patent application 229 566.

An alkoxysulfonyl chloride is prepared from a sodium alkoxysulfonate, which is itself prepared by reacting an alkyl halide with sodium hydroxyphenylsulfonate. The 2-amino-2-trifluoromethylbenzophenones and the other trifluoromethylated derivatives are prepared according to U.S. Pat. No. 3 341 592.

2,4-Dimethoxybenzylsulfonyl chloride is prepared according to J. Am. Chem. Soc., 1952, 74, 2008.

The halogenated derivatives (V) are known or prepared by known methods such as those described by A.

I. Vogel: A Text Book of Practical Organic Chemistry: Longman, 3rd ed. 1956, p. 383, or G. Kirchner et al., J. Am. Chem. Soc., 1985, 107, 24, 7072.

Step a) of the method is carried out in pyridine by heating at a temperature between room temperature and the boiling point of the solvent for a period of time of between a few hours and a few days. If appropriate, the reaction can be carried out in the presence of dimethylaminopyridine, which is used in a catalytic or stoichiometric amount.

Step b) of the method is carried out between the sulfonamide (IV) and an excess of the halogenated derivative in a solvent such as dimethylformamide or dimethyl sulfoxide, under an inert atmosphere, at a temperature of between 0° C. and room temperature, for a time of between a few hours and 24 hours, in the presence of sodium hydride.

Step c) of the method is closely related to an aldolization reaction: The group CH—$R_3$ in the e position of the ester or the amide is deprotonated and the carbonyl group of the phenone then acts like an internal electrophile, resulting in cyclization with the appearance of two asymmetric carbons (C.).

The reaction can be illustrated by the following scheme:

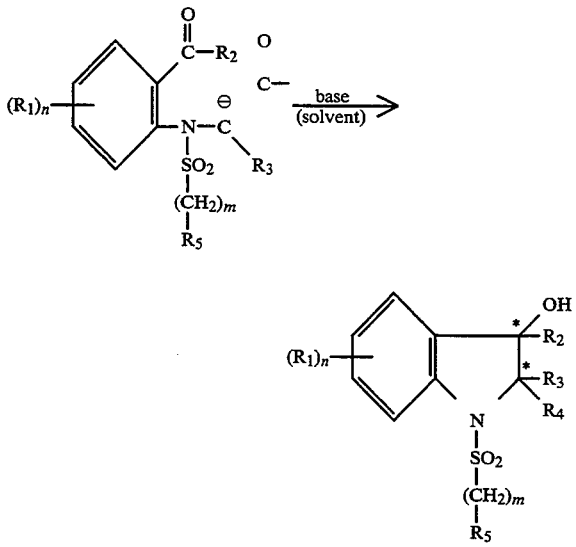

The principles of the aldol addition reaction have been reviewed by C. H. Heathcock in Asymmetric Synthesis, vol. 3: Stereodifferentiating addition reactions, part B, 111-212, Academic Press, 1984, edited by J. D. Morrison.

It is known that the aldol addition of achiral ester anions (or amide anions) on to achiral bases gives rise to the formation of 2 racemic diastereoisomers of β-hydroxyesters (or β-hydroxyamides) in a ratio which depends largely on the experimental conditions used. The following may be mentioned among these conditions: the nature of the inorganic or organic base used, the nature of the cations or counterions, the possible presence of additives in the reaction medium, the solvent, the reaction temperature and the structure of the compound undergoing this reaction.

If $R_4$ is a carboxamide group $CONR_6R_7$, in which $R_6$ and $R_7$ are as defined above for (I), it is possible to use sodium hydroxide in water, in the presence of a cosolvent, with or without the addition of a phase transfer catalyst.

This reaction can be carried out using organic bases, for example:
tertiary organic bases such as triethylamine,
guanidines such as 1,5,7-triazabicyclo[4.4.0]dec-5ene, or
amidines such as 1,8-diazabicyclo[5.4.0]undec-5-ene or 1,5-diazabicyclo[4.3.0]non-5-ene, in a solvent or a mixture of solvents selected for example from benzene, THF, dichloromethane, methanol and dimethylformamide; the reaction is carried out under an inert atmosphere at between 25° and 110° C.; the amount of base used is at least stoichiometric; the reaction can also be carried out without a solvent, at the temperature of the bath.

It is also possible to use an alcoholate of a primary, secondary or tertiary alcohol with lithium, sodium, potassium, calcium or magnesium.

The alcoholate is used in a catalytic or stoichiometric amount in an anhydrous solvent, for example an alcohol (if appropriate in the presence of a cosolvent such as THF), or else in a stoichiometric amount in THF, DMF or DMSO, if appropriate in the presence of crown ethers, for example dicyclohexyl-18 crown-6; the reaction is carried out at between 0° and 80° C. It is also possible to use a base such as sodium hydride, lithium hydride or potassium hydride, in a solvent such as, for example, ethyl ether, THF, benzene or DMF, or else alkali metal amides in a solvent such as aqueous ammonia, ether or toluene, at a temperature of between −30° C. and 110° C.

The use of an amide of the type RR'NLi or RR'NMgBr, in which R and R' are monovalent radicals, as a deprotonating agent is a method of forming enolates of esters or amides, which are intermediates in the aldolization reaction; this method has recently been reviewed by R. E. Ireland et al., J. Org. Chem., 1991, 56, 650. The reaction solvent can be benzene, hexane or THF used in anhydrous form under an inert atmosphere. Adjuvants such as LiF, LiCl, LiBr, LiI, LiBu, TMEDA, DMPU, HMPA or a crown ether can be added (M. Murakate et al., J. Chem. Soc. Chem. Commun., 1990, 1657). The influence of the reaction conditions on the proportion of each of the isomers formed has been studied. By way of example, there may be mentioned the use of lithium diisopropylamide at −78° C. in anhydrous THF under an inert atmosphere, or in THF in the presence of additives such as, for example, tetramethylenediamine, DMPU or HMPA. Examples of other known amides which can be used are lithium cyclohexylamide and lithium 2,2,6,6-tetramethylcyclohexylamide. It is also possible to prepare other amides by reacting the requisite amount of butyllithium in hexane with linear or cyclic secondary amines, the reaction taking place in one of the solvents mentioned above. Finally, various publications describe amides of optically active secondary amines: L. Duhamel et al., Bull. Soc. Chim. France, 1984, II, 421; J. K. Whitesell et al., J. Org. Chem., 1980, 45, 755; M. Murakata et al., J. Chem. Soc. Chem. Comm., 1990, 1657; M. Yamaguchi, Tetrahedron Lett., 1986, 27(8), 959; P. J. Cox and N. S. Simpkins, Tetrahedron: Asymmetry, 1991, 2(1), 1.

The silylamides of lithium, sodium or potassium constitute another group of bases which can be used, among which there may be mentioned (Me₃Si)₂NLi, (Me₂PhSi)₂NLi, (Et₃Li)₂NLi, (Me₃Si)₂NK and (Me₃Si)₂NNa.

It is also possible to use mixed amides such as those described by Y. Yamamoto, Tetrahedron, 1990, 46, 4563, for example the lithium salt of N-(trimethylsilyl)-benzylamine or an analog in which the benzylamine is replaced with a chiral primary amine such as (R)- or (S)-α-methylbenzylamine.

When chiral amides are used, the 2 diastereoisomers, cis and trans, can together or independently of one another exhibit an optical activity created by asymmetric induction and enantiomeric enrichment. The proportion of each of the enantiomers is then determined on a chiral HPLC column.

In step d), the 2 isomers of the compound (I) formed are extracted by the conventional methods and separated by chromatography or fractional crystallization.

If appropriate, the optical isomers of each of the cis and trans isomers are separated, for example by preparative chromatography on a chiral column.

If the 2 isomers of the compounds (I) are difficult to separate by the customary methods, it is also possible to prepare a compound of the formula

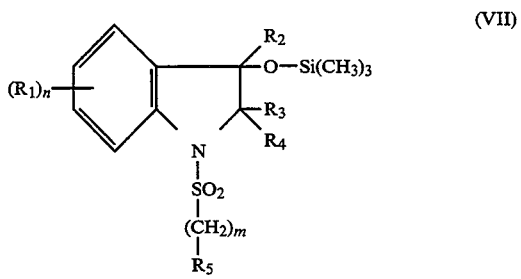

(VII)

in which R₁, R₂, R₃, R₄, R₅, m and n are as defined above for (I), by reacting hexamethyldisilazane with the corresponding compound (I). The reaction is carried out in the presence of a catalytic amount of imidazole by heating to 60°–120° C. under an inert atmosphere. The silyl ester is obtained by crystallization from the medium or after chromatography. The 2 isomers of (VII) are separated by chromatography on silica and each isomer of (VII) is then hydrolyzed in an alkaline medium to give each isomer of (I).

Several methods can be used to differentiate and characterize the cis isomer and the trans isomer of a compound (I). If R₃ is hydrogen, a comparative analysis is performed by high field NMR (at 250 MHz) coupled for example with a study of the Overhauser effect (NOE) between, for example, the proton of the indoline (R₃=H) and the proton of the hydroxyl.

If R₄ is a carboxamide group, the IR spectra of the cis isomer and the trans isomer in solution in DCM are different. The cis isomer most commonly has a strong, fine and symmetrical absorption band at around 3550–3520 cm⁻¹, due to the hydroxyl vibration, whereas the trans isomer has no resolved vibration band in this region.

By means of the data collected, it has been found that the cis isomer is generally the more mobile in TLC on an aluminum oxide plate (60F254 neutral, type E, Merck), the eluent being DCM containing variable proportions of AcOEt. Similarly, in chromatography on an alumina column (aluminum oxide 90, particle size 0.063–0,200 mm), the cis isomer is most commonly eluted first, the eluent being DCM containing variable proportions of AcOEt or MeOH.

If $R_4$ is an ester group, it is possible to carry out the TLC on a silica plate (Kieselgel 60F250, Merck) using DCM as the eluent; when the TLC is carried out on a mixture of the isomers, the cis isomer is generally the more mobile.

Thus the cis or trans isomerism of a compound (I) according to the invention can most often be determined by an analytical method. It is also possible to utilize the analogy between similar compounds or between compounds prepared from one another.

The compounds (I) in which $R_4$ is a carboxyl group are prepared by debenzylation of the compounds (I) in which $R_4$ is a benzyloxycarbonyl group by means of catalytic hydrogenation, for example in the presence of palladium-on-charcoal.

The compounds (I) in which $R_4$ is a carboxamide group, $CONH_2$, can be prepared from the corresponding compounds (I) in which $R_4$ is a carboxyl group, for example by a conventional coupling method used in peptide synthesis, for example in the presence of BOP and DIPEA.

A compound (I) in which $R_1$ is an amino group and/or a compound in which $R_5$ is a phenyl group which is substituted by an amino can be prepared by the conversion of a compound (VI), obtained in step b), in which $R_1$ is a nitro group and/or $R_5$ is a phenyl group substituted by a nitro, the other substituents having the meanings desired for (I), by means of catalytic hydrogenation, for example in the presence of palladium-on-charcoal or rhodium-on-alumina.

The compounds of formula (VI) obtained at the end of step b) are novel and form part of the invention.

According to a second aspect, the present invention relates to compounds of the formula

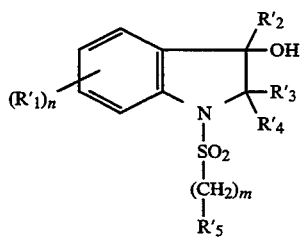

(I)′ in which
- $R'_1$ is a halogen atom, a $C_1$–$C_4$ alkyl, a hydroxyl, a $C_1$–$C_4$ alkoxy, a benzyloxygroup, a cyano group, a trifluoromethyl group, a nitro group or an amino group;
- $R'_2$ is a $C_1$–$C_6$ alkyl, a $C_3$–$C_7$ cycloalkyl, a $C_5$–$C_7$ cycloalkene or a phenyl which is unsubstituted or monosubstituted or polysubstituted by a $C_1$–$C_4$ alkyl, a $C_1$–$C_4$ alkoxy, a halogen, a trifluoromethyl group or an amino group, or $R'_2$ is a nitrophenyl which is unsubstituted or monosubstituted by a trifluoromethyl group or monosubstituted or polysubstituted by a $C_1$–$C_4$ alkyl or a halogen;
- $R'_3$ is a hydrogen atom;
- $R'_4$ is a carbamoyl group of formula $CONR_6RT$;
- $R'_5$ is a $C_1$–$C_4$ alkyl; a 1-naphthyl; a 2-naphthyl; a 5-dimethylamino-1-naphthyl; a phenyl which is unsubstituted or substituted by one or more substituents selected from a halogen atom, a $C_1$–$C_4$ alkyl, a trifluoromethyl group, an amino group which is free or substituted by one or 2 $C_1$–$C_4$ alkyls, a hydroxyl, a $C_1$–$C_4$ alkoxy, a $C_2$–$C_4$ alkenoxy, a $C_1$–$C_4$ alkylthio, a trifluoromethoxy group, a benzyloxy group, a cyano group, a carboxyl group, a $C_1$–$C_4$ alkoxycarbonyl group, a carbamoyl group which is free or substituted by one or two $C_1$–$C_4$ alkyls or a $C_1$–$C_4$ alkylamido group, or $R'_5$ is a nitrophenyl which is unsubstituted or monosubstituted by a trifluoromethyl group or a $C_2$–$C_4$ alkenoxy or mono- or polysubstituted by a halogen, a $C_1$–$C_4$ alkyl, a $C_1$–$C_4$ alkoxy, a $C_1$–$C_4$ alkythio, a trifluoromethoxy group or a benzyloxy group;
- $R'_6$ is a $C_1$–$C_6$ alkyl or $R'_6$ is similar to $R'_7$;
- $R'_7$ is a 4-piperidyl group or a 3-azetidinyl group, the said groups being substituted or unsubstituted on the nitrogen by a $C_1$–$C_4$ alkyl, by a benzyloxycarbonyl or by a $C_1$–$C_4$ alkoxycarbonyl; a group $(CH_2)_r$ which is itself substituted by a 2-, 3- or 4-pyridyl group, by a hydroxyl group or by an amino group which is free or substituted by one or two $C_1$–$C_4$ alkyls, a carboxyl group, a $C_1$–$C_4$ alkoxycarbonyl group, a benzyloxycarbonyl group or a carbamoyl group which is free or substituted by one or 2 $C_1$–$C_4$ alkyls;
- or $R'_6$ and $R'_7$ together, with the nitrogen atom to which they are connected, form a heterocycle selected from:
  - morpholine,
  - thiomorpholine,
  - thiazolidine or 2,2-dimethylthiazolidine, unsubstituted or substituted by $R_8$,
  - piperazine, unsubstituted or substituted at the 4-position by a group $R''_8$,
  - an unsaturated, 5-membered ring containing a single nitrogen atom and substituted by $R_8$ or a saturated, 3-, 4-, 5-, 6- or 7-membered ring containing a single nitrogen atom and substituted by $R_8$ and $R_9$;
- $R_8$ is $R'_8$ or a group $(CH_2)_r$ which is itself substituted by a hydroxyl or by an amino which is free or substituted by one or two $C_1$–$C_4$ alkyls;
- $R'_8$ is a group $(CH_2)_q$ which is itself substituted by a carboxyl group, a $C_1$–$C_4$ alkoxycarbonyl group, a benzyloxycarbonyl group, a carbamoyl group which is free or substituted by a hydroxyl or by one or 2 $C_1$–$C_4$ alkyls or an aminocarbothioyl group which is free or substituted by one or 2 $C_1$–$C_4$ alkyls;
- $R''_8$ is $R'_8$ or a group $(CH_2)_2NH_2$ which is free or substituted by one or two $C_1$–$C_4$ alkyls;
- $R_9$ is hydrogen, a halogen, a group $(CH_2)_rOR_{10}$, a group $(CH_2)_rNR_{11}R_{12}$, a group $(CH_2)_aCONR_{11}R'_{11}$ or an azido group;
- $R_{10}$ is hydrogen, a $C_1$–$C_4$ alkyl, a mesyl or a tosyl;
- $R_{11}$, $R'_{11}$ and $R_{12}$ are each a hydrogen or a $C_1$–$C_4$ alkyl or $R_{11}$ is hydrogen and $R_{12}$ is a benzyloxycarbonyl or a $C_1$–$C_4$ alkoxycarbonyl;
- n is 0, 1 or 2;
- m is 0, 1 or 2;
- q is 0, 1, 2 or 3;
- r is 0, 1, 2 or 3, with the limitation that r is not zero when $R_8$ or $R_9$ is at the alpha-position of the intracyclic amide nitrogen;
- s is 0 or 1;

as well as their possible salts.

The salts of the compounds of formula (I)′ according to the present invention comprise those with inorganic or organic acids which make possible a suitable separation or crystallization of the compounds of formula (I)′, such as picric acid, oxalic acid or an optically active acid, for example a mandelic acid or a camphosulfonic acid, and those which form pharmaceutically acceptable salts such as the hydrochloride, the hydrogensulfate, the dihydrogenphosphate, the methanesulfonate, the maleate, the fumarate or the 2-naphthalenesulfonate.

The salts of the compounds of formula (I)' also comprise the salts with organic or inorganic bases, for example the salts of alkali or alkaline-earth metals such as the salts of sodium, potassium or calcium, the salts of sodium and potassium being preferred, or with an amine, such as trometamol, or even the salts of arginine or lysine or of any pharmaceutically acceptable amine.

The compounds (I)' exhibit cis-trans isomerism around the 2,3 bond of the indoline. The different isomers form an integral part of the invention.

By convention, the compounds (I)' in which $R'_2$ and $R'_4$ are on the same side of the ring are called the cis isomers.

By convention, the compounds (I)' in which $R'_2$ and $R'_4$ are on opposite sides of the ring are called the trans isomers.

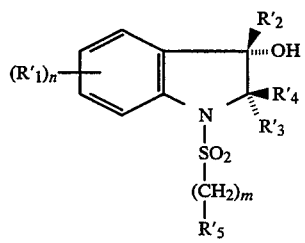

cis isomer

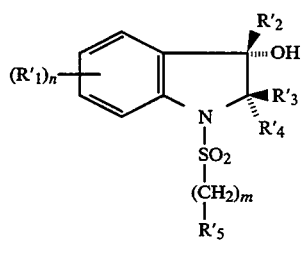

trans isomer

Moreover, the compounds according to the invention have 2 asymmetric carbon atoms or more when $R'_4$ contains one 1 or 2 asymmetric carbons. The optical isomers of the compounds (I) form part of the invention.

In the present description and in the claims which follow, halogen is understood as meaning a fluorine, chlorine, bromine or iodine atom; alkyl group is understood as meaning linear or branched hydrocarbon groups.

Preferred compounds (I)' according to the invention are those in which at least one of the following conditions is satisfied:

$R'_1$ is a chlorine or bromine atom or a methoxy group and n=0;

$R'_2$ is a chlorophenyl, a methoxyphenyl or a cyclohexyl;

$R'_4$ is a group $CONR'_6R'_7$ in which $R'_6$ and $R'_7$ or $NR'_6R'_7$ have one of the following definitions;

$NR'_6R'_7$ is a pyrrolidino group which is substituted at the 2-position by a group $(CH_2)_q$ which is itself substituted by a carboxyl or carbamoyl group with q=0, 1,2 or 3.

$NR'_6R'_7$ is a piperidino group which is substituted at the 4-position by an amino group, a $C_1$-$C_4$ alkylamino or a $C_1$-$C_4$ dialkylamino, $NR_6R_7$ is a thiazolidino group which is substituted by a group $(CH_2)_q$ which is itself substituted by a carboxyl or carbamoyl group with q =0, 1, 2 or 3.

$NR_6R_7$ is a pyrrolidino group which is substituted at the 2-position by a group $(CH_2)_q$ which is itself substituted by a carboxyl or carbamoyl group with q=0, 1, 2 or 3 and which is substituted at the 4-position by an amino group, a $C_1$-$C_4$ alkylamino or a $C_1$-$C_4$ dialkylamino;

$R'_6$ is a $C_1$-$C_4$ alkyl and $R'_7$ is a group $(CH_2)_r$ which is itself substituted by a carboxyl group or a carbamoyl group with r=1, 2 or 3;

$R'_5$ is a phenyl substituted at the 3- and 4-position or at the 2- and 4-position by a methoxy group, or $R'_5$ is a phenyl substituted at the 4-position by a methyl group;

m=0.

The compounds (I)' which are in the form of the cis isomers are particularly preferred.

The present invention further relates to the process for preparing the compounds (I)'.

This process comprises a) reacting a 2-aminophenone derivative of formula:

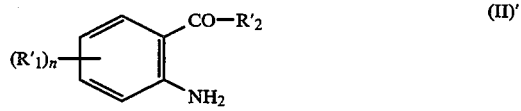

in which $R'_1$, $R'_2$ and n have the meanings indicated above for I, with a sulfonyl derivative of formula:

in which

Hal is a halogen, preferably chlorine or bromine, m and $R'_5$ have the meanings indicated above for (I)';

b) treating the resulting compound of formula:

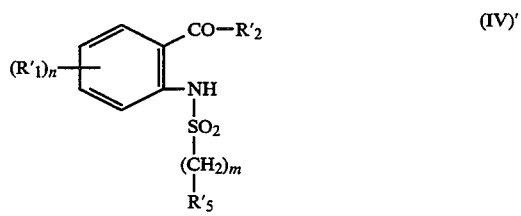

with a halogenated derivative of formula:

in which

Hal' is a halogen, preferably bromine, and A represents either the group $NR_6R_7$ or the group OR in which R is a tert-butyl or a benzyl;

c) deprotecting the resulting ester of formula:

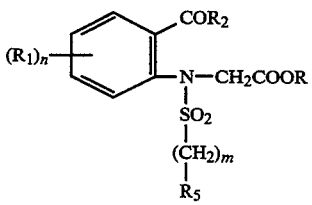

(VIa)

under suitable conditions, if applicable, when A is OR;

d) treating, if applicable, the resulting acid from Step c) of formula:

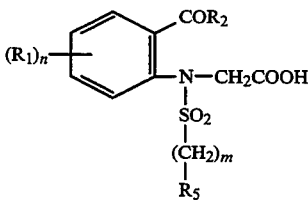

(VIb)

or its acid chloride of formula:

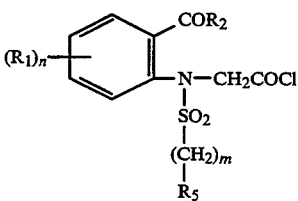

(VIc)

with a compound $HNR'_6R'_7$ according to suitable amide coupling techniques;

e) cyclizing the resulting compound from Step b) or from Step d) of formula:

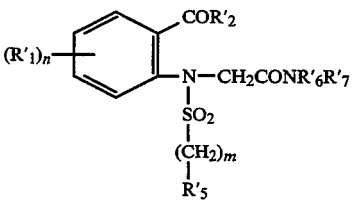

(VI)' in a basic medium in order to prepare the compound (I) according to the invention;

f) separating, if appropriate, the cis and trans isomers of the compound (I)' and, if appropriate, separating the enantiomers.

The 2-aminophenone derivatives (II)' are known or prepared by known methods such as those described by A. K. Singh et al., Synth. Commun. 1986, 16 (4), 485 and G. N. Walkerr J. Org. Chem., 1962, 27, 1929. The 2-amino-2'-trifluoromethylbenzophenonea and the other trifluoromethylated derivatives are prepared according to U.S. Pat. No. 3,341,592.

2,4-dimethoxybenzenesulfonyl chloride is prepared according to J. Am. Chem. Soc., 1952, 74, 2008.

The sulfonyl derivatives of formula (III)' are known or prepared by known methods. Thus, for example, 4-dimethylaminobenzenesulfonyl chloride is prepared according to C. N. Sukenik et el., J. Am. Chem. Soc., 1977, 99, 851–858; p-benzyloxybenzenesulfonyl chloride is prepared according to European patent application EP 229,566.

The alkoxybenzenesulfonyl chloride is prepared from the sodium alkoxybenzenesulfonate, which is itself prepared by reacting an alkyl halide with sodium hydroxybenzenesulfonate.

The halogenated derivatives of formula (V)' are known or prepared by known methods, such as those described by A. I. Vogel: A Text Book of Practical Organic Chemistry: Longman, 3rd ed. 1956, p. 383, or G. Kirchner et el., J. Am. Chem. Soc., 1985, 107, 24, 7072.

Step a) of the process is carried out in pyridine by heating at a temperature between room temperature and the boiling point of the solvent for a period of time of between a few hours and a few days. If appropriate, the reaction can be carried out in the presence of dimethylaminopyridine, which is used in a catalytic or stoichiometric amount.

Step b) of the process is carried out between the sulfonamide of formula (IV)' and an excess of the halogenated derivative of formula (V)', in a solvent such as dimethylformamide or dimethyl sulfoxide, under an inert atmosphere, at a temperature of between 0° C. and room temperature, for a time of between a few hours and 24 hours, in the presence of sodium hydride.

When the group $-N'_6R'_7$ contains a second amine group, that is to say when $R'_6$ and/or $R'_7$ are substituted by an amino group, it is possible to choose to use a halogenated derivative (V)' of formula tHal'—CH$_2$—CO$_2$R in which R is a tert-butyl or a benzyl, in order to prepare the intermediates of formula (VIa) and then (VIb). In this case, Step c) for the formation of the acid of formula (VIb) is carried out either by the action of hydrogen in the presence of a catalyst such as palladium on charcoal when R is benzyl, or in acid medium, when R is tert-butyl, for example in the presence of TFA or in the presence of hydrobromic acid in acetic acid or even in the presence of $ZnBr_2$ in DCM.

Step d) is then carried out under the conventional conditions for amide coupling, for example in the presence of BOP or HOBT and DCC.

The compounds $HN'_6R'_7$ are known or prepared by known methods. By way of example, the stereospecific synthesis of (R)- and (S)-2-pyrrolidinylacetic acids is carried out according to H. Rueger et al. in Heterocycles, 1982, 19 (9), 1677 from a proline derivative of suitable configuration. The preparation of methyl N-Boc-3,4-dehydro-α-prolinate is carried out according to J. R. Dormoy, Synthesis, 1982, 753. The preparation of optically pure derivatives of pipecolic acid is described, for example, in Tetrahedron, 1992, 48 (3) 431–442 and Tetrahedron, 1991, 47 (24) 4039–4062.

The preparation of the derivatives of aziridinecarboxylic acid is carried out according to K. Nakajima et al. in Bull. Chem. Soc. Jap., 1978, 51 (5), 1577.

Step e) of the process is closely related to an aldolization reaction: the methylene group in the position of the amide is deprotonated and the carbonyl group of the phenone then acts like an internal-electrophile, resulting in cyclization with the appearance of two asymmetric carbons (C*).

The reaction can be illustrated by the following scheme:

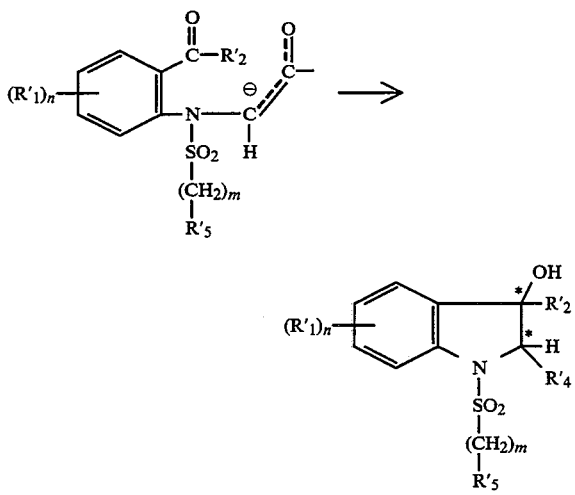

The principles of the aldol addition reaction have been reviewed by C. H. Heathcock in Asymmetric Synthesis, vol. 3: Stereodifferentiating addition reactions, part B, 111–112; Academic Press, 1984, edited by J. D. Morrison.

It is known that the aldol reaction of achiral amide anions gives rise to the formation of 2 racemic diastereoisomers of β-hydroxyamides in a ratio which depends largely on the experimental conditions used. The following may be mentioned among these conditions: the nature of the inorganic or organic base used, the nature of the cations or counterions, the possible presence of additives in the reaction medium, the solvent, the reaction temperature and the structure of the compound undergoing this reaction.

When the groups $R'_6$ and $R'_7$ do not contain a group which is hydrolysable in alkaline medium, it is possible to use sodium hydroxide in water, in the presence of a cosolvent, with or without the addition of a phase transfer catalyst; it is also possible to use a quaternary ammonium hydroxide, for example benzyltrimethylammonium hydroxide in methanol.

In order to carry out this aldolization reaction, it is also possible to use organic bases, for example:
 guanidines such as 1,5,7-triazabicyclo[4.4.0]dec-5ene,
 amidines such as 1,8-diazabicyclo[5.4.0]undec-5-ene
 or 1,5-diazabicyclo[4.3.0]non-5-ene,
in a solvent or a mixture of solvents selected for example from benzene, THF, dichloromethane, methanol and dimethylformamide; the reaction is carried out under an inert atmosphere at between −10° C. and 110° C. the amount of base used is at least stoichiometric; the reaction can also be carried out without a solvent, at the temperature of the bath.

Preferentially, Step e) of the process according to the invention is carried out in the presence of 1,8diazabicyclo[5.4.0]undec-5-ene (DBU) in a solvent such as dichloromethane or methanol, at a temperature of between −10° C. and the reflux temperature of the solvent.

It is also possible to use an alcoholate of a primary, secondary or tertiary alcohol with lithium, sodium, potassium, calcium or magnesium.

The alcoholate is used in a catalytic or stoichiometric amount in an anhydrous solvent, for example an alcohol (if appropriate in the presence of a cosolvent such as THF), or else in a stoichiometric amount in THF, DMF or DMSO, if appropriate in the presence of crown ethers, for example dicyclohexyl-18-crown-6; the reaction is carried out at between −15° C. and 80° C.

The use of an amide of the type RR'NLi or RR'NMgBr, in which R and R' are monovalent radicals, as a deprotonating agent is a method of forming enolates of amides, which are intermediates in the aldolization reaction; this method has recently been reviewed by R. E. Ireland et al., J. Org. Chem., 1991, 56, 650. The reaction solvent can be benzene, hexane or THF used in anhydrous form under an inert atmosphere. Adjuvants such as LiF, LiCl, LiBr, LiI, LiBu, TMEDA, DMPU, HMPA or a crown ether can be added. (M. Murakate et al., J. Chem. Soc. Commun., 1990, 1657). By way of example, there may be mentioned the use of lithium diisopropylamide at between −78° C. and −30° C. in anhydrous THF under an inert atmosphere or in THF in the presence of additives such as, for example, tetramethylenediamine, DMPU or HMPA. Examples of other known amides which can be used are lithium cyclohexylamide and lithium 2,2,6,6-tetramethylcyclohexylamide. It is also possible to prepare other amides by reacting the requisite amount of butyllithium in hexane with linear or cyclic secondary amines, the reaction taking place in one of the solvents mentioned above.

Finally, various publications describe amides of optically active secondary amines: L. Duhamel et al., Bull. Soc. Chim. France, 1984, II, 421; J. K. Whitesell et al., J. Org. Chem., 1980, 45,755; M. Murakata et al., J. Chem. Soc. Chem. Commun., 1990, 1657; M. Yamaguchi, Tetrahedron Lett., 1986, 27 (8), 959; P. J. Cox and N. S. Simpkins, Tetrahedron: Asymmetry, 1991, 2 (1), 1.

The silylamides of lithium, sodium or potassium constitute another group of bases which can be used, among which there may be mentioned: $(Me_3Si)_2NLi$, $(Me_2PhSi)_2NLi$, $(Et_3Si)_2NLi$, $(Me_3Si)_2NK$, $(Me_3Si)_2NNa$.

It is also possible to use mixed amides as described by Y. Yamamoto, Tetrahedron, 1990, 46, 4563, for example the lithium salt of N-(trimethylsilyl)benzylamine or an analog in which the benzylamine is replaced with a chiral primary amine such as (R)- or (S)-α-methylbenzylamine.

When the compound of formula (I)' to be prepared has 2 asymmetric carbon atoms, the use of chiral amides or alcoholates in Step e) makes possible an enantiomeric enrichment of each of the cis or trans stereoisomers. The proportion of each of the enantiomers is then determined by measurement on a chiral high performance liquid chromatography column.

When the compound of formula (I)' to be prepared has 3 or 4 asymmetric carbon atoms, the cyclization Step c) can be accompanied by a diastereoisomeric enrichment and the use of a suitable chiral base makes it possible to modify this diastereoisomeric enrichment.

In Step f), the cis and trans geometric isomers of the compound (I)' formed are extracted by conventional methods and separated by chromatography or fractional crystallization.

If appropriate, the optical isomers of each of the cis and trans isomers are separated, for example by preparative chromatography on a chiral column followed, if appropriate, by a fractional crystallization or by formation of an optically active salt in the presence of a suitably selected chiral acid or base.

Thus, when the compound according to the invention has 2 asymmetric carbon atoms, the enantiomers can be separated by chiral HPLC.

When the compound according to the invention has 3 or 4 asymmetric carbon atoms, the diastereoisomers can be separated by using chromatographic methods and fractional crystallization methods.

Several methods can be used to differentiate and characterize the cis isomer and the trans isomer of a compound (I)'. When $R'_3$ is hydrogen, a comparative analysis is performed by high field NMR (250 MHz), coupled for example with the study of the Overhauser effect (N.O.E.) between, for example, the proton of the indoline ($R_3$=H) and the proton of the hydroxyl.

The IR spectra of the cis isomer and the trans isomer in solution in DCM are different. The cis isomer most commonly has a strong, fine and symmetrical absorption band at around 3550–3520 cm$^{-1}$, due to the hydroxyl vibration, whereas the trans isomer has no resolved vibration band in this region.

By means of the data collected, it has been found that the cis isomer is generally the more mobile in TLC on an aluminum oxide plate (60F254 neutral, Type E, Merck), eluting with DCM containing variable proportions of AcOEt. Similarly, in chromatography on an alumina column (aluminum oxide 90, particle size 0.063–0.200mm), the cis isomer is most commonly eluted first, the eluent being DCM containing variable proportions of AcOEt or MeOH.

Thus the cis or trans isomerism of a compound (I)' according to the invention can most often be determined by an analytical method. It is also possible to utilize the analogy between similar compounds or between compounds prepared from one another.

The absolute configuration of some compounds according to the invention was determined by an X-ray analysis. By deduction therefrom, taking into account the value of the optical rotation, it is also possible to know the absolute configuration of other compounds obtained in an analogous fashion.

A compound (I)' in which $R'_1$ is an amino group and/or a compound in which $R'_5$ is a phenyl group which is substituted by an amino can be prepared by the conversion of a compound (VI)', obtained in Step b), in which $R'_1$ is a nitro group and/or $R_5$ is a phenyl group which is substituted by a nitro, the other substituents having the meanings desired for (I)', by catalytic hydrogenation, for example in the presence of palladium on charcoal, or rhodium on alumina or Raney nickel.

The compounds (I)' in which the substituents $R'_6$ and/or $R_7$ or the group $NR'_6R'_7$ contain a $C_1$–$C_4$ alkoxycarbonyl group make it possible to obtain, by hydrolysis of the ester, the compounds (I)' in which $R'_6$ and/or $R'_7$ or the group $NR'_6R'_7$ contain a carboxyl group, the other substituents of (I)' being unchanged. Furthermore, the compounds in which $R'_6$ and/or $R'_7$ or $NR'_6R'_7$ contain a carboxyl group make it possible to obtain, by a conventional amide coupling reaction, the compounds (I)' in which $R'_6$ and/or $R'_7$ or the group $NR'_6R'_7$ contain a carbamoyl group which is free or substituted by one or two $C_1$–$C_4$ alkyls, the other substituents being identical.

Finally, the compounds (I)' in which $R'_6$ and/or $R'_7$ or the group $NR'_6R'_7$ contain a carbamoyl group make it possible to obtain, by a Hofmann rearrangement, the compounds (I)' in which $R'_6$ and/or $R_7$ or the group $NR'_6R'_7$ contain an amino group, the other substituents being identical (J. Org. Chem., 1979, 44 (10), 1746).

Thus, according to the present invention, the process for preparing compounds (I)' in which $R'_6$ and/or $R'_7$ or the group $NR'_6R'_7$ contain an amino group which is free or substituted by one or two $C_1$–$C_4$ alkyls can have two variants:

i) Step b) of the process is carried out by treating the compound (IV)' obtained in Step a) with a halogenated derivative (V)' of formula Hal'—CH$_2$CONR'$_6$R'$_7$ in which $R'_6$ and/or $R'_7$ or the group $NR'_6R'_7$ contain a precursor group of the amine, for example a carboxyester, a carboxyl or a carbamoyl; the cyclization Step e) is then carried out and the precursor group of the amine is then converted into the amine, for example the carboxyester group of the compound (I)' thus obtained is hydrolyzed into a carboxyl group, which is then converted into a carbamoyl group and then into an amino group by the Hofmann rearrangement.

ii) Step b) is carried out by treating the compound (IV)' obtained in Step a) with an halogenated derivative (V)' of formula Hal'—CH$_2$COOR in which R is a benzyl or a tert-butyl; the ester of the compound (VIa)thus obtained is deprotected by a suitable treatment, according to Step c); a coupling is then carried out with the compound HNR'$_6$R'$_7$ in which the amino group of $R'_6$ and/or $R'_7$ is, if appropriate, protected; the compound (VI)' thus obtained is then cyclized according to Step e); and, if appropriate, the compound (I)' in which the amino group is free is prepared by deprotection of the amine.

The compounds (I)' in which the groups $R'_6$ and/or $R'_7$ or the group $NR_6R_7$ contain a benzyloxycarbonyl or alkoxycarbonyl group as substituent of an amine group make it possible to obtain the compounds (I)' in which the amine group is free, the other substituents being identical.

The compounds of formula (VI)', useful as intermediates for the preparation of compounds (I)' according to the invention, are novel and form part of the invention. Likewise, the compounds (VIa) and (VIb) are novel and form part of the invention.

The present invention thus also relates to the compounds of formula:

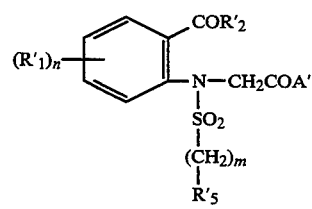

6 in which

A' is a group selected from: $NR_6R_7$, OH, OtBu, OBz;

$R'_1$ is a halogen atom, a $C_1$–$C_4$ alkyl, a hydroxyl, a $C_1$–$C_4$ alkoxy, a benzyloxy group, a cyano group, a trifluoromethyl group, a nitro group or an amino group;

$R'_2$ is a $C_1$–$C_6$ alkyl, a $C_3$–$C_7$ cycloalkyl, a $C_1$–$C_7$ cycloalkene or a phenyl which is unsubstituted or monosubstituted or polysubstituted by $C_1$–$C_4$ alkyl, a $C_1$–$C_4$ alkoxy, a halogen, a trifluoromethyl group or an amino group, or $R'_2$ is a nitrophenyl which is unsubstituted or monosubstituted by a trifluoromethyl group or monosubstituted or polysubstituted by a $C_1$–$C_4$ alkyl, a $C_1$–$C_4$ alkoxy or a halogen;

R'5 is a $C_1-C_4$ alkyl; a 1-naphthyl; a 2-naphthyl; a 5-dimethylamino-l-naphthyl; a phenyl which is unsubstituted or substituted by one or more substituents selected from a halogen atom, a $C_1-C_4$ alkyl, a trifluoromethyl group, an amino group which is free or substituted by one or 2 $C_1-C_4$ alkyls, a hydroxyl, a $C_1-C_4$ alkoxy, a $C_2-C_4$ alkenoxy, a $C_1-C_4$ alkylthio, a trifluoromethoxy group, a benzyloxy group, a cyano group, a carboxyl group, a $C_1-C_4$ alkoxycarbonyl group, a carbamoyl group which is free or substituted by one or two $C_1-C_4$ alkyls or a $C_1-C_4$ alkylamido group, or R'5 is a nitrophenyl which is unsubstituted or monosubstituted by a trifluoromethyl group or a $C_2-C_4$ alkenoxy or mono- or polysubstituted by a halogen, a $C_1-C_4$ alkyl, a $C_1-C_4$ alkoxy, a $C_1-C_4$ alkylthio, a trifluoromethoxy group or a benzyloxy group;

R'6 is a $C_1-C_6$ alkyl or R'6 is similar to R'7;

R'7 is a 4-piperidyl group or a 3-azetidinyl group, the said groups being substituted or unsubstituted on the nitrogen by a $C_1-C_4$ alkyl, by a benzyloxycarbonyl or by a $C_1-C_4$ alkoxycarbonyl; a group $(CH_2)_r$ which is itself substituted by a 2-, 3- or 4-pyridyl group, by a hydroxyl group or by an amino group which is free or substituted by one or two $C_1-C_4$ alkyls, a carboxyl group, a $C_1-C_4$ alkoxycarbonyl group, a benzyloxycarbonyl group or a carbamoyl group which is free or substituted by one or 2 $C_1-C_4$ alkyls;

or R'6 and R'7 together, with the nitrogen atom to which they are connected, form a heterocycle selected from:
morpholine,
thiomorpholine,
thiazolidine or 2,2-dimethylthiazolidine, unsubstituted or substituted by $R_8$,
piperazine, unsubstituted or substituted at the 4-position by a group R'8,
an unsaturated, 5-membered ring containing a single nitrogen atom and substituted by $R_8$ or a saturated, 3-, 4-, 5-, 6-or 7-membered ring containing a single nitrogen atom and substituted by $R_8$ and $R_9$;

$R_8$ is R'8 or a group $(CH_2)_r$ which is itself substituted by a hydroxyl or by an amino which is free or substituted by one or two $C_1-C_4$ alkyls;

R'8 is a group $(CH_2)_q$ which is itself substituted by a carboxyl group, a $C_1-C_4$ alkoxycarbonyl group, a benzyloxycarbonyl group, a carbamoyl group which is free or substituted by a hydroxyl or by one or 2 $C_1-C_4$ alkyls or an aminocarbothioyl group which is free or substituted by one or 2 $C_1-C_4$ alkyls;

R''8 is R'8 or a group $(CH_2)_2NH_2$ which is free or substituted by one or two $C_1-C_4$ alkyls;

$R_9$ is hydrogen, a halogen, a group $(CH_2)_rOR_{10}$, a group $(CH_2)_rNR_{11}R_{12}$, a group $(CH_2)_sCONR_{11}R'_{11}$ or an azido group;

$R_{10}$ is hydrogen, a $C_1-C_4$ alkyl, a mesyl or a tosyl;

$R_{11}$, R'11 and $R_{12}$ are each a hydrogen or a $C_1-C_4$ alkyl or $R_{11}$ is hydrogen and $R_{12}$ is a benzyloxycarbonyl or a $C_1-C_4$ alkoxycarbonyl;

n is 0, 1 or 2;
m is 0, 1 or 2;
q is 0, 1, 2 or 3;
r is 0, 1, 2 or 3, with the limitation that r is not zero when $R_8$ or $R_9$ is at the alpha-position of the intracyclic amide nitrogen;

s is 0 or 1;

According to another aspect of the present invention, the compounds (I)' according to the invention in which either R'7 or the group $NR_6R'_7$ contains a carboxyl group are useful for the preparation of analogous decarboxylated compounds.

According to this aspect, the invention relates to the use of the compounds of formula (Ia)

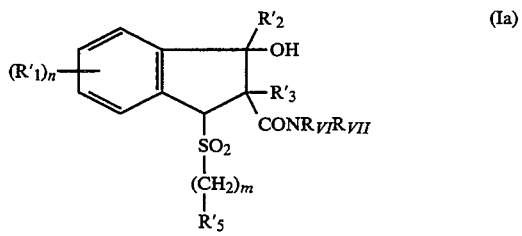

(Ia)

in which R'1, R'2, R'3, R'5, m and n have the meanings indicated above for (I),
$R_{VI}$ is a $C_1-C_6$ alkyl,
RVII is a group $(CH_2)_rCOOH$ with r=1, 2 or 3,
or $R_{VI}$ and $R_{VII}$ together, with the nitrogen atom to which they are connected, constitute a heterocycle selected from:
thiazolidine or 2,2-dimethyltniazolidine, substituted by a $(CH_2)_qCOOH$ group,
piperazine substituted at the 4-position by a $(CH_2)_qCOOH$ group,
an unsaturated, 5-membered ring containing a single nitrogen atom and substituted by a $(CH_2)_qCOOH$ group or a saturated, 3-, 4-, 5-, 6- or 7-membered ring containing a single nitrogen atom and substituted by a $(CH_2)_qCOOH$ group,
with q =0, 1, 2 or 3 for the preparation of a compound of formula (I)" having the same configuration around the 2,3 bond of the indoline as the starting material

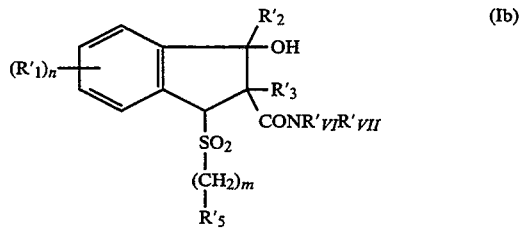

(Ib)

in which
R'1, R'2, R'3, R'5, m and n are as defined above,
R'$_{VI}$ is a $C_1-C_6$ alkyl,
R'$_{VII}$ is a group $(CH_2)_rH$,
or R'$_{VI}$ and R'$_{VII}$ together, with the nitrogen atom to which they are connected, constitute a heterocycle selected from:
thiazolidine or 2,2-dimethylthiazolidine, substituted by a $(CH_2)_qH$ group,
piperazine substituted at the 4-position by a $(CH_2)_qH$ group,
an unsaturated, 5-membered ring containing a single nitrogen atom and substituted by a $(CH_2)_qH$ group or a saturated, 3-, 4-, 5-, 6- or 7-membered ring containing a single nitrogen atom and substituted by a $(CH_2)_qH$ group.

The free-radical decarboxylation reaction is carried out according to D. H. R. Barton et al. in J. Chem. Soc; Chem. Commun.; 1984, 1298.

The affinity of the compounds according to the invention for the vasopressin receptors was determined in vitro using the method described in J. Biol. Chem., 1985, 260 (5), 2844–2851. This method consists in studying the displacement of tritiated vasopressin bound to the $V_1$ sites of rat liver membranes. The 50% inhibitory concentrations ($IC_{50}$) of the compounds according to the invention for the binding of tritiated vasopressin are low, ranging up to $10^{-9}M$.

Furthermore, the inhibition of the platelet aggregation induced by vasopressin was measured on a human platelet rich plasma (human PRP) using the method described in Thrombosis Res., 1987, 45, 7–16. The compounds according to the invention inhibit the aggregation induced by 50 to 100 nM concentrations of vasopressin with low $ID_{50}$ values (inhibitory doses) which range up to $10^{-9}M$. These results show the antagonistic activity of the compounds according to the invention towards the $V_1$ receptors.

The affinity of the compounds (I) or (I)' according to the invention for the $V_2$ receptors was measured by a method adapted from P. Crause et al., Molecular and Cellular Endocrinology, 1982, 28., 529–541.

The compounds according to the invention of cis configuration around the 2,3 bond of the indoline have a marked selectivity for the $V_1$ receptors.

The affinity of the compounds (I) or (I)' according to the invention for the ocytocin receptors was determined in vitro by the displacement of tritiated ocytocin bround to the receptors of a membrane preparation of gestating rat glands. The $IC_{50}$ values of the compounds according to the invention are low, of between $10^{-5}M$ and $10^{-8}M$.

The compounds according to the invention are active after administration by various routes, especially orally.

No sign of toxicity is observed with these compounds at the pharmacologically active doses.

Thus the compounds according to the invention can be used in the treatment or prevention of various vasopressin-dependent complaints, especially cardiovascular complaints such as hypertension, cardiac insufficiency, thrombosis or coronary vasospasm, in particular in smokers; complaints of the central nervous system, for example cerebral edemas, psychotic states, appetite disorders or memory disorders; complaints of the renal system, such as renal vasospasm or necrosis of the renal cortex; and complaints of the gastric system, for example ulcers or else the syndrome of inappropriate secretion of antidiuretic hormone (SIADH).

The compounds according to the invention can also be used as antiemetics, especially in motion sickness, and as antiproliferative agents, for example in cancer or atherosclerosis.

In woman, the compounds according to the invention can also be used for the treatment of dysmenorrhea or premature labor.

The present invention further relates to pharmaceutical compositions containing an effective dose of a compound according to the invention, or of a pharmaceutically acceptable salt, and suitable excipients. Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula I above, or their possible salts, can be administered to animals and humans in unit forms of administration, mixed with conventional pharmaceutical carriers, for the prophylaxis or treatment of the above disorders or diseases. Appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight and per day.

Each unit dose can contain from 0.5 to 1000 mg, preferably from 1 to 500 mg, of active ingredients in combination with a pharmaceutical carrier. This unit dose can be administered 1 to 5 times per day so as to administer a daily dosage of 0.5 to 5000 mg, preferably 1 to 2500 mg.

If a solid composition in the form of tablets is prepared, the main active ingredient is mixed with a pharmaceutical vehicle such as gelatin, starch, lactose, magnesium stearate, talc, gum arabic or the like. The tablets can be coated with sucrose, a cellulose derivative or other appropriate substances or they can also be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient in combination with a sweetener, which is preferably calorie-free, and methylparaben and propylparaben as antiseptics, as well as with a flavoring and an appropriate color.

Water-dispersible granules or powders can contain the active ingredient mixed with dispersants or wetting agents or with suspending agents such as polyvinylpyrrolidone, as well as with sweeteners or taste correctors.

Rectal administration is effected using suppositories which are prepared with binders melting at the rectal temperature, for example cocoa butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, if appropriate with one or more carriers or additives.

Apart from the products of formula I above or one of the pharmaceutically acceptable salts, the compositions of the present invention can contain other active principles which may be useful in the treatment of the disorders or diseases indicated above.

Thus the present invention relates to pharmaceutical compositions containing a plurality of active principles in association, one of which is a compound according to the invention.

The following examples illustrate the invention.

The compounds are characterized by their melting point (M.p.°C.) (or their boiling point B.p.) and/or their NMR spectrum recorded at 200 MHz in DMSO, and/or their optical rotation (αD) measured at 25° C. (except when otherwise indicated).

The measured value of the optical rotation is dependent on the amount of residual solvent present in the prepared product.

Except when otherwise indicated, the designation "cis isomer" or "trans isomer" signifies that the isolated compound is a mixture of enantiomers, either of cis configuration or of trans configuration.

The optical purity of the compounds is studied by high performance liquid chromatography (HPLC).

The examples 1 to 146 illustrate the preparation of compounds of formula (I).

The examples 1a to 119a illustrate the preparation of compounds of formula (I)'.

EXAMPLES 1 AND 2

Methyl 5-chloro-3-cyclohexyl-3-hydroxy-1-(naphthyl-1-sulfonyl)indoline-2-carboxylate, cis isomer, trans isomer

A)

5-Chloro-2-[(naphthyl-1-sulfonyl)amino]cyclohexylphenone

A mixture containing 3 g of 2-amino-5-chlorocyclohexylphenone and 3.2 g of naphthyl-1-sulfonyl chloride is heated in pyridine at 100° C. for 8 hours. The pyridine is evaporated off, water is added, the mixture is extracted with ethyl acetate and the extract is then filtered on silica using dichloromethane as the eluent to give 4.27 g of the expected product.

After recrystallization from a DCM/isopropyl ether mixture, m.p.=140°–142° C.

B)

5-Chloro-2-[N-(methoxycarbonylmethyl)-N-(naphthyl-1-sulfonyl)amino]cyclohexylphenone 4.27 g of the product obtained in the previous step are dissolved in 20 ml of anhydrous DMF under argon. 320 mg of 80% sodium hydride are added at 0° C., after 20 minutes 6.1 g of ethyl bromoacetate are then added over 30 minutes and the mixture is stirred for 3 hours at room temperature. After extraction, the crude product obtained is recrystallized from a DCM/isopropyl ether mixture to give 2.45 g of the expected compound.

M.p.=130°–132° C.

C) Methyl 5-chloro-3-cyclohexyl-3-hydroxy-1-(naphthyl-1-sulfonyl)indoline-2-carboxylate 2.4 g of the compound obtained in the previous step are suspended in 30 ml of methanol under a nitrogen atmosphere, 26 mg of sodium methylate are added at 0° C., after 10 minutes at room temperature a further 26 mg of sodium methylate are added and, finally, after 45 min, 1 ml of THF is added in order to achieve total dissolution. Then, after 1 hour, a precipitate is formed by the addition of dry ice and water. The precipitate is filtered off, taken up with ethyl acetate, washed with water and an aqueous solution of sodium chloride and dried. The oil obtained is chromatographed on silica, the eluents being DCM and then DCM containing up to 10% of AcOEt; the 2 isomers are separated in this way.

The compounds contained in each of the fractions are then recrystallized from a DCM/isopropyl ether mixture.

M.p.=155°–157° C.: cis isomer.

M.p.=141°–142° C.: trans isomer.

EXAMPLES 3 AND 4

Methyl 5-chloro-3-(2-fluorophenyl)-3-hydroxy-1-(4-nitrophenylsulfonyl)indoline-2-carboxylate, cis isomer, trans isomer

A)

5-Chloro-2'-fluoro-2-[(4-nitrophenylsulfonyl)amino]benzophenone

A mixture containing 24.9 g of 2-amino-5-chloro-2'-fluorobenzophenone and 22.1 g of 4-nitrophenylsulfonyl chloride is refluxed for 10 hours in pyridine. It is evaporated to dryness, water and ethyl acetate are then added and the ethyl acetate phase is washed with water and an aqueous solution of sodium chloride, dried over magnesium sulfate and evaporated under vacuum. The expected product precipitates on evaporation; it is filtered off and recrystallized from a DCM/isopropyl ether mixture to give 20 g.

M.p.=155° C.

B)

5-Chloro-2'-fluoro-2-[N-(methoxycarbonylmethyl)-N-(4-nitrophenylsulfonyl)amino]benzophenone 5 g of the compound obtained in the previous step are dissolved in 20 ml of DMF at 0° C. under argon, 367 mg of 80% sodium hydride are added, 3.5 g of methyl bromoacetate are added after 5 minutes and a further 3.5 g of methyl bromoacetate are added after 1 hour. After 5 hours at room temperature, the reaction mixture is poured into iced water and then extracted 3 times with ethyl acetate and the extract is washed 3 times with water and an aqueous solution of sodium chloride and then dried over magnesium sulfate. The product is chromatographed on silica gel using DCM as the eluent to give 6.1 g of the expected compound, which solidifies in methanol.

C)

3 g of the compound obtained in the previous step are suspended in 50 ml of methanol and cooled in an ice bath. 330 mg (0.1 equivalent) of sodium methylate are added and the mixture is stirred for 60 minutes, the temperature being allowed to rise to 10° C. Dry ice and then water are added, the mixture is extracted 3 times with ethyl acetate and the extract is then washed with water and an aqueous solution of sodium chloride, dried and evaporated under vacuum. The crude reaction product (6.1 g) is chromatographed on a silica column prepared in DCM.

The 2 isomers are eluted successively with DCM.

The less polar isomer is the cis isomer.

After recrystallization from a DCM/isopropyl ether mixture, m.p.=219°–220° C.

The more polar isomer is the trans isomer.

After recrystallization from a DCM/methanol mixture, m.p.=203°–204° C.

EXAMPLES 5 AND 6

Methyl
1-(4-aminophenylsulfonyl)-5-chloro-3-(2-fluorophenyl)-
3-hydroxyindoline-2-carboxylate, trans isomer, cis
isomer

A)

5-Chloro-2'-fluoro-2-[N-(methoxycarbonylmethyl)-
N(4-aminophenylsulfonyl)amino]benzophenone The 5-chloro-2'-fluoro-2-[N-(methoxycarbonylmethyl)-N-(4-nitrophenylsulfonyl)amino]benzophenone prepared in Example 2, step b, is dissolved in 100 ml of ethyl acetate and 5 ml of methanol and hydrogenated at ordinary pressure for 2 hours in the presence of 620 mg of 10% palladium-on-charcoal; the existence of 3 compounds (starting material, intermediate and expected product) is observed in TLC. The catalyst is filtered off, the solvent is evaporated off and the residue is chromatographed on silica gel. The expected compound is eluted with DCM containing 1% of methanol. After recrystallization from DCM/isopropyl ether, m.p.=168°–170° C.

B) Trans isomer 3.4 g of the compound obtained in the previous step are dissolved in 20 ml of methanol and 20 ml of THF at 0° C. under nitrogen and 190 mg of sodium methylate are added. After 60 minutes at 5° C., with stirring, the reaction medium is poured into water and extracted with ethyl acetate. A compound crystallizes and is recrystallized from DCM containing a small amount of methanol.

M.p.=215°–216° C.

This is the trans compound according to a study of the NMR spectrum with NOE.

C) Cis isomer 200 mg of the compound prepared in Example 3 are dissolved in 10 ml of ethyl acetate and 2 ml of methanol and hydrogenated at ordinary pressure for 3 hours in the presence of 50 mg of 10% palladium-on-charcoal. The catalyst is filtered off, the filtrate is evaporated to dryness and the residue is chromatographed on silica gel, the eluent being DCM containing 1% of methanol. The product obtained is recrystallized from MeOH/isopropyl ether to give 105 mg.

M.p.=186°–190° C.

EXAMPLES 7 AND 8

Methyl
3-(2-fluorophenyl)-3-hydroxy-5-nitro-1-tosylindoline-2-carboxylate, cis isomer, trans isomer

A) 2'-Fluoro-5-nitro-2-tosylaminobenzophenone

A mixture containing 10 g of 2-amino-5-nitro-2'-fluorobenzophenone and 7.5 g of tosyl chloride is refluxed in 50 ml of pyridine for 24 hours. The solvent is evaporated off to dryness, water and ethyl acetate are added, an insoluble material is filtered off and the organic phase is washed with a dilute solution of hydrochloric acid, water and an aqueous solution of sodium chloride and then dried over magnesium sulfate and evaporated. The residue is chromatographed on silica and the expected product is eluted with DCM.

B)

2'-Fluoro-2-[N-(methoxycarbonylmethyl)-N-(tosyl)amino]-5-nitrobenzophenone 4 g of the compound obtained in the previous step are placed in 40 ml of anhydrous DMF and treated at 0° C. with 320 mg of 80% sodium hydride and, after 10 minutes, with 6 g of methyl bromoacetate. The mixture is allowed to return to room temperature, water is added and the resulting mixture is extracted with ethyl acetate. The residue obtained after evaporation of the solvent is purified by chromatography on silica gel. The oil obtained by elution with DCM and then DCM containing up to 2% of AcOEt solidifies completely.

Elemental analysis: $C_{23}H_{19}FN_2O_7S$. calculated % C: 56.79; H: 3.94; N: 5.76. found % C: 56.54; H: 3.88; N : 5.54.

C)

A suspension containing 1.70 g of the product obtained in the previous step in 30 ml of methanol is cooled to 10° C. under argon and then treated with 100 mg of sodium methylate for 45 minutes. A large volume of water is added, the mixture is extracted with ethyl acetate and the organic phase is washed with water until the washings are neutral, washed with a saline solution, dried over magnesium sulfate and evaporated under vacuum. The residue is chromatographed on silica gel. The less polar compound is eluted with pure DCM to give 700 mg: cis isomer.

M.p.=191°–192° C. after recrystallization (DCM/isopropyl ether).

The more polar compound is eluted with a DCM/ethyl acetate mixture (95/5, v/v). 650 mg are obtained after recrystallization from DCM/isopropyl ether.

M.p.=206°–207° C.: trans isomer.

EXAMPLE 9

Methyl
5-amino-3-(2-fluorophenyl)-3-hydroxy-1-tosylindoline-
2-carboxylate, cis isomer 450 mg of the cis compound obtained in Example 4 are solubilized in 13 ml of an ethyl acetate/methanol mixture (10/3, v/v) and hydrogenated at ordinary temperature and pressure for 2 hours in the presence of 100 mg of 10% palladium-on-charcoal. The catalyst is filtered off, the solvent is evaporated off and the residue is chromatographed on silica gel using a DCM/ethyl acetate mixture (1/1, v/v) as the eluent.

A white powder is obtained after trituration in a DCM/isopropyl ether mixture.

M.p.=203° C. (cis isomer).

EXAMPLES 10 AND 11

Methyl
5-chloro-3-cyclohexyl-3-hydroxy-1-(4-methoxyphenylsulfonyl)indoline-2-carboxylate, cis isomer, trans isomer

A)

5-Chloro-1-[(4-methoxyphenylsulfonyl)amino]cyclohexylphenone

A mixture containing 20 g of 2-amino-5-chlorophenyl cyclohexyl ketone and 18 g of 4-methoxyphenylsulfonyl chloride is heated in pyridine at 100° C. overnight, the solvent is concentrated, the residue is taken up with hydrochloric water and extracted with DCM and the extract is dried and concentrated. The residue is recrystallized from an isopropyl ether/cyclohexane mixture to give 27 g of the expected compound, which crystallizes.

M.p. = 78°–80° C.

B)

5-Chloro-1-[N-(methoxycarbonylmethyl)-N-(4-methoxyphenylsulfonyl)amino]phenyl cyclohexyl ketone The compound obtained in the previous step (27 g) is treated with 2.2 g of sodium hydride in 150 ml of DMF at room temperature under argon for 30 minutes. 50 g of methyl bromoacetate are added and the mixture is left to stand overnight, with stirring. The DMF is evaporated off, the residue is taken up with water and extracted with DCM and the extract is dried and concentrated. The residue is chromatographed on silica using DCM as the eluent to give 19.5 g of the expected compound, which crystallizes from methanol.

M.p. = 115°–116° C.

C)

The product obtained in the previous step (10 g) is solubilized in 350 ml of methanol, and 0.6 g of sodium methylate in 50 ml of methanol is added. After a contact time of 5 minutes, TLC shows that the reaction is complete. The methanol is evaporated off after dry ice has been added to the medium. The residue is taken up with water and extracted with methylene chloride and the extract is chromatographed on silica using methylene chloride as the eluent.

The first fractions contain the less polar isomer, which is recrystallized from isopropyl ether.

M.p. = 100° C. (cis isomer).

This is followed by the more polar isomer.

M.p. = 145° C. (trans isomer).

EXAMPLES 12 AND 13

Methyl 5-chloro-3-hydroxy-3-pentyl-1-tosylindoline-2-carboxylate, cis isomer, trans isomer A) 4-Chloro-2-hexanoyl-N-tosylaniline A mixture containing 15 g of 4-chloro-2-hexanoylaniline and 10.5 g of tosyl chloride is heated in 100 ml of pyridine at 100° C. overnight. The solvent is evaporated off, the residue is taken up with hydrochloric water and extracted with methylene chloride and the extract is dried and concentrated. The crude reaction product crystallizes from isopropyl ether to give 14.5 g.

M.p. = 78°–80° C.

B)

4-Chloro-2-hexanoyl-N-methoxycarbonylmethyl-N-tosylaniline 14 g of the compound obtained in the previous step are treated at 0° C. under argon with 1 g of sodium hydride in DMF. After stirring for 15 minutes, 22.5 g of methyl bromoacetate are added and the mixture is stirred overnight at room temperature. After evaporation of the solvent and the excess brominated derivative with a vacuum pump, the residue is taken up with water and extracted with methylene chloride, the extract is dried and concentrated and the crude reaction product is then chromatographed on silica using a DCM/pentane mixture (50/50, v/v) as the eluent to give 12.1 g of the expected product.

M.p. = 68°–70° C.

C)

5 g of the compound obtained in the previous step are dissolved at 0° C. in 100 ml of methanol and treated with 600 mg of sodium methylate. After 10 minutes, TLC shows that the starting material has disappeared. Dry ice is added, the solvent is partially evaporated off, the residue is taken up with water and extracted with methylene chloride and the extract is dried and concentrated. The crude reaction product is chromatographed on silica using DCM as the eluent, which separates the 2 isomers. The less polar isomer is recrystallized in the cold from an ether/cyclohexane mixture to give 0.85 g.

M.p. = 95°–95° C.: cis isomer.

The more polar isomer is recrystallized from isopropyl ether to give 2 g of product.

M.p. = 102°–104° C.: trans isomer.

EXAMPLES 14 AND 15

Methyl 1-butylsulfonyl-5-chloro-3-(2-chlorophenyl)-3-hydroxyindoline-2-carboxylate, cis isomer, trans isomer A) 2-Butylsulfonamido-2′,5-dichlorobenzophenone 11 g of 2′,5-dichloroaminobenzophenone and 8.2 g of n-butanesulfonyl chloride in 40 ml of pyridine are stirred for 9 days at room temperature. The pyridine is evaporated off under vacuum, water is added, the mixture is extracted with 3 volumes of ethyl acetate and the organic phase is washed with hydrochloric water and an aqueous solution of sodium chloride and dried over magnesium sulfate. After evaporation of the solvent, the residue is chromatographed on silica gel, the expected product being eluted with a pentane/ethyl acetate mixture (90/10, v/v) to give 4.4 g.

B)

2-[N-(Butylsulfonyl)-N-(methoxycarbonylmethyl)amino]-2′,5-dichlorobenzophenone 4 g of the compound obtained in the previous step are dissolved in 40 ml of anhydrous DMF at 0° C. under argon, the solution is treated with 320 mg of 80% sodium hydride for 15 minutes, 6.5 g of ethyl bromoacetate are then added over 2 hours and the mixture is left to stand for 6 hours at room temperature. Water is added, the reaction product is then extracted and the extract is filtered on silica gel using DCM as the eluent to give the expected product in the form of a thick oil.

C)

4.3 g of the compound obtained in the previous step are placed in 50 ml of methanol at 0° C. and treated with 54 mg of sodium methylate for 3 hours. After the starting material has disappeared (as shown by TLC), the mixture is poured into a large volume of water and extracted with 3 volumes of ethyl acetate, the organic phase is washed with water and an aqueous solution of sodium chloride and dried over magnesium sulfate and the solvent is then evaporated off under vacuum. The residue is chromatographed on silica gel.

The first isomer is eluted with DCM.

M.p. = 140°–143° C.: cis isomer (recrystallization from DCM/isopropyl ether).

The second isomer (trans isomer) is eluted with a DCM/isopropyl ether mixture.

M.p. = 161°–163° C.: trans isomer (recrystallization from DCM/isopropyl ether).

EXAMPLES 16 AND 17

Methyl 5-chloro-3-(2-chlorophenyl)-1-(2,5-di-methoxyphenyl-sulfonyl)-3-hydroxyindoline-2-carboxylate, cis isomer, trans isomer A)
2',5-Dichloro-2-(2,5-dimethoxyphenylsulfonamido)benzophenone This compound is prepared by the procedure described in the previous Examples.

B)
2',5-Dichloro-2-[N-(2,5-dimethoxyphenylsulfonyl)-N(methoxycarbonylmethyl)amino]benzophenone 8.2 g of the compound prepared in the previous step are dissolved in 60 ml of anhydrous DMF at 0° C. under argon, 550 mg of 80% sodium hydride are added, after 15 minutes 8 g of methyl bromoacetate are then added and the mixture is stirred for 10 hours at room temperature. The reaction medium is poured into water and the solid formed is filtered off and then dissolved in ethyl acetate. The organic phase is washed with water and an aqueous solution of sodium chloride, dried over magnesium sulfate and evaporated under vacuum. The solid is recrystallized from a DCM/isopropyl ether mixture.
M.p.=129°-131° C.

C) Methyl 5-chloro-3-(2-chlorophenyl)-2-(2,5-dimethoxyphenyl-sulfonyl)-3-hydroxyindoline-2-carboxylate The cyclization step can be carried out in the presence of various reagents.

a) 1 g of the compound obtained in the previous step is dissolved in 10 ml of DCM at 0° C., 145 mg of DBU are added and the reaction medium is kept for 24 hours at +5° C. It is poured directly on to a silica column and eluted with DCM.

The first compound eluted (231 mg) is recrystallized from DCM/isopropyl ether.
M.p.=168°-169° C. (cis isomer).
The trans isomer is eluted next.
M.p.=193°-195° C. (recrystallization from DCM/isopropyl ether).

b) 800 mg of the compound obtained in step B are dissolved in 5 ml of anhydrous THF, 0.8 ml of HMPA is added and the mixture is cooled to −78° C. under an 10 argon atmosphere. 1 ml of a solution of the complex LDA.TFA (1.5 M) in cyclohexane is added by syringe; after 45 minutes, a further 0.3 ml of LDA is added, water is then added at −78° C. and the mixture is extracted with ethyl acetate.

NMR analysis of the product obtained shows the existence of the cis isomer (39%) and the trans isomer (61%).

c) 400 mg of the compound obtained in step B are dissolved in 3 ml of anhydrous THF under argon, the solution is cooled to −78° C. and 0.9 ml of a molar solution of LiHMDS in THF is then added, followed by 0.4 ml of HMPA in 2 ml of THF. After stirring for 60 minutes at −78° C., a further 0.3 ml of LiHMDS is added, after 10 minutes water is added at −78° C. and the mixture is then extracted with ethyl acetate.

NMR analysis of the product obtained shows the existence of the cis isomer (60%) and the trans isomer (40%).

d) 400 mg of the compound obtained in step B are dissolved in 3 ml of anhydrous THF, the solution is cooled to −78° C. under argon and 1.8 ml of a solution of KHMDS (0.5 M) in 1 ml of toluene and 0.4 ml of HMPA in 1 ml of THF are then added. The solution obtained is kept at −78° C. for 20 minutes, water is then added and the mixture is extracted with ethyl acetate.

NMR analysis of the product obtained shows the existence of the cis isomer (32%) and the trans isomer (68%).

e) 2 ml of THF and 0.4 ml of HMPA are cooled to −70° C. under argon and a molar solution of LiHMDS in 0.9 ml of THF is added; 400 mg of the compound prepared in step B in 3 ml of THF are then added dropwise.

After one hour at −70° C., water is added and the mixture is then extracted with ethyl acetate. NMR analysis of the product obtained shows the existence of the cis isomer (63%) and the trans isomer (37%).

f) 1 g of 1,3-diphenyl-1,1,3,3-tetramethyldisilazane is dissolved in 4 ml of anhydrous THF, and 2.2 ml of a 1.6 M solution of butyllithium in hexane and 1.8 ml of THF are added at −10° C. under argon.

In a parallel procedure, 400 mg of the compound prepared in step B are dissolved in 3 ml of anhydrous THF at −78° C. under argon and 2.2 ml of the solution prepared above are added over 5 minutes, followed by 0.4 ml of HMPA. After 1 hour, a further 0.5 ml of the solution prepared above is added, the mixture is then left to stand for 1 hour at −78° C. and, finally, water is added and the mixture is extracted with ether.

NMR analysis of the product obtained shows the existence of the cis isomer (57%) and the trans isomer (43%).

EXAMPLES 18, 19 AND 20

Isopentyl 5-chloro-3-cyclohexyl-3-hydroxy-1-tosylindoline-2-carboxylate, trans isomer, cis isomer, and isopentyl 5-chloro-3-cyclohexyl-3-trimethylsilyloxy-1-tosylindoline-2-carboxylate, cis isomer A) 5-Chloro-2-tosylaminophenyl cyclohexyl ketone This compound is prepared by the procedure described in the previous Examples.

B)
2-[N-(Tosyl)-N-(isopentoxycarbonylmethyl)amino]-5-chlorophenyl cyclohexyl ketone 5.7 g of the compound prepared in the previous step are dissolved in 50 ml of anhydrous DMF, 420 mg of 80% sodium hydride are added, 12 g of isopentyl bromoacetate are then added after 15 minutes and the mixture is stirred for 8 hours at room temperature. After extraction, the extract is chromatographed on silica gel and an oil is eluted with mixtures from pentane/DCM (20/80, v/v) to pure DCM.

C) Isopentyl 5-chloro-3-cyclohexyl-3-hydroxy-1-tosyl-indoline-2-carboxylate, trans isomer 1.6 g of the compound obtained in the previous step are dissolved in 10 ml of anhydrous 3-methylbutanol. The solution is cooled to 0° C., 7 mg of sodium methylate are added and the mixture is then brought back to ordinary temperature over 150 minutes. Dry ice and water are added, the mixture is extracted by decantation and the extract is washed with water and an aqueous solution of sodium chloride and dried over magnesium sulfate. The solvent is evaporated off under vacuum and the residue is then chromatographed on silica gel. A mixture of 2 isomers (1.6 g) is eluted with DCM and recrystallized from a DCM/isopropyl ether mixture: SR 47275 (trans isomer).

D) Isopentyl 5-chloro-3-cyclohexyl-3-trimethylsilyloxy-1-tosylindoline-2-carboxylate, cis isomer The mother liquors from crystallization of the trans isomer (980 mg) are dissolved under argon in 8 ml of hexamethyldisilazane in the presence of 100 mg of imidazole and the mixture is heated at 120° C. The reaction is followed by TLC on silica gel using DCM as the eluent.

A product of low polarity appears after 1 hour and a second compound, which is slightly more polar than the previous one, appears after one night. The solvent is evaporated off to dryness under vacuum and the residue is chromatographed on silica gel. The less polar compound is eluted with a DCM/pentane mixture (50/50, v/v) to give 304 mg, which are recrystallized from a DCM/isopropyl ether mixture.

M.p.=118°–121° C.

E) Isopentyl 5-chloro-3-cyclohexyl-3-hydroxy-1-tosylindoline-2-carboxylate, cis isomer 2.4 mg of solid sodium hydroxide are added to a suspension of the mother liquors of the cis isomer isolated above (220 mg) in 1 ml of water and 3 ml of THF. After 3 hours, water is added, the THF is partially evaporated off and the mixture is extracted under vacuum at room temperature by the customary methods. The residue is chromatographed on silica using a DCM/pentane mixture (95/5, v/v) as the eluent. According to the NMR spectrum, 87% of the compound obtained is in the cis form.

EXAMPLE 21

Butyl 5-chloro-3-cyclohexyl-3-hydroxy-1-tosylindoline-2-carboxylate

This compound is prepared by the reaction of butyl bromoacetate with 5-chloro-2-tosylaminophenyl cyclohexyl ketone, followed by cyclization in the presence of sodium methylate in butanol.

The compound formed is the trans isomer.
M.p.=115° C.

EXAMPLES 22 AND 23

Methyl 5-chloro-3-(2-chlorophenyl)-3-hydroxy-2-methyl-1-tosylindoline-2-carboxylate, cis isomer, trans isomer A mixture containing 0.5 g of 2′,5-dichloro- 2-[N-(1-methoxycarbonylethyl)-N-(tosyl)amino]benzophenone, 0.1 g of sodium methylate and 2 ml of DMF is stirred for 20 hours at room temperature under nitrogen. It is concentrated under vacuum, the residue is taken up with water and the precipitate is filtered off and washed with water. The residue is chromatographed on silica using DCM as the eluent to give 60 mg of the cis isomer and 250 mg of the trans isomer.

EXAMPLE 24

Methyl 5-chloro-3-(2-chlorophenyl)-1-(4-cyanophenylsulfonyl)-3-hydroxyindoline-2-carboxylate, cis isomer

A) 2-[N-(4-Cyanophenylsulfonyl)amino]-2′,5-dichlorobenzophenone 10 g of 2-amino-2′,5-dichlorobenzophenone and 7.7 g of 4-cyanophenylsulfonyl chloride are heated in pyridine at 100° C. for 48 hours in the presence of 4.6 g of DMAP, the mixture is evaporated to dryness, water and ethyl acetate are added, the organic phase is washed with dilute hydrochloric water, water and an aqueous solution of sodium chloride and dried over magnesium sulfate and the solvent is evaporated off under vacuum. The precipitate formed is filtered off and then recrystallized twice from a DCM/isopropyl ether mixture to give the expected product.

M.p.=172°–173° C.

B) 2-[N-(4-Cyanophenylsulfonyl)-N-(methoxycarbonylmethyl)amino]-2′,5-dichlorobenzophenone 10 g of the compound obtained in the previous step are dissolved in 70 ml of DMF at 0° C. under argon, 740 mg of 80% sodium hydride are then added and 14 g of methyl bromoacetate are added after 15 minutes. After 24 hours, water is added, the aqueous phase is decanted, the solid obtained is extracted with AcOEt and the organic phase is washed with water and an aqueous solution of sodium chloride, dried over magnesium sulfate and evaporated under vacuum to give the expected product, which is recrystallized from DCM/isopropyl ether.

M.p.=186°–188° C.

C)

2 g of the previous compound are suspended at 0° C. in 40 ml of an MeOH/THF mixture (1/1, v/v) and treated with 100 mg of sodium methylate. After 3 hours at ordinary temperature, total dissolution is observed. The solvents are partially evaporated off under vacuum, a large amount of water is added and the mixture is extracted with ethyl acetate. The extract is washed with water and an aqueous solution of sodium chloride, dried over magnesium sulfate and evaporated under vacuum. The residue is chromatographed on silica gel. The 2 isomers are successively eluted with methylene chloride.

The less polar isomer is recrystallized from DCM/isopropyl ether.

M.p.=222°–223° C. (cis isomer).

EXAMPLES 25 AND 26

Methyl 5-chloro-3-(2-chlorophenyl)-1-(3,4-di-methoxyphenylsulfonyl)-3-hydroxyindoline-2-carboxylate, trans isomer, cis isomer

A) 2′,5-Dichloro-2-(3,4-dimethoxyphenylsulfonamido)benzophenone 5.6 g of 2-amino-2′,5-dichlorobenzophenone and 5 g of 3,4-dimethoxyphenylsulfonyl chloride are heated in pyridine overnight at 100° C. The pyridine is evaporated off to dryness, water and ethyl acetate containing a small amount of DCM are added and the mixture is extracted. After washing several times with water and drying over sodium sulfate, the extract is evaporated under vacuum and 7.7 g of the expected product are recrystallized from a DCM/AcOEt mixture.

M.p.=164° C.

B) 2',5-Dichloro-2-[N-(3,4-dimethoxyphenylsulfonyl)-N(methoxycarbonylmethyl)amino]benzophenone 7.2 g of the compound obtained in the previous step are dissolved in anhydrous DMF at 0° C. under nitrogen. 500 mg of sodium hydride are added, followed after 10 minutes by 9.5 g of ethyl bromoacetate. After 1 night, excess water is added and the precipitate obtained is filtered off. It is dissolved in DCM, the solution is dried over magnesium sulfate and the solvent is evaporated off. 7.7 g of the expected product are recrystallized from a DCM/isopropyl ether mixture.

M.p.=164° C.

C) Trans isomer

A suspension of 7 g of the product obtained in the previous step in 90 ml of methanol containing 2 ml of THF is cooled to 0° C. under nitrogen and treated with 720 mg of sodium methylate. After 2 hours at ordinary temperature, the unreacted starting material is filtered off, a large volume of water and dry ice are added and the mixture is extracted with ethyl acetate. 4 products appear in TLC. The most abundant product is recrystallized twice from a DCM/isopropyl ether mixture.

M.p.=184°-185° C.: trans isomer.

D) Cis isomer 1.3 g of the compound obtained in step B are dissolved at 0° C. in 13 ml of DCM in the presence of 180 mg of DBU. After stirring overnight, the reaction medium is poured directly on to a silica column prepared in DCM and the mixture of compounds resulting from cyclization is thus separated by elution with DCM. Chromatography is then carried out on alumina using a DCM/isopropyl ether mixture (70/30, v/v) as the eluent. The cis isomer is thus isolated.

NMR spectrum at 200 MHz in DMSO at T=370° K:

| Delta | Appearance | Integration | Assignment |
|---|---|---|---|
| 2.50 | | | DMSO |
| 3.15 | s | 3 H | $CO_2CH_3$ |
| 3.80 | s | 3 H | $OCH_3$ |
| 3.85 | s | 3 H | $OCH_3$ |
| 5.10 | s | 1 H | CH |
| 6.50 | s | 1 H | OH |
| 7.00 to 7.80 | m | 10 H | aromatic protons |

EXAMPLES 27, 28, 29 AND 30

Benzyl 5-chloro-3-(2-chlorophenyl)-3-hydroxy-1-p-tosylindoline-2-carboxylate, trans isomer, cis isomer, and 5-chloro-3-(2-chlorophenyl)-3-hydroxy-1-p-tosylindoline-2-carboxylic acid, trans isomer, cis isomer A) 2',5-Dichloro-2-[N-(tosyl)-N-(benzyloxycarbonylmethyl)amino]benzophenone 20 g of 2',5-dichloro-2-N-tosylaminobenzophenone (prepared by the customary method) and 1.6 g of sodium hydride are reacted in 100 ml of DMF. After stirring for 15 minutes, 34 g of benzyl bromoacetate are added and the mixture is left to stand overnight at room temperature. The DMF is evaporated off, the residue is taken up with water and extracted with methylene chloride, and then dried and concentrated. The crude product obtained is chromatographed on silica gel using DCM as the eluent. The 14.39 g of product obtained are recrystallized from isopropyl ether.

M.p.=99°-101° C.

B) Benzyl 5-chloro-3-(2-chlorophenyl)-3-hydroxy-1-p-tosylindoline-2-carboxylate, trans isomer 1 g of the compound obtained in the previous step is treated at −78° C. with 1.2 ml of concentrated LDA (1.5 M) in cyclohexane. After 3 hours, the mixture is taken up with water and extracted with DCM and the extract is dried and concentrated. The crude reaction product is chromatographed on silica gel using DCM as the eluent and the mixture of 2 isomers is separated. The more polar isomer is recrystallized twice from a DCM/isopropyl ether mixture to give 600 mg of trans isomer.

M.p.=168°-169° C. (recrystallization from DCM/isopropyl ether).

C) Benzyl 5-chloro-3-(2-chlorophenyl)-3-hydroxy-1-p-tosylindoline-2-carboxylate, cis isomer 2 g of the compound prepared in step A are dissolved in DCM at 0° C. and 540 mg of DBU are added. After 20 minutes at 0° C., a potassium sulfate solution and water are added, the mixture is then extracted and the extract is dried and concentrated. Chromatography on silica using DCM as the eluent gives 450 mg of the less polar product (cis isomer) and 700 mg of the more polar product (trans isomer).

The cis isomer is obtained in the form of a foam.

Elemental analysis: calculated % C: 61.27; H: 4.05; N: 2.46. found % C: 61.29; H: 4.20; N: 2.48.

D) 5-Chloro-3-(2-chlorophenyl)-3-hydroxy-1-p-tosylindoline-2-carboxylic acid, trans isomer 500 mg of the trans isomer of the compound prepared in step B are dissolved in 300 ml of ethyl acetate in the presence of 100 mg of palladium-on-charcoal. The product crystallizes after 10 min of hydrogenolysis. The palladium is filtered off and the crystals are then solubilized with hot DMF. The DMF is concentrated and the residue is taken up with a large volume of THF. The mixture is concentrated, methanol is added and the product crystallizes to give 175 mg of the expected product (trans isomer).

| | | NMR: | |
|---|---|---|---|
| Delta | Appearance | Integration | Assignment |
| 2.44 | s | 3 H | $CH_3$ (tosyl) |
| 4.87 | s | 1 H | H6 (2-chlorophenyl) |
| 6.74 | d | 1 H | H4 (indole) |
| 6.98 | s | 1 H | OH |
| 7.28–7.53 | m | 7 H | aromatic protons |
| 7.88 | d | | OH |
| | (J = 8.6 Hz) | 2 H | H2, H6 (tosyl) |

In the same way, the cis isomer of the acid is prepared by hydrogenolysis of the benzyl ester obtained in step C.

M.p.=209°–212° C.

EXAMPLE 31

5-Chloro-3-(2-chlorophenyl)-1-(3,4-dimethoxyphenyl-sulfonyl)-3-hydroxyindoline-2-carboxylic acid, cis isomer This acid is prepared by the procedure described in the previous Example via the benzyl ester of said acid. M.p.=130°–132° C.

Methyl esters of formula (I) were prepared by analogous procedures. They are described in Table 1 below.

TABLE 1

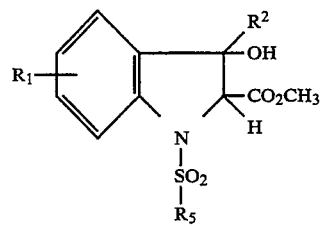
(I)

For each compound of formula (I) having the substituents $R_1$, $R_2$ and $R_5$ in the Table below, the cis isomer is indicated and then the trans isomer, unless stated otherwise.

| Example | $R_1$ | $R_2$ | $R_5$ | M.p. °C. Solvent |
|---|---|---|---|---|
| 32 | H | phenyl | p-tolyl | 154 |
| 33 | | | | 170 |
| 34 | 5-Cl | cyclopentyl | p-tolyl | 187–190 DCM/MeOH |
| 35 | | | | 153–157 DCM/isopropyl ether |
| 36 | 5-Cl | cyclohexyl | p-tolyl | 180 ether/cyclohexane |
| 37 | | | | 144 ether/cyclohexane |
| 38 | 5-Cl | cyclohexyl | 2-naphthyl | 177 MeOH |
| 39 | | | | 150 ether/cyclohexane |
| 40 | 5-Cl | isopropyl | p-tolyl | 158 DCM/isopropyl ether |
| 41 | | | | 172 DCM/isopropyl ether |
| 42 | 5-Cl | 2-F-phenyl | p-tolyl | 165–166 DCM/isopropyl ether |
| 43 | | | | 212–213 DCM/isopropyl ether |
| 44 | 5-Cl | phenyl | p-tolyl | 206 DCM/isopropyl ether/ MeOH |
| (*) 45 | | | | 193–194 AcOEt/MeOH |
| 46 | 5-Cl | cycloheptyl | p-tolyl | 170–172 isopropyl ether |
| 47 | | | | 154–155 |
| 48 | 5-Cl | 2-Cl-phenyl | p-tolyl | 174 |
| 49 | | | | 255 |
| 50 | 5-Cl | cyclohexyl | 4-dimethyl-aminophenyl | 184–185 |
| 51 | | | | 198–200 DCM/isopropyl ether |
| 52 | 5-Cl | cyclohexyl | 2,4,6-tri-methylphenyl | 139–142 DCM/isopropyl ether |
| 53 | | | | 200–203 DCM/isopropyl ether |
| 54 | 5-Cl | cyclohexyl | n-butyl | 150–153 MeOH/isopropyl ether |
| 55 | 5-Cl | 2-Cl-phenyl | 2-CF$_3$-phenyl | 216 |
| 56 | | | 2-CF$_3$-phenyl | 242 |
| 57 | 5-Cl | 2-Cl-phenyl | 4-benzyloxy-phenyl | 166 DCM/isopropyl ether |
| 58 | | | | 195 DCM/isopropyl ether |
| 59 | 5-Cl | 2-Cl-phenyl | 4-Cl-phenyl | 174 |
| 60 | | | | 230 |
| 61 | 5-Cl | 4-Cl-phenyl | p-tolyl | 224 |

TABLE 1-continued

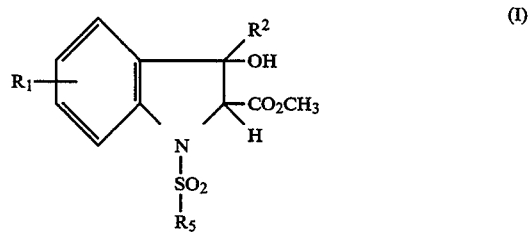

For each compound of formula (I) having the substituents $R_1$, $R_2$ and $R_5$ in the Table below, the cis isomer is indicated and then the trans isomer, unless stated otherwise.

| Example | $R_1$ | $R_2$ | $R_5$ | M.p. °C. Solvent |
|---|---|---|---|---|
| 62 | | | | 186 EtOH |
| 63 | 5-Cl | 2-CH$_3$-phenyl | p-tolyl | 168 |
| 64 | | | | 238 AcOEt |
| 65 | 5-Cl | 2-Cl-phenyl | 4-OH-phenyl | NMR (**) |
| 66 | | | | 163 MeOH/isopropyl ether |
| 67 | 5-Cl | 2-Cl-phenyl | 3-Cl-phenyl | 175 |
| 68 | | | | 186 |
| 69 | 5-Cl | 2-Cl-phenyl | m-tolyl | 173 |
| 70 | | | | 229 |
| 71 | 5-Cl | 2-methoxy-phenyl | p-tolyl | 165 |
| 72 | | | | 240 |
| 73 | 5-Cl | 3-Cl-phenyl | p-tolyl | 137 |
| 74 | | | | 210 |
| 75 | 5-Cl | 2-methyl-phenyl | 3,4-diCl-phenyl | 196 |
| 76 | | | | 175 |
| 77 cis | 5-Cl | 2-Cl-phenyl | 3-methoxy-phenyl | 132 |
| 78 | 5-Cl | 2-Cl-phenyl | 2,3,4-tri-methoxyphenyl | 207 |
| 79 | | | | 183 |
| 80 | 5-Cl | 2-Cl-phenyl | 4-butoxy-phenyl | 124–125 hexane |
| 81 | | | | 190–192 MeOH/isopropyl ether |
| 82 | 5-Cl | 2-Cl-phenyl | 4-trifluoro-methoxyphenyl | 170 |
| 83 | | | | 166 |
| 84 | 5-Br | 2-F-phenyl | 3,4-di-methoxyphenyl | 162–164 |
| 85 | | | | 162–165 DCM/isopropyl ether |
| 86 | 5-Cl | 2-Cl-phenyl | phenyl | 148 isopropyl ether |
| 87 | | | | 230 DCM/isopropyl ether |
| 88 | 5-Cl | 2-Cl-phenyl | 4-methoxy-phenyl | 173 hexane/isopropyl ether |
| 89 | | | | 217 hexane/isopropyl ether |
| 90 | 5-Br | 2-Cl-phenyl | 3,4-di-methoxyphenyl | 160–162 |
| 91 | | | | 199 |
| 92 | 5-Cl | 2-Cl-phenyl | 4-ethoxy-phenyl | 174 hexane/isopropyl ether |
| 93 | | | | 186 hexane/isopropyl ether |
| 94 trans | 2-CH$_3$O | 2-Cl | p-tolyl | 215 |
| 95 | 5-CH$_3$ | 2-Cl-phenyl | p-tolyl | 165 |
| 96 | | | | 216 EtOH |
| 97 | 5-CF$_3$ | 2-CF$_3$-phenyl | p-tolyl | 189 |
| 98 | | | | 202 |
| 99 | 5-Cl | 2-CF$_3$-phenyl | p-tolyl | 166 |

TABLE 1-continued

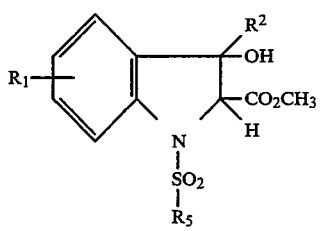

For each compound of formula (I) having the substituents $R_1$, $R_2$ and $R_5$ in the Table below, the cis isomer is indicated and then the trans isomer, unless stated otherwise.

| Example | $R_1$ | $R_2$ | $R_5$ | M.p. °C. Solvent |
|---|---|---|---|---|
| 100 | | | | 205 |
| 101 trans | 5-Cl | 2-Cl-phenyl | 3-methoxy-phenyl | 206.5 |
| 102 | 5-Cl | 2-Cl-phenyl | 4-$CF_3$-phenyl | 191 |
| 103 | | | | 180 |

(*) For this compound, the silylated derivative (VII) was prepared: cis isomer, m.p. = 176–178° C.
(**) Example 65: NMR spectrum at 200 MHz in DMSO at T = 380° K.:

| Delta | Appearance | Integration | Assignment |
|---|---|---|---|
| 2.45 | | | DMSO |
| 3.10 | s | 3 H | $CO_2CH_3$ |
| 5.00 | s | 1 H | CH |
| 6.30 | s | 1 H | OH |
| 6.80–7.80 | m | 11 H | aromatic protons |

EXAMPLES 104 AND 105

N,N-Dimethyl-5-chloro-3-cyclohexyl-3-hydroxy-1-tosylindoline-2-carboxamide, trans isomer, cis isomer A) 5-Chloro-2-tosylaminophenyl cyclohexyl ketone This compound is the one prepared in Example 18, step A.

B) Dimethylbromoacetamide

A solution containing 56 g of bromoacetyl bromide in 100 ml of DCM is cooled to 0° C. and gaseous dimethylamine is bubbled into the medium until it becomes basic. The mixture is filtered and dried and the crude amide is concentrated to give an oil (22 g).

C) 2-[N-(Tosyl)-N-(dimethylcarbamoylmethyl)amino]-5-chlorophenyl cyclohexyl ketone 4.3 g of 5-chloro-2-tosylaminophenyl cyclohexyl ketone are placed in 20 ml of DMF in the presence of mg of 80% sodium hydride, after 15 minutes at RT 5.4 g of the compound prepared in step B are added and the mixture is stirred overnight at RT. The reaction medium is poured into water and the precipitate is filtered off and then taken up with DCM, dried and concentrated. The expected product crystallizes from isopropyl ether.
m = 3.9g.
M.p. = 184°–187 ° C.

D) N,N-Dimethyl-5-chloro-3-cyclohexyl-3-hydroxy-1-tosylindoline-2-carboxamide, trans isomer 1.5 g of the compound obtained in the previous step are cooled to −78° C. in 20 ml of anhydrous THF, 2.3 ml of a 1.5 M solution of LDA in cyclohexane are added and the mixture is stirred for 2 hours at −78° C. It is poured into water and extracted with DCM and the extract is dried and concentrated. The crude product obtained is chromatographed on silica; an AcO-Et/DCM mixture (10/90, v/v) elutes a compound which is shown by NMR to be the trans isomer. It is recrystallized from an isopropyl ether/DCM mixture.
M.p. = 179°–182° C.

E) N,N-Dimethyl-5-chloro-3-cyclohexyl-3-hydroxy-1-tosylindoline-2-carboxamide, cis isomer 1.5 g of the product obtained in step C are treated with 950 mg of DBU in 10 ml of DCM for 24 hours at RT. The reaction medium is then chromatographed on silica using a DCM/AcOEt mixture (95/5, v/v) as the eluent to give the other isomer (cis isomer). It is recrystallized from isopropyl ether.
m = 120 mg.
M.p. = 152°–155° C.

EXAMPLES 106 AND 107

N,N-Dimethyl-5-chloro-3-(2-chlorophenyl)-3-hydroxy-1-tosylindoline-2-carboxamide, trans isomer, cis isomer.

A) 5,2'-Dichloro-2-tosylaminobenzophenone

This compound is prepared by the customary method.

B) 2-[N-(Tosyl)-N-(dimethylcarbamoylmethyl)amino]-5,2'-dichlorobenzophenone 8.4 g of 5,2'-dichloro-2-tosylaminobenzophenone are dissolved in 40 ml of DMF and treated with 0.7 g of 80% sodium hydride; after 15 minutes, 10 g of dimethylbromoacetamide, prepared in Example 1, are added and the mixture is stirred overnight at RT. The reaction medium is poured into water, the precipitate formed is filtered off and taken up with DCM and the solution is dried and concentrated. 9.2 g of the expected product are obtained after crystallization from isopropyl ether.
M.p. = 154°–157° C.

C)
N,N-Dimethyl-5-chloro-3-(2-chlorophenyl)-3-hydroxy-1-tosylindoline-2-carboxamide, trans isomer 1.5 g of the compound obtained in the previous step are treated at −78° C., in 100 ml of anhydrous THF, with 2.6 ml of a 1.5 M solution of LDA in cyclohexane for 3 hours. The mixture is poured into water and extracted with DCM and the extract is dried and concentrated. The residue is chromatographed on silica using a DCM/AcOEt mixture (94/6, v/v) as the eluent. A small amount of the less polar compound is collected and the more polar compound is then eluted: trans isomer.

It is recrystallized from a DCM/isopropyl ether mixture.
M.p.=232°–233° C.

D)
N,N-Dimethyl-5-chloro-3-(2-chlorophenyl)-3-hydroxy-1-tosylindoline-2-carboxamide, cis isomer 1.5 g of the compound prepared in step B are refluxed in DCM for 24 hours in the presence of 900 mg of DBU. The mixture is chromatographed on a silica column using a DCM/AcOEt mixture (95/5, v/v) as the eluent. 190 mg of the expected product are obtained after recrystallization from isopropyl ether.
M.p.=220°–221° C.

E)
The compound of step B (1.0 g) is dissolved in acetonitrile (25 ml), and 109 mg of sodium hydroxide in 2 ml of water are added. The medium is heterogeneous; it is stirred violently at 45° C. for 1 hour, using a turbine and compressed air, either in the presence of 110 mg of benzyltriethylammonium chloride or without the addition of this reagent.

After extraction, the product obtained in the form of a mixture of the 2 isomers, cis and trans, is determined. The ratio of the 2 isomers observed by NMR at 360° K in DMSO is 1/1.

EXAMPLE 108

N,N-Dimethyl-1-(4-allyloxyphenylsulfonyl)-5-chloro-3-(2-chlorophenyl)-3-hydroxyindoline-2-carboxamide, cis isomer A) Sodium 4-allyloxyphenylsulfonate 30 g of sodium phenylsulfonate are dissolved in 60 ml of ethanol and 50 ml of 15% sodium hydroxide, 20 g of allyl bromide are added and the mixture is refluxed for 48 hours. The ethanol is concentrated and the precipitate obtained is filtered off and then dried under vacuum in the presence of phosphorus pentoxide to give 23.3 g of the expected product.

B) 4-Allyloxyphenylsulfonyl chloride

The product obtained in the previous step (23.3 g) is treated overnight with 24 g of phosphorus pentachloride under reflux in 300 ml of DCM. The medium is filtered and concentrated to give an oil (16.5 g).

C)
2-[N-(4-Allyloxyphenylsulfonyl)amino]-2′,5-dichlorobenzophenone

The sulfonyl chloride obtained in the previous step is added to 19 g of 2′,5-dichloro-2-aminobenzophenone in 200 ml of pyridine. After one night at room temperature, the pyridine is concentrated, the residue is taken up with hydrochloric water and extracted with DCM and the extract is dried and concentrated. The crude product is chromatographed on silica and a DCM/pentane mixture (50/50, v/v) elutes the expected product, which is crystallized from a DCM/isopropyl ether mixture to give 8.5 g of the expected product.
M.p.=96°–97° C.

D)
2-[N-(4-Allyloxyphenylsulfonyl)-N-(N′,N′-dimethylcarbamoylmethyl)amino]-2′,5-dichlorobenzophenone 4 g of the product obtained in the previous step are dissolved in 20 ml of DMF under nitrogen, 310 mg of 80% sodium hydride are added, the mixture is stirred for 15 minutes at RT and 3.1 g of bromo-N,N-dimethylacetamide are then added. After one night at RT, the medium is poured into water, the product is filtered off and taken up with DCM, the solution is dried and concentrated and the residue is then crystallized from a DCM/isopropyl ether mixture to give 4 g of the expected product, which is finally recrystallized from the same solvent mixture.
M.p.=133°–135° C.

E)
N,N-Dimethyl-1-(4-allyloxyphenylsulfonyl)-5-chloro-3-(2-chlorophenyl)-3-hydroxyindoline-2-carboxamide, cis isomer 3.8 g of the product obtained in the previous step are treated at 30° C. with 1.8 g of DBU in 20 ml of DCM for 3 days. The medium is chromatographed on alumina and DCM elutes the less polar compound, which is recrystallized from a DCM/isopropyl ether mixture to give m=840 mg.
M.p.=181°–182° C.

EXAMPLE 109

N-Benzyl-N-methyl-5-chloro-3-(2-chlorophenyl)-3-hydroxy-1-(3,4-dimethoxyphenylsulfonyl)indoline-2-carboxamide, cis isomer A) N-Methyl-N-benzylbromoacetamide At 0° C., a solution of 10 g of bromoacetyl bromide in 20 ml of DCM is added to a solution of 6 g of methylbenzylamine and 5g of triethylamine in 50 ml of DCM. After one night at RT, ether is added, the precipitate formed is filtered off and the filtrate is concentrated to give 12 g of the expected product in crude form.

B)
2′,5-Dichloro-2-(3,4-dimethoxyphenylsulfonamido)benzophenone

This compound was prepared in Example 25, step A.

C)
2′,5-Dichloro-2-[N-(3,4-dimethoxyphenylsulfonyl)-N-(N′-methyl-N′-benzylcarbamoylmethyl)amino]benzophenone 5.5 g of the compound described in step B are dissolved in 30 ml of DMF and treated with 400 mg of sodium hydride. After 15 minutes, 12 g of the brominated derivative prepared in step A are added and the mixture is stirred at RT for 24 hours. The DMF is evaporated off, the residue is taken up with water and extracted with DCM and the extract is dried and concentrated. The crude product is chromatographed on silica and the expected product is eluted with DCM.

m=2.1g.
M.p.=148°-150° C.

D)
N-Benzyl-N-methyl-5-chloro-3-(2-chlorophenyl)-3-hydroxy-1-(3,4-dimethoxyphenylsulfonyl)indoline-2carboxamide, cis isomer The 2.1 g of product obtained in the previous step are treated with 1 g of DBU in 20 ml of DCM for 3 days. The reaction medium is poured on to an alumina column and DCM elutes the less polar isomer (870 mg) in the form of an oil. After drying, a foam is obtained which is characterized by NMR:
2.81 ppm: s: 3H: N—CH$_3$
3.60 ppm : m : 8H : 2OCH$_3$+N—CH$_2$—C$_6$H$_5$
5.35 ppm: s: 1H: CH (2-indoline)
6.20–7.80 ppm: m: 16H: aromatic protons+OH

EXAMPLES 110 AND 111

5-Chloro-3-(2-chlorophenyl)-1-(3,4-dimethoxyphenylsulfonyl)-3-hydroxy-2-pyrrolidinocarbonylindoline, cis isomer, trans isomer This compound is prepared by the customary procedure by the reaction of pyrrolidine bromoacetamide with 2-(3,4-dimethoxyphenylsulfonamido)-5,2'-dichlorobenzophenone and then cyclization of the resulting product with DBU in chloroform. A product is eluted on an alumina column with DCM/AcOEt (90/10, v/v); it is the cis isomer.
M.p.=237° C.

AcOEt elutes the trans isomer, which is then recrystallized from AcOEt.
M.p.=230° C.

EXAMPLE 112

5-Chloro-3-(2-chlorophenyl)-1-(3,4-dimethoxyphenylsulfonyl)-3-hydroxyindoline-2-carboxamide, trans isomer

A)
2',5-Dichloro-2-(3,4-dimethoxyphenylsulfonamido)benzophenone 114 g of 2-amino-5,2'-dichlorobenzophenone and 100 g of 3,4-dimethoxyphenylsulfonyl chloride are mixed in 300 ml of pyridine. After 4 days at RT, the excess pyridine is evaporated off, the residue is taken up with hydrochloric water and extracted with DCM and the extract is dried and concentrated. The expected product then crystallizes from a DCM/isopropyl ether mixture.
m=181 g.
M.p.=159°-161 ° C.

B)
2',5-Dichloro-2-[N-(3,4-dimethoxyphenylsulfonyl)-N-(benzyloxycarbonylmethyl) amino ]benzophenone 172 g of the product prepared above are dissolved in 800 ml of DCM and cooled to 0° C. 11.7 g of 80% sodium hydride are added gradually under nitrogen, 256 g of benzyl bromoacetate are then added after 30 minutes and the mixture is stirred for 24 hours at RT. The DMF is evaporated off, the residue is taken up with water and extracted with DCM and the extract is dried and concentrated. The expected product crystallizes from isopropyl ether and is then recrystallized from a DCM/isopropyl ether mixture.
m=136.5 g.
M.p.=102°-104 ° C.

C) Benzyl 5-chloro-3-(2-chlorophenyl)-1-(3,4-dimethoxyphenylsulfonyl)-3-hydroxyindoline-2-carboxylate, trans isomer 3 g of the product obtained in the previous step are treated with 740 mg of TBD in 20 ml of DCM at RT for 1 hour. The reaction medium is chromatographed on silica and DCM elutes the expected compound in the form of the trans isomer, which is the only isomer formed by the cyclization reaction.

The compound obtained is recrystallized from a DCM/isopropyl ether mixture.
m=2g.
M.p.=190°-192° C.

D)
5-Chloro-3-(2-chlorophenyl)-1-(3,4-dimethoxyphenylsulfonyl)-3-hydroxyindoline-2-carboxylic acid, trans isomer The benzyl ester obtained in the previous step, in 50 ml of AcOEt, is treated with hydrogen for 30 minutes in the presence of 100 mg of 10% Pd/C. The reaction medium is filtered on Célite ®the material on the filter is washed with hot methanol and the filtrate is concentrated. The expected product crystallizes 10 from a DCM/isopropyl ether mixture.
m=1.5g.
M.p.=218°-221° C.

E)
5-Chloro-3-(2-chlorophenyl)-1-(3,4-dimethoxyphenylsulfonyl)-3-hydroxyindoline-2-carboxamide, trans isomer 180 mg of the compound obtained in the previous step, in 15 ml of DCM, are treated with 140 mg of BOP in the presence of a sufficient amount of DIPEA to solubilize the acid. After 15 minutes, gaseous ammonia is introduced for 10 minutes. The medium is poured into a saturated solution of sodium hydrogencarbonate and extracted and the extract is dried and then concentrated. The crude product is chromatographed on silica using a DCM/AcOEt mixture (80/20, v/v) as the eluent to give the expected compound, which is then recrystallized from a DCM/isopropyl ether mixture.
m=63 mg.
M.p.=183°-185° C.

EXAMPLES 113 AND 114

N-Isopentyl-5-chloro-3-cyclohexyl-3-hydroxy-1-tosylindoline-2-carboxamide, cis isomer, trans isomer A) 2-(N-tosylamino)-5-chlorophenyl cyclohexyl ketone is prepared by the customary method

B)
2-[N-(N'-Isopentylcarbamoylmethyl)-N-(tosyl)amino]-5-chlorophenyl cyclohexyl ketone 7.2 g of the compound obtained above in 130 ml of DMF are cooled to 0° C. and placed under argon, 1.1 equivalents of sodium hydride are added and the mixture is allowed to return to RT. 15.2 g of N-isopentyl-2bromoacetamide are then added and the mixture is stirred overnight at RT. The DMF is evaporated off, the residue is taken up with water and extracted with DCM and the extract is dried and concentrated. The crude product is chromatographed on silica using an ether/pentane mixture (70/30, v/v) as the eluent.

C)
N-Isopentyl-5-chloro-3-cyclohexyl-3-hydroxy-1-tosylindoline-2-carboxamide, mixture of isomers 2.1 equivalents of LDA are added to 3 g of the above product in 50 ml of anhydrous THF at −20° C. and the temperature is then kept at +4° C. for 30 minutes. The medium is poured into a saturated solution of ammonium chloride and extracted and the extract is dried and concentrated. Chromatography on silica using methylene chloride as the eluent gives the expected product in the form of a mixture of 2 isomers.

m=2 g.

D)
N-Isopentyl-5-chloro-3-cyclohexyl-3-trimethylsilyloxy-1-tosylindoline-2-carboxamide 1 g of the product obtained above is heated at 100° C. in 5 g of HMDS for 12 hours under argon in the presence of 0.1 g of imidazole. The medium is evaporated, the residue is taken up with DCM and the solution is chromatographed on silica. DCM successively elutes the less polar isomer, which is recrystallized from isopropyl ether:

m=345 mg.
M.p.=137°–138° C.

and then the more polar isomer, which is recrystallized from isopropyl ether:

m=165 mg.
M.p.=175°–176° C.

E)
N-Isopentyl-5-chloro-3-cyclohexyl-3-hydroxy-1-tosylindoline-2-carboxamide, cis isomer 150 mg of the less polar isomer obtained above are treated with 10 mg of sodium hydroxide at 0° C. in 5 ml of THF and 2 ml of water for 3 hours. The mixture is taken up with water and extracted with DCM and the extract is dried and concentrated. The crude product is recrystallized from a DCM/isopropyl ether mixture.

m=120 mg.
M.p.=189°–191° C.

F)
N-Isopentyl-5-chloro-3-cyclohexyl-3-hydroxy-1-tosylindoline-2-carboxamide, trans isomer 150 mg of the more polar isomer obtained in step D are treated with 10 mg of sodium hydroxide in 5 ml of THF and 2 ml of water for 2 hours at RT. The mixture is taken up with water and extracted with DCM and the extract is dried and concentrated. The expected product is recrystallized from a DCM/isopropyl ether mixture.

m=65 mg.
M.p.=195°–196° C.

The compounds according to the invention which are described in Table 2 below were prepared by following the procedure given in the Examples described above:

TABLE 2

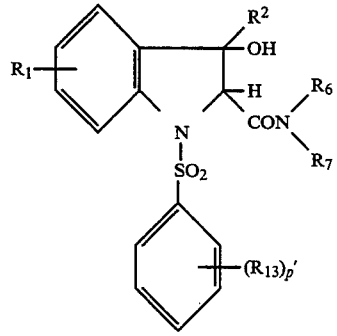

For each compound of formula (I) having the substituents $R_1$, $R_2$, $(R'_5)p$, and $NR_6R_7$ in the Table below, the cis isomer is indicated and then the trans isomer, unless stated otherwise.

| Ex. | $R_1$ | $R_2$ | $(R_{13})_{p'}$ | $-N\diagdown^{R_6}_{R_7}$ | M.p. °C. crystallization solvent |
|---|---|---|---|---|---|
| 115 | 5-Cl | 2-Cl-phenyl | 3,4-dimethoxy | $N(CH_3)_2$ | 201 DCM/isopropyl ether |
| 116 | | | | | 222 DCM/isopropyl ether |
| 117 | 5-Cl | cyclohexyl | 4-$CH_3$ | $NHCH_3$ | 224–225 DCM/isopropyl ether |
| 118 | | | | | 141–148 DCM/isopropyl ether |
| 119 trans | 5-Cl | 2-Cl-phenyl | 3,4-dimethoxy | $NHCH_3$ | 148 DCM/isopropyl ether |
| 120 | 5-Br | 2-F-phenyl | 3,4-dimethoxy | $N(CH_3)_2$ | 165 DCM/isopropyl ether |
| 121 | | | | | 214 |

TABLE 2-continued

| | | | | | |
|---|---|---|---|---|---|
| 122 cis | 5-Cl | 2-Cl-phenyl | 2,5-dimethoxy | N(CH$_3$)$_2$ | DCM/isopropyl ether 140-142 |
| 123 | 5-Cl | 2-Cl-phenyl | 4-methoxy | N(CH$_3$)$_2$ | DCM/isopropyl ether 240 |
| 124 | | | | | DCM/hexane 187 |
| 125 | 5-Cl | 2-Cl-phenyl | 3,4-dimethoxy | N(CH$_2$CH$_3$)$_2$ | DCM/hexane 213 |
| 126 | | | | | hexane/isopropyl ether 200 |
| 127 | 5-Cl | 2-Cl-phenyl | 3,4-dimethoxy | N(CH$_3$)—CH$_2$—CH$_2$—C$_6$H$_5$ | hexane/isopropyl ether 125-130 |
| 128 | | | | | hexane/isopropyl ether 140-142 |
| 129 | 5-Cl | 2-Cl-phenyl | 2,4-dimethoxy | N(CH$_3$)$_2$ | DCM/isopropyl ether 213 |
| 130 | | | | | 206 |
| 131 | 5-Cl | 2-methoxy-phenyl | 3,4-dimethoxy | N(CH$_3$)$_2$ | 205 |
| 132 | | | | | hexane/isopropyl ether 206 |
| 133 | 5-CH$_3$ | 2-Cl-phenyl | 3,4-dimethoxy | N(CH$_2$CH$_3$)$_2$ | hexane/isopropyl ether 189 |
| 134 | | | | | isopropyl ether 191 |
| 135 | 5-CH$_3$ | 2-Cl-phenyl | 2,4-dimethoxy | N(CH$_2$CH$_3$)$_2$ | isopropyl ether 208-209 |
| 136 | | | | | isopropyl ether 214-215 |
| 137 | 5-Cl | 2-Cl-phenyl | 2,4-dimethoxy | N(CH$_2$CH$_3$)$_2$ | isopropyl ether 225 |
| 138 | | | | | 200 |
| 139 | 5-Cl | 2-Cl-phenyl | 4-cyano | N(CH$_3$)$_2$ | 242-243 |
| 140 | | | | | THF/EtOH 228-231 |
| 141 cis | 5-Cl | 2-Cl-phenyl | 3,4-dimethoxy | N(C$_4$H$_9$)$_2$ | DCM/isopropyl ether 203 |
| 142 | 5-Cl | cyclohexyl | 3,4-dimethoxy | N(CH$_2$CH$_3$)$_2$ | DCM/isopropyl ether 117-120 |
| 143 | | | | | NMR |
| 144 cis | 5-Cl | 2-F-phenyl | 4-nitro | N(CH$_3$)$_2$ | 230 |

NMR spectrum
Example 143: trans isomer
0.2-1.8 ppm: m: 17H: 2CH$_3$ (ethyl), 11H cyclohexyl
2.8-3.5 ppm: m: 4H: N—(CH$_2$)$_2$—
3.7 ppm: s: 3H: OCH$_3$
3.75 ppm: s: 3H: OCH$_3$
4.7 ppm: s: 1H: H (indoline)
5.65 ppm: s: 1H: OH (indoline)
6.8-7.6 ppm: m: 6H: aromatic protons

EXAMPLES 145 AND 146

Methyl 5-chloro-3-(2-chlorophenyl)-3-hydroxy-1-tosylindoline-2-carboxylate, dextrorotatory cis isomer, levorotatory cis isomer The optical isomers of methyl 5-chloro-3-(2chlorophenyl)-3-hydroxy-1-tosylindoline-2-carboxylate, described in Example 48 of Table 1, were separated by preparative chromatography on a chiral column.

Supercritical phase analytical chromatography is first carried out on the product of Example 48.

The column used is a Chiralcel OD ® column marketed by DAICEL. This column consists of silica gel coated with cellulose carbamate.

The eluent is a carbon dioxide/propan-2-ol/diethylamine mixture (75/25/0.3, v/v/v) used at a flow rate of 2 ml/minute. The exit pressure is 160 atmospheres, the temperature is 32° C. and UV detection is carried out at 226 nm.

The chromatogram shows 2 peaks of equal areas and with retention times of about 4 minutes and 5.4 minutes.

A Chiralcel ® column is also used for preparative chromatography.

The sample of product to be chromatographed is dissolved in methanol (30 mg/ml) and 1 ml is injected into the column. The eluent is a hexane/propan-2-ol mixture (80/20, v/v) used at a flow rate of 1.5 ml/minute. UV detection is carried out at 226 nm. The analysis time is 45 minutes. Twelve fractions were collected and analyzed in the supercritical phase.

Under the same conditions, 13 injections of 30 mg are then carried out. The fractions corresponding to the first peak, collected between 16 and 24 minutes, are pooled; the fractions corresponding to the second peak, collected between 29 and 42 minutes, are pooled. After passage under a stream of nitrogen, each batch is recrystallized from a DCM/isopropyl ether/hexane mixture.

The first peak gives a product with a chromatographic purity of more than 99.9%; this is the dextrorotatory cis isomer.

$\alpha_D^{25} = +236$ (chloroform).
M.p.=174°–177° C. (after recrystallization from DCM/hexane/isopropyl ether).
m=130 mg.

The second peak gives a product with a chromatographic purity of more than 99.5%; this is the levorotatory cis isomer.

$\alpha_D^{25} = -238$ (chloroform).
M.p.=174°–177° C. (after recrystallization from DCM/hexane/isopropyl ether).
m=83 mg.

EXAMPLE 1a

N-methyl-N-methoxycarbonylmethyl-5-bromo-3-(2-fluorophenyl)-1-(3,4-dimethoxyphenylsulfonyl)-3-hydroxy-2-indolinecarboxamide, cis isomer.

A) Methyl N-bromoacetylsarcosinate

This compound is prepared according to T. D. Harris et al. in J. Heterocyclic Chem., 1981, 18, 423.

B) 5-Bromo-2-(3,4-dimethoxyphenylsulfonamido)-2'-fluorobenzophenone 20 g of 2-amino-5-bromo-2'-fluorobenzophenone are heated at 85° C. for 48 hours in 120 ml of dry pyridine in the presence of 20 g of 3,4-dimethoxyphenylsulfonyl chloride. The mixture is cooled, poured into ice-cold water, the solid is filtered off, the solid is extracted with AcOEt, the organic phase is washed with water, a solution of hydrochloric acid (1N), water and then saline water. After drying over magnesium sulfate and evaporating the solvent under vacuum, a solid is obtained which is recrystallized from DCM/isopropyl ether.
m=28 g.
M.p.=125°–128° C.

C) 5-Bromo-2-[N-(3,4-dimethoxyphenylsulfonyl)-N-(N'-methyl-N'-(methoxycarbonylmethyl)carbamylmethyl)]amino-2'-fluorobenzophenone 3.5 g of the compound prepared in Step B are dissolved in anhydrous DMF at 0° C. under argon and 250 mg of 80% sodium hydride are added; after 15 minutes, 4.85 g of the compound prepared in Step B are added and the mixture is left stirring at RT for 12 hours. The reaction mixture is poured into water, the solid is filtered off and then the solid is dissolved in AcOEt, the organic phase is washed with water and then with saline water and the solvent is evaporated under vacuum. The oil obtained is filtered on silica by eluting with a DCM/AcOEt (85/15; v/v) mixture. It is recrystallized from a DCM/isopropyl ether/MeOH mixture.
m=3.2g.
M.p.=136°–137° C.

D) N-methyl-N-methoxycarbonylmethyl-5-bromo-3-(2-fluorophenyl)-1-(3,4-dimethoxyphenylsulfonyl)-3-hydroxy-2indolinecarboxamide, cis isomer.

3.2 g of product obtained in the preceding step are dissolved in DCM (3 ml), 750 mg of DBU are added and the mixture is left stirring at RT for 24 hours. The reaction mixture is poured onto a silica column; by eluting with DCM/AcOEt (90/10; v/v), a product is obtained which is the mixture of the two isomers (cis and trans) of the expected compound. This product is triturated in a hexane/isopropyl ether mixture and the solid obtained is filtered. The filtration liquors are chromatographed on an alumina column which was preequilibrated in a DCM/AcOEt (70/30; v/v) mixture. The least polar compound is eluted with a DCM/AcOEt (60/40; v/v) mixture and is then recrystallized from a DCM/hexane/isopropyl ether mixture.
M.p.=95° C. with evolution of gas.

EXAMPLES 2a AND 3a

2-[(4-Benzyloxycarbonyl)-1-piperazinyl]carbonyl-5-chloro-3-(2-chlorophenyl)-1-(3,4-dimethoxyphenylsulfonyl)-3-hydroxyindoline, cis isomer and trans isomer

A) 1-Bromacetyl-4-(benzyloxycarbonyl)piperazine

A mixture of 22 g of 4-benzyloxycarbonylpiperazine and 10.1 g of triethylamine in 200 ml of ether is cooled to 0° C. 20.2 g of bromoacetyl bromide in 100 ml of ether are added over 30 minutes and the mixture is left to return to RT. After 4 hours, the reaction mixture is washed with water, dried, concentrated and then chromatographed on silica. The mixture DCM/AcOEt (95/5; v/v) elutes the expected compound which is recrystallized from DCM/isopropyl ether.
m=9g.
M.p.=100°–101° C.

B) 2',5-Dichloro-2-(3,4-dimethoxyphenylsulfonamido)benzophenone 5.6 g of 2-amino-2',5-dichlorobenzophenone and 5 g of 3,4-dimethoxyphenylsulfonyl chloride are heated in pyridine at 100° C. overnight. The pyridine is evaporated to dryness, water is added and extraction is carried out with ethyl acetate containing a small amount of DCM. After washing more than once with water and drying over sodium sulfate, the extract is evaporated under vacuum and 7.7 g of the expected product are recrystallized in a DCM/AcOEt mixture.
M.p.=164 ° C.

C) 2',5-Dichloro-2-[N-(3,4-dimethoxyphenylsulfonyl)-N-(4-benzyloxycarbonyl-1-piperazinylcarbonylmethyl)]aminobenzophenone 2.3 g of the benzophenone prepared in Step B are placed in 10 ml of DMF and treated with 200 mg of 80% sodium hydride in oil. After 30 minutes, 5.3 g of the compound prepared in Step A are added and the mixture is stirred for 60 hours at RT. The mixture is poured into water, the precipitate is filtered, taken up in DCM, dried and then concentrated and chromatographed on silica. The DCM/AcOEt (90/10; v/v) mixture elutes the expected product which crystallizes from a DCM/isopropyl ether mixture.
m=2g.
M.p.=173°–175° C.

D) 2-[(4-Benzyloxycarbonyl)-1-piperazinyl]carbonyl-5-chloro-3-(2-chlorophenyl)-1-(3,4-dimethoxyphenylsulfonyl)-3-hydroxyindoline, cis isomer and trans isomer 1 g of the compound obtained in the preceding step is suspended in 20 ml of methanol and 20 ml of THF and is treated with 75 mg of sodium methylate. After 2 hours, the mixture is neutralized by the addition of a small amount of dry ice, is concentrated to dryness and then taken up in water; the mixture is then extracted with DCM, the extract is dried and concentrated. The crude product is chromatographed on alumina, and the DCM/AcOEt (80/20; v/v) mixture elutes the 2 isomers successively.

The least polar isomer is recrystallized from a DCM/hexane mixture. This compound is the cis isomer.
m=262 mg.
M.p.=169°–179° C.

The most polar isomer is recrystallized from the DCM/isopropyl ether mixture.
m=200 mg.
M.p.=209°–211° C.

EXAMPLE 4a

5-Chloro-3-(2-chlorophenyl)-1-(3,4-dimethoxyphenylsulfonyl)-3-hydroxy-2-(1-piperazinylcarbonyl)indoline, cis isomer 200 mg of the cis isomer prepared in the preceding example are dissolved in 10 ml of ethanol and 5 ml of THF and are hydrogenolyzed at RT in the presence of 10% Pd/C. After 30 minutes, the mixture is filtered on Celite®, the filtration liquors are concentrated and then chromatographed on silica. The MeOH/DCM (10/90; v/v) mixture elutes the expected product which is recrystallized from a DCM/isopropyl ether mixture.
m=110 mg.
M.p. 230°–233° C.

EXAMPLES 5a AND 6a

5-Chloro-3-(2-chlorophenyl)-1-(3,4-dimethoxyphenylsulfonyl)-3-hydroxy-2-morpholinocarbonylindoline, cis isomer and trans isomer A)
2′,5-Dichloro-2-[N-(3,4-dimethoxyphenylsulfonyl)-N(morpholinocarbonylmethyl)]aminobenzophenone 5 g of 2′,5-dichloro-2-(3,4-dimethoxyphenylsulfonamido)benzophenone are treated with 350 mg of 80% sodium hydride in 30 ml of DMF at RT for 20 minutes. 4.5 g of morpholinebromoacetamide are added and then the mixture is stirred at RT for 48 hours. The mixture is poured into water, the precipitate is filtered, it is dissolved in DCM, the solution is dried and concentrated. The product formed is recrystallized from a DCM/isopropyl ether mixture. 5.4 g are obtained.
M.p.=173°–176° C.

B)
5-Chloro-3-(2-chlorophenyl)-1-(3,4-dimethoxyphenylsulfonyl)-3-hydroxy-2-morpholinocarbonylindoline, cis isomer 1 g of the product obtained in the preceding step is dissolved in the methanol (10 ml) and THF (20 ml) mixture and is treated with 92 mg of sodium methylate at RT for 1 hour. The mixture is neutralized with dry ice, the solvents are partly evaporated, the mixture is taken up in water, extracted with DCM and the extract is dried, concentrated and chromatographed on alumina. The DCM/AcOEt (70/30; v/v) mixture elutes the least polar isomer which is recrystallized from a DCM/isopropyl ether mixture.
m=215 mg: cis isomer.
M.p.=260°–264° C.

C)
5-Chloro-3-(2-chlorophenyl)-1-(3,4-dimethoxyphenylsulfonyl)-3-hydroxy-2-morpholinocarbonylindoline, trans isomer By the chromatography of the preceding step, a more polar product is collected by eluting with the AcOEt/MeOH (90/10) ; v/v) mixture. After recrystallizing from a DCM/isopropyl ether mixture, there is obtained:
m=513 mg: trans isomer.
M.p.=240°–241° C.

EXAMPLE 7a

N-Methyl-N-carboxymethyl-5-bromo-3-(2-fluorophenyl)-1-(3,4-dimethoxyphenylsulfonyl)-3-hydroxy-2-indolinecarboxamide, cis isomer 200 mg of the compound prepared in Example 1a are dissolved in 3 ml of MeOH and 1 ml of water containing 13 mg of sodium hydroxide. After stirring for 24 hours at RT, one drop of concentrated sodium hydroxide solution is added to bring the reaction to an end and then, after 15 minutes, the mixture is acidified to pH 3 by addition of a potassium hydrogensulfate solution. Water is added, the mixture is extracted with AcOEt and the extract is washed with water and dried over magnesium sulfate and the solvent is evaporated under vacuum. The product obtained is recrystallized from DCM/isopropyl ether.
M.p.=206°–208° C.

EXAMPLES 8a AND 9a

5-Chloro-3-(2-chlorophenyl)-1-(3,4-dimethoxyphenylsulfonyl)-3-hydroxy-2-(4-ethylcarboxylatepiperidinocarbonyl)indoline, cis isomer, trans isomer A) Ethyl N-bromoacetyl-4-piperidinecarboxylate This product is prepared from ethyl 4-piperidinecarboxylate, which is commercially available.

B)
2′,5-Dichloro-2-[N-(3,4-dimethoxyphenylsulfonyl]-N-(4ethylcarboxylatepiperidinocarbonylmethyl)-]aminobenzophenone 8 g of 2′,5-dichloro-2-(3,4-dimethoxyphenylsulfonamido)benzophenone are dissolved in 100 ml of DMF and then 541 mg of sodium hydride are added. After stirring for 30 minutes, 9.5 g of the compound of Step A are added and the mixture is left stirring for 18 hours at RT. The mixture is concentrated under vacuum, taken up in water, extracted with ethyl acetate and the extract is dried and concentrated. The oil obtained is chromatographed on silica, eluting with the AcOEt/DCM/hexane (40/10/50; v/v/v) mixture. The expected product crystallizes from ether.
m=3.5g.
M.p.=128° C.

C)
5-Chloro-3-(2-chlorophenyl)-1-(3,4-dimethoxyphenylsulfonyl)-3-hydroxy-2-(4-ethylcarboxylatepiperidinocarbonyl)indoline, cis isomer, trans isomer A mixture containing 3.4 g of the compound prepared in the preceding step and 869 mg of DBU in 10 ml of chloroform is brought to 60° C. for 18 hours. The reaction mixture is then filtered on an alumina column, eluting with a DCM/AcOEt (90/10; v/v) mixture in order to obtain the cis isomer.
m=700 mg.
M.p.=110° C.
Pure ethyl acetate elutes the trans isomer.
m=610 mg.
M.p.=187° C.

EXAMPLES 10a AND 11a

N-methyl-N-(2-pyridylethyl)-5-chloro-3-(2-chlorophenyl)-1-(3,4-dimethoxyphenylsulfonyl)-3-hydroxy-2indolinecarboxamide, cis isomer, trans isomer A)
N-[2-(2-chlorophenylcarbonyl)-5-chlorophenyl]-N-(3,4dimethoxyphenylsulfonyl)glycine acid a)
2',5-Dichloro-2-(3,4-dimethoxyphenylsulfonamido)benzophenone This compound is prepared in Example 2a-3a, Step B.

b)
2',5-Dichloro-2-[N-(3,4-dimethoxyphenylsulfonyl)-N-benzyloxycarbonylmethyl]aminobenzophenone 172 g of the product prepared previously are dissolved in 800 ml of DMF and cooled to 0° C. 11.7 g of 80% sodium hydride is added progressively under nitrogen and then, after 30 minutes, 256 g of benzyl bromoacetate are added and the mixture is left stirring for 24 hours at RT. The DMF is evaporated, the residue is taken up in water, extracted with DCM, and the extract dried and concentrated. The expected product crystallizes from isopropyl ether and is then recrystallized from a DCM/isopropyl ether mixture.
m=136.5 g.
M.p.=102°-104° C.

c)
N-[2-(2-Chlorophenylcarbonyl)-5-chlorophenyl]-N-(3,4-dimethoxyphenylsulfonyl)glycine acid 50 g of the benzyl ester obtained previously are dissolved in 500 ml of AcOEt and 2.5 g of 5% Pd/C are added under nitrogen. The solution is vigorously stirred and a stream of hydrogen is passed in for 5 hours. At the end of the hydrogenation, the product crystallizes. The mixture is filtered on Celite ®, the cake is washed copiously with hot DCM and then the organic phase is concentrated. The expected product crystallizes and is then recrystallized from the DCM/isopropyl ether mixture.
m=b 33.7 g.
M.p.=177°-178° C.

B)
2',5-Dichloro-2-[N-(3,4-dimethoxyphenylsulfonyl)-N-(N'-(2-(2-pyridyl)ethyl)-N'-methyl)carbamoylmethyl]aminobenzophenone 2 g of the acid prepared in Step A are placed in 30 ml of DCM and 1.13 g of 2-(2-methylaminoethyl)pyridine, then 844 mg of triethylamine and finally 1.92 g of BOP are added and then the mixture is left stirring for 18 hours at RT. The mixture is taken up with water, the organic phase is separated, washed with a sodium carbonate solution, dried and concentrated. After chromatography on silica, the expected product is collected by eluting with the DCM/MeOH (95/5); v/v) mixture.
m=2g.
M.p.=150° C.

C)
N-methyl-N-(2-pyridylethyl)-5-chloro-3-(2-chlorophenyl)-1-(3,4-dimethoxyphenylsulfonyl)-3-hydroxy-2indolinecarboxamide A mixture containing 1.7 g of the product obtained in the preceding step and 442 mg of DBU in DCM is heated at 55° C. for 18 hours. The reaction mixture is chromatographed on alumina. The AcOEt/DCM (40/60); v/v) mixture elutes the cis isomer:
m=410 mg.
M.p.=191° C.
Pure AcOEt elutes the trans isomer:
m=790 mg.
M.p.=154° C.

EXAMPLE 12a 2-(4-Carboxypiperidinocarbonyl)-5-chloro-3-(2-chlorophenyl)-1-(3,4-dimethoxyphenylsulfonyl)-3-hydroxyindoline, cis isomer 500 mg of the cis isomer prepared in Example 9a are placed in 5 ml of methanol in the presence of 48 mg of sodium hydroxide in 1 ml of water. After stirring for 18 hours, the mixture is poured into water, acidified with dilute hydrochloric acid, then extracted with DCM and the extract dried and concentrated. The solid obtained is purified by chromatography on silica, eluting with the DCM/MeOH (95/5; v/v) mixture and the product obtained is then crystallized from a DCM/isopropyl ether mixture.
m=250 mg.
M.p.=150° C.

EXAMPLES 13a AND 14a

N-Methyl-N-(1-methyl-4-piperidyl)-5-chloro-3-(2-chlorophenyl)-1-(3,4-dimethoxyphenylsulfonyl)-3-hydroxy-2-indolinecarboxamide, cis isomer and trans isomer A)
2',5-Dichloro-2-[N-(3,4-dimethoxyphenylsulfonyl)-N-(N'-methyl-N'-(methyl-4-piperidyl)carbamoylmethyl]aminobenzophenone 2 g of the acid prepared in Example 10a-11a, Step A in 50 ml of DCM are mixed with 650 mg of 4-methylamino-1methylpiperidine in the presence of 1.90 g of BOP. After stirring for 2 hours at RT, the organic phase is washed with carbonated water, dried and concentrated. The residue is then chromatographed on silica, eluting with the DCM/MeOH (90/10; v/v) mixture. 1.2 g of the expected product are obtained.
M.p.=165°-166° C.

B)
N-Methyl-N-(methyl-4-piperidyl)-5-chloro-3-(2-chlorophenyl)-1-(3,4-dimethoxyphenylsulfonyl)-3-hydroxy-2-indolinecarboxamide, cis isomer and trans isomer 650 mg of the product obtained in the preceding step are treated overnight with 100 mg of sodium methylate in 5 ml of methanol. Dry ice is added, the solvent is evaporated, the residue is taken up in carbonated water, extracted with DCM and the extract dried and concentrated and then chromatographed on silica. The methanol/DCM (5/95; v/v) mixture elutes the 2 isomers successively. Each is then recrystallized from a DCM/isopropyl ether mixture.

The trans isomer is the least polar under these conditions,
m=205 mg.
M.p.=181° C.
Cis isomer: m=150 mg.
M.p.=97° C.: contains 0.25 M of isopropyl ether.

EXAMPLES 15a AND 16a

5-Chloro-3-(2-chlorophenyl)-1-(3,4-dimethoxyphenylsulfonyl)-3-hydroxy-2-[4-methyl-1-piperazinylcarbonyl]indoline, cis isomer and trans isomer A)
2',5-Dichloro-2-[N-(3,4-dimethoxyphenylsulfonyl)-N((4-methyl-1-piperazinyl)carbamoylmethyl)-)aminobenzophenone This compound is obtained by the action of N-methylpiperazine on the acid prepared in Example 10a-11a Step A.
M.p.=165°-167° C.

B)
5-Chloro-3-(2-chlorophenyl)-1-(3,4-dimethoxyphenylsulfonyl)-3-hydroxy-2-[4-methyl-1-piperazinylcarbonyl]indoline, cis isomer and trans isomer The compound of the preceding step is cyclized by proceeding as in Example 12a-13a. The 2 isomers formed are separated by chromatography on alumina. The DCM/AcOEt (75/25; v/v) mixture elutes the least polar product: the cis isomer, which is recrystallized from a DCM/isopropyl ether mixture.
M.p.=120° C.: contains 0.25 M of isopropyl ether.

The DCM/MeOH mixture elutes the most polar compound, the trans isomer which is then recrystallized from methanol.
M.p.=189° C.

EXAMPLES 17a AND 18a

N-Isopropyl-N-methoxycarbonylethyl-5-chloro-3-(2-chlorophenyl)-1-(3,4-dimethoxyphenylsulfonyl)-3-hydroxy-2-indolinecarboxamide, cis isomer and trans isomer A)
N-Isopropyl-N-(methoxycarbonylethyl)bromoacetamide 90 g of isopropylamine are added dropwise to 130 g of a solution, cooled to -10° C., of methyl acrylate in 300 ml of methanol. After 72 hours at RT, the mixture is evaporated and the residue is then distilled. The oil obtained (168.3 g) is methyl 3-(N-isopropyl)-aminopropionate.
B.p. =73°-78° C. at 15 mm Hg.

29 g of the compound obtained in 100 ml DCM are mixed with 20.2 g of bromoacetyl bromide in 100 ml of DCM at 0° C. After 12 hours at RT, the solvent is evaporated, the residue is taken up in water, extracted with ethyl acetate and the extract dried and concentrated. The oil obtained is used as it is in the following step.

B)
2',5-Dichloro-2-[N-(3,4-dimethoxyphenylsulfonyl)-N-(N'-isopropyl-N'-methoxycarbonylethyl)carbamoylmethyl]aminobenzophenone This compound is obtained by following the usual procedure, by reacting the product prepared in Step A with 2',5-dichloro-2-(3,4-dimethoxyphenylsulfonamido)benzophenone in the presence of sodium hydride.
M.p.=135°-137° C. (recrystallization: DCM/isopropyl ether).

C)
N-Isopropyl-N-methoxycarbonylethyl-5-chloro-3-(2-chlorophenyl)-1-(3,4-dimethoxyphenylsulfonyl)-3-hydroxy-2-indolinecarboxamide, cis isomer and trans isomer This product is obtained by cyclizing the compound prepared in Step B, in the presence of DBU. The cis isomer is separated by chromatography on alumina, eluting with a DCM/AcOEt (90/10; v/v) mixture. The product is then crystallized from an AcOEt/hexane mixture.
M.p.=153°-155° C.

The trans isomer is obtained by eluting the alumina column with ethyl acetate. The product is then recrystallized from a methanol/isopropyl ether mixture.
M.p.=182°-185° C.

EXAMPLES 19a AND 20a

N-Methyl-N-methoxycarbonylmethyl-5-chloro-3-(2-chlorophenyl)-1-(3,4-dimethoxyphenylsulfonyl)-3-hydroxy-2-indolinecarboxamide, cis isomer and trans isomer The 2 isomers of this compound are prepared according to the procedure described in Example 1. They are separated by chromatography on alumina. The DCM/AcOEt (80/20; v/v) mixture elutes the cis isomer. This crystallizes from a DCM/isopropyl ether mixture in the form of a white powder containing 0.25 mole of isopropyl ether. It is converted to a foam by heating in vacuum.

The NMR spectrum of the cis isomer (Example 19a) is given in FIG. 1.

The trans isomer is eluted with pure AcOEt. It is recrystallized from DCM/isopropyl ether.
M.p.=176°-178 ° C.

Figure 2:
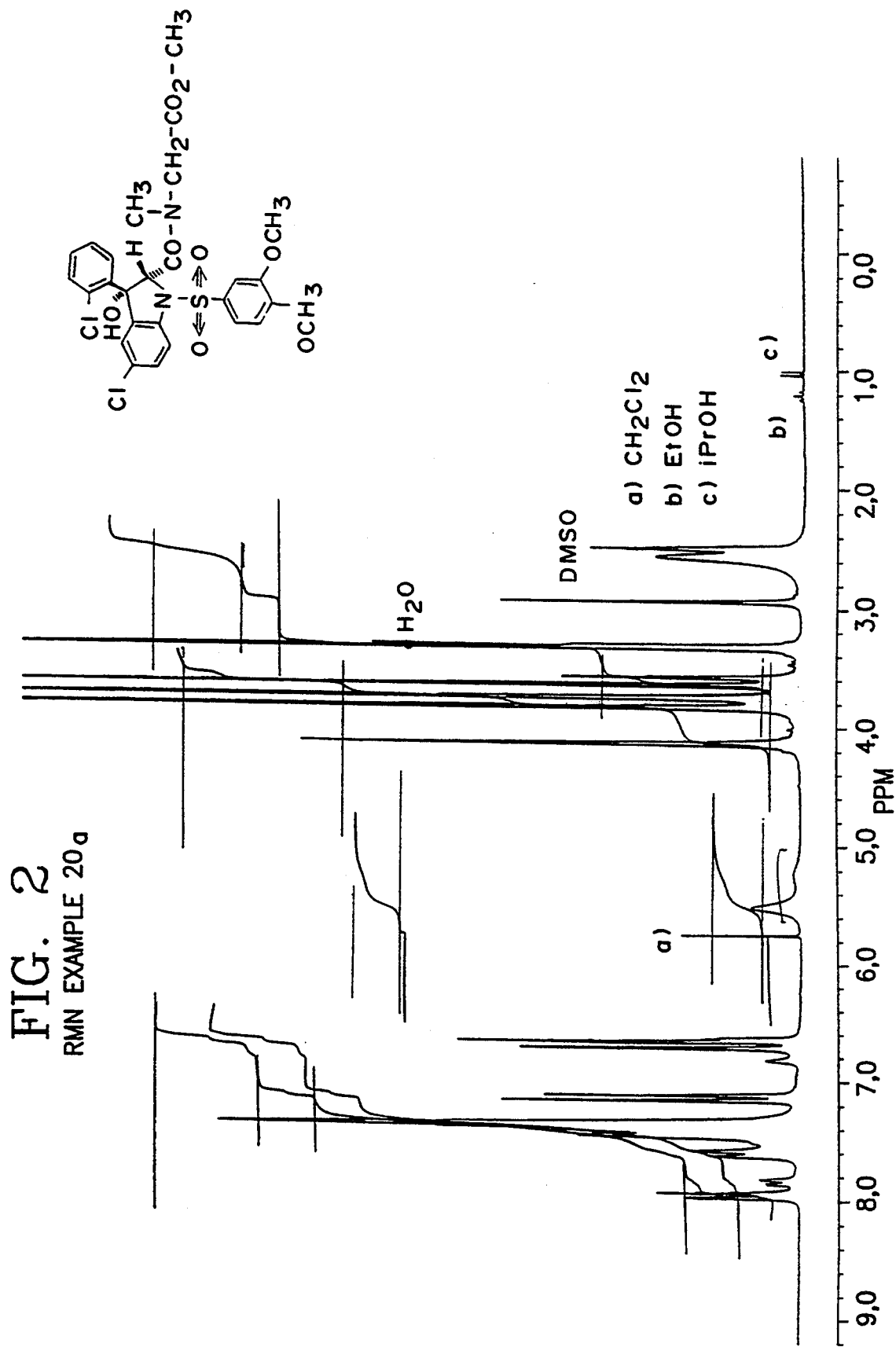

The NMR spectrum of the trans isomer (Example 20a) is given in FIG. 2.

EXAMPLES 21a AND 22a

N-Methyl-N-carboxymethyl-5-chloro-3-(2-chlorophenyl)-1-(3,4-dimethoxyphenylsulfonyl)-3-hydroxy-2-indolinecarboxamide, cis isomer and trans isomer These compounds are each prepared from the compounds described in Examples 19a and 20a according to the procedure described in Example 8a.

Cis isomer: M.p.=220°-222° C. after recrystallizing from a DCM/isopropyl ether/MeOH mixture.

Trans isomer: M.p.=222°-225° C. after recrystallizing from a DCM/isopropyl ether mixture.

EXAMPLES 23a AND 24a

N-Methyl-N-carbamoylmethyl-5-chloro-3-(2-chlorophenyl)-1-(3,4-dimethoxyphenylsulfonyl)-3-hydroxy-2-indolinecarboxamide, cis isomer and trans isomer Each isomer is obtained from the corresponding isomer of the acid prepared in Example 21a-22a.

605 mg of the trans isomer of the acid obtained in the preceding example are dissolved in 10 ml of DCM, and 435 mg of BOP and 260 mg of DIPEA are added. After 5 minutes at RT, 6 ml of 20% aqueous ammonia solution are added with vigorous stirring and the mixture is left stirring for 4 hours. A sodium carbonate solution is added and the mixture is then extracted with DCM. The organic phase is washed successively with water, a sodium hydrogensulfate solution, and water and is then dried over magnesium sulfate. After evaporating, the residue is chromatographed on silica gel and is eluted with an AcOEt/MeOH (95/5; v/v) mixture. The product obtained is crystallized twice from a DCM/EtOH mixture at 0° C.

M.p.=236° C.

Figure 3:
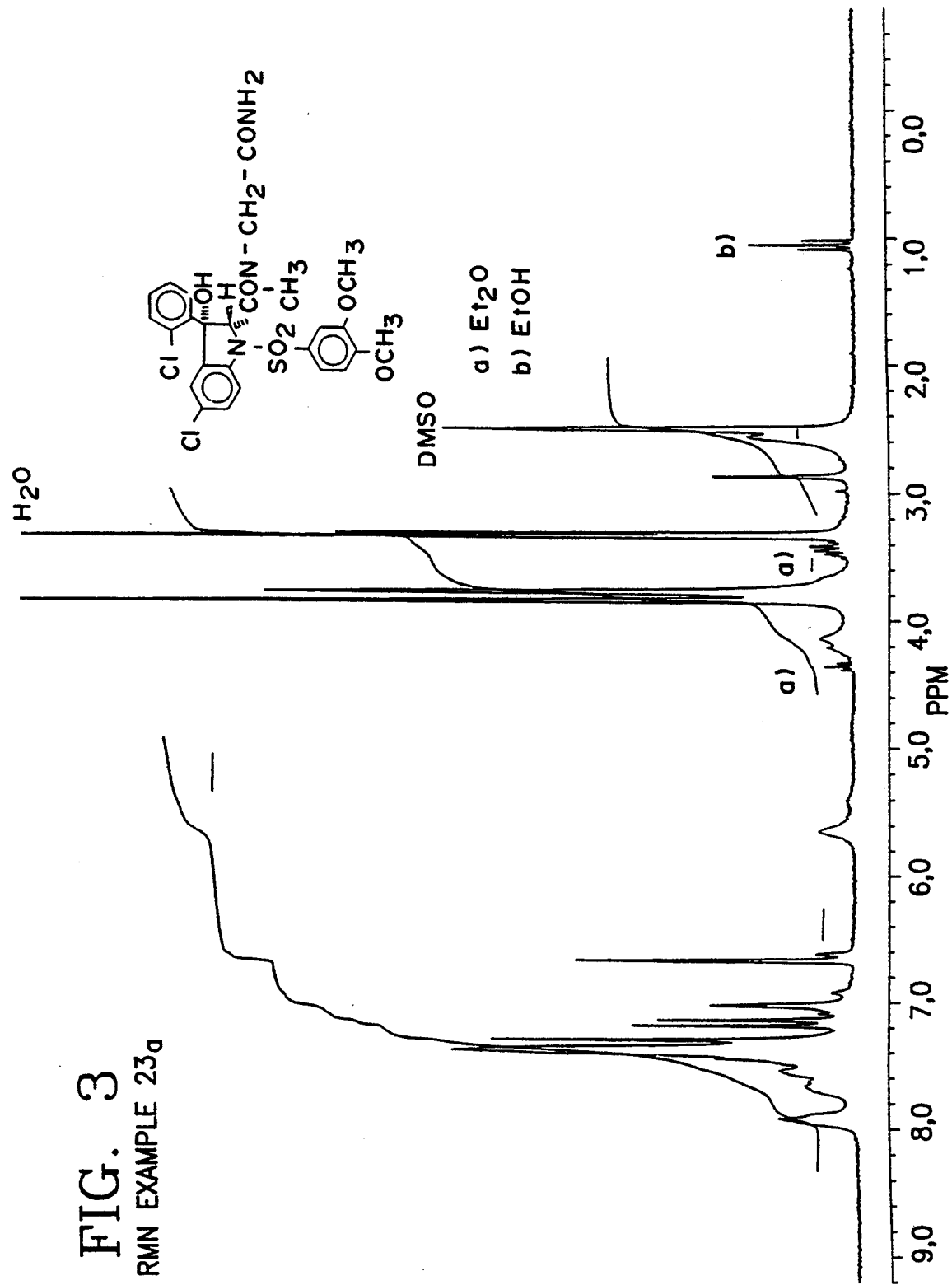

The NMR spectrum of the trans isomer (Example 23a)is given in FIG. 3.

Using the same procedure, the cis isomer is prepared.

The expected product crystallizes from DCM/isopropyl ether. The micronized compound, dried in vacuum at 70° C. for 8 hours, contains 0.25 mole of isopropyl ether.

Figure 4:
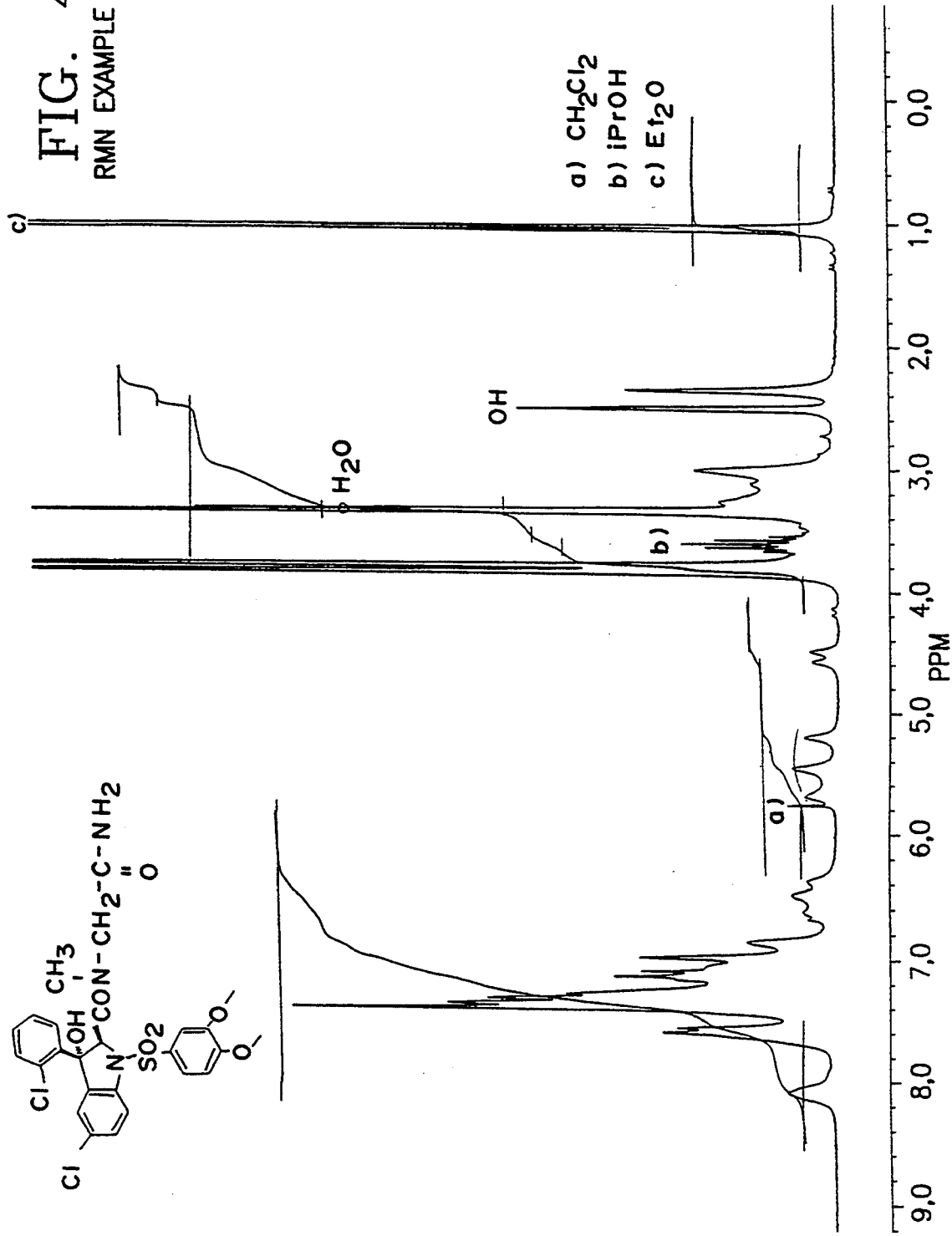

The NMR spectrum of the cis isomer (Example 24a)is given in FIG. 4.

EXAMPLES 25a AND 26a

5-Chloro-3-(2-chlorophenyl)-1-(3,4-dimethoxyphenylsulfonyl)-3-hydroxy-1-(4-hydroxy-1-piperidyl)carbonylindoline, trans isomer This compound is prepared from N-[2-(2-chlorophenylcarbonyl)-5-chlorophenyl]-N-(3,4-dimethoxyphenylsulfonyl)glycine acid described in Example 11a–12a, Step A.

The process is then carried out as in Example 11a–12a for the addition of 4-hydroxypiperidine, in the presence of BOP and triethylamine. The product obtained is then cyclized according to the usual method in the presence of DBU. The 2 isomers are separated by chromatography on alumina. The DCM/MeOH (99/1; v/v) mixture elutes the cis isomer.

The product crystallizes from a DCM/hexane/MeOH mixture and the solid obtained is then triturated in DCM/hexane to provide an amorphous powder.

The cis isomer is characterized by its NMR spectrum at 388° K.

1–1.8 ppm:m:4H:CM2 at positions 3 and 5 of the piperidine
2.8–3.65 ppm:m:5H:CH$_2$ at positions 2 and 6 of the piperidine and CH at position 5
3.75 ppm:2s:6H:2OCH$_3$
4.15 ppm:d:1H:OH on piperidine
5.45 ppm:s:1H:CH (indoline)
6.1 ppm:s:1H:OM indoline
6.8–7.6 ppm:m:10H:H aromatic
DMSO:2.4 ppm
DOH:2.75 ppm The DCM/MeOH (97/3; v/v) mixture elutes the trans isomer which is recrystallized from DCM/isopropyl ether.

M.p.=232°–234° C.

SYNTHESES in the (L)-Proline series: Examples 27a, 28a, 29a and 30a.

EXAMPLES 27a AND 27b

5-Chloro-3-(2-chlorophenyl)-1-(3,4-dimethoxyphenylsulfonyl)-3-hydroxy-2-[(2S)-(2-methoxycarbonyl)pyrrolidinocarbonyl]indoline, (cis isomerism: 2 compounds)

A) Methyl (L)-N-(bromoacetyl)prolinate 20 g of triethylamine and 20 g of bromoacetyl bromide in 30 ml of DCM are added simultaneously to a solution of 16.7 g of methyl (L)-prolinate hydrochloride in 20 ml of DCM while maintaining the temperature at −5° C. and the mixture is then stirred at RT for 24 hours. Water is added, and the mixture is washed with a solution of KHSO$_4$, with water, with a sodium bicarbonate solution and with water and is then dried over magnesium sulfate. After evaporating, an oil is obtained which is dried under vacuum. This oil, pure by TLC, is used as it is in the following step.

B)
2′,5-Dichloro-2-[N-(3,4-dimethoxyphenylsulfonyl)-N-((2S)-(2-methoxycarbonyl)pyrrolidinocarbonylmethyl)]-aminobenzo-phenone 4.66 g of 2′,5-dichloro-2-(3,4-dimethoxyphenylsulfonamido)benzophenone are dissolved in 40 ml of anhydrous DMF under argon, at 0° C., 340 mg of 80% sodium hydride are added and then, after 30 minutes, 6.5 g of the compound obtained in Step A. After 4 days at RT, the mixture is poured into water, extracted with AcOEt, the extract washed with water, with saline water and then dried over magnesium sulfate and evaporated under vacuum. A solid containing a small amount of the starting brominated derivative is eluted with a DCM/AcOEt (85/15; v/v) mixture by chromatography on silica gel. A sample is recrystallized from DCM/isopropyl ether.

m=1.2 g.
M.p.=141°–142° C.
$\alpha_D^{25}=-43.7$ (c=1; MeOH/THF: 8/2; v/v)
Analysis Calculated C:54.81; H:4.44; N:4.41. Found C: 54.40; H: 4.54; N: 4.55.

C)
5-Chloro-3-(2-chlorophenyl)-1-(3,4-dimethoxyphenylsulfonyl)-3-hydroxy-2-[(2S)-(2-methoxycarbonyl)pyrrolidinocarbonyl]indoline, (cis isomerism)

1.1 g of the compound obtained in the preceding step are heated in 4 ml of methylene chloride for 24 hours with one equivalent of DBU. HPLC analysis of an aliquot shows the existence of the expected 4 isomers. After 24 hours, the reaction mixture is poured onto an alumina column, pre-equilibrated in the DCM/AcOEt (90/10; v/v) mixture and is eluted with the DCM/AcOEt (90/10; v/v to 70/30; v/v) mixture. 510 mg of a mixture of the 2 least polar compounds are obtained in the ratio 4/1 (measured by HPLC).

1°) Two successive crystallizations from DCM/isopropyl ether while cold provide the major compound.
m=180 mg.
$\alpha_D^{25}=-247$(c=0.4; chloroform).
M.p.=187°–190° C.

2°) The crystallization mother liquors of the preceding compound are chromatographed on alumina by eluting with DCM/AcOEt (85/15; v/v). The preceding compound is thus separated from the second, the latter is dissolved in the minimum amount of DCM and is then precipitated by addition of the minimum amount of hexane.

$\alpha_D^{26}=+136$ (c=0.24; chloroform).

EXAMPLE 28a 2-((2S)-2-Carboxypyrrolidinocarbonyl)-5-chloro-3-(2-chlorophenyl)-1-(3,4-dimethoxyphenylsulfonyl)-3-hydroxyindoline, cis isomer 430 mg of the compound prepared in Example 27 are dissolved in 6 ml of methanol, 41 mg of sodium hydroxide in 1 ml of water are added and the mixture is stirred for 24 hours at RT. The mixture is acidified to pH 3 with a few drops of a potassium hydrogensulfate solution and is extracted with ethyl acetate. The extract is washed with water and is then dried over magnesium sulfate. Chromatography is carried out on a silica column prepared in a DCM/pentane (80/20; v/v) mixture. The unreacted ester elutes the expected acid which is then recrystallized from DCM/isopropyl ether.

M.p.=232°-234° C.
$\alpha_D^{26}=-254$ (c=0.3; chloroform).

EXAMPLES 29a AND 29b 2-((2S)-2-Carbamoylpyrrolidinocarbonyl)-5-chloro-3-(2-chlorophenyl)-1-(3,4-dimethoxyphenylsulfonyl)-3-hydroxyindoline, (cis isomerism: 2 compounds)

230 mg of the compound prepared in Example 2a are dissolved in 5 ml of DCM, 50 mg of DIPEA and then 165 mg of BOP are added and the mixture is left for 5 minutes at RT. The mixture is cooled in an ice bath and a stream of gaseous ammonia is then bubbled through for 1 minute and, after 15 minutes, for a further 1 minute. Water and then a large volume of ethyl acetate are added in order to obtain two phases. The organic solution is washed with a sodium carbonate solution, water, a potassium hydrogensulfate solution, water and then saline water. After drying, the residue is chromatographed on silica by eluting with a DCM/MeOH (93/7; v/v) mixture. The product obtained is triturated in a DCM/isopropyl ether/hexane mixture. It contains 1/3 mole of isopropyl ether.

$\alpha_D^{26}-189$ (c=0.23; chloroform).

The compound of Example 29a can be prepared according to another procedure.

A)
2′,5-Dichloro-2-[N-(3,4-dimethoxyphenylsulfonyl)-N-((2S-2-carbamoylpyrrolidinocarbonylmethyl)-]aminobenzophenone 33.9 g of the acid prepared in Example 10a-11a, Step A are dissolved in 300 ml of chloroform. 15 g of thionyl chloride are added and the mixture is brought to reflux for 1 hour and a half. The mixture is evaporated to dryness, the residue is then taken up in DCM and evaporated again. The mixture is dissolved in 300 ml of DCM, brought to 0° C. and 10.5 g of (L)-prolinamide hydrochloride are added, and then 18 g of DIPEA in 20 ml of DCM are slowly added without allowing the temperature of the reaction mixture to exceed 3° C. After one night at DCM are slowly added without allowing the temperature of the reaction mixture to exceed 3° C. After one night at RT, the reaction mixture is washed with sodium bicarbonate (2 times) and then with potassium hydrogensulfate (2 times); the reaction mixture is dried and concentrated. The crude product obtained is dissolved in the minimum amount of DCM and added dropwise to isopropyl ether (1.2 1) with stirring. After stirring for 2 hours, the precipitate obtained is filtered and then dried under vacuum for 6 hours at 60° C. 42 g are collected.

$\alpha_D^{25}=-40.8$ (c=1.007; chloroform).

B)
2-((2S)-2-Carbamoylpyrrolidinocarbonyl)-5-chloro-3-(2-chlorophenyl)-1-(3,4-dimethoxyphenylsulfonyl)-3hydroxyindoline, (cis isomerism: 2 compounds)

5 g of the product prepared in the preceding step are dissolved in 50 ml of methanol. The solution is cooled to −10° C.; 1.35 g of DBU is added and the mixture is maintained for 60 hours at −10° C. A compound crystallizes; it is filtered (cis compound 1). The crystallization liquors are neutralized with KHSO$_4$ and the mixture is evaporated to dryness. It is taken up in water, extracted 2 times with DCM, and the extracts are dried and concentrated. The crude product obtained is chromatographed on silica by eluting with an AcOEt/DCM (28/72; v/v) mixture. A mixture is collected which is dissolved in the minimum amount of methanol while hot; the insoluble material is filtered off the liquors are then placed overnight at −4° C. and the cis compound 2 crystallizes.

m=1.25 g.
$\alpha_D^{25}=-196$ (c=0.351; chloroform).

The analysis of the NMR spectrum shows the presence of one mole of MeOH per mole of product. The recrystallization of the product from ethanol makes it possible to remove the solvent in the crystals.

M.p.=154°-162° C.
$\alpha_D^{25}=-204$ (c=0.3; chloroform).
$\alpha_D^{25}=-131$ (c=0.27; chloroform/methanol: 8/2: v/v)

This compound is identical, the solvent excepted, to that prepared by the first procedure of the present example.

The compound which crystallized in Step B) above, called cis compound 1, is recrystallized from methanol.

M.p.=190° C.
$\alpha_D=+115$ (c=0.3; chloroform).

EXAMPLE 30a

5-Chloro-3-(2-chlorophenyl)-1-(3,4-dimethoxyphenylsulfonyl)-3-hydroxy-2-[(2S)-2-(hydroxymethyl)pyrrolidinocarbonyl]indoline, cis isomerism

A)
2′,5-Dichloro-2-[N-(3,4-dimethoxyphenylsulfonyl)-N-(2-(hydroxymethyl)pyrrolidinocarbonylmethyl)-]aminobenzophenone This compound is obtained by reacting (L)-prolinol with the acid prepared in Example 10a-11a, Step A, by following the usual procedure.

B)
5-Chloro-3-(2-chlorophenyl)-1-(3,4-dimethoxyphenylsulfonyl)-3-hydroxy-2-[(2S)-2-(hydroxymethyl)pyrrolidinocarbonyl]indoline, cis isomer 1.5 g of the compound of the preceding step is cyclized in the presence of 380 mg of DBU in 2 ml of DCM. After 3 days at RT, 1 ml of DCM is added and the mixture is then heated at 40° C. overnight. The formation of 3 major compounds is observed by TLC on silica (eluent AcOEt).

The least polar fraction is eluted by chromatography on Silica using DCM/AcOEt (60/40 to 80/20; v/v). A chromatography on alumina is then carried out by eluting with DCM/MeOH (99/1; v/v). The fraction obtained is homogeneous by TLC. The product is recrystallized three times from DCM/isopropyl ether. The expected product is obtained with an HPLC purity greater than 99%.

m=155 mg.
M.p.=194°-197° C.
$\alpha_D^{25}=-195$ (c=0.2; chloroform).

SYNTHESES in the (D)-Proline series: Example 31a

EXAMPLE 31a

5-Chloro-3-(2-chlorophenyl)-1-(3,4-dimethoxyphenyl-sulfonyl)-3-hydroxy-2-[(2R)-2-(methoxycarbonyl)pyrrolidinocarbonyl]indoline, cis isomer

A)
2′,5-Dichloro-2-[N-(3,4-dimethoxyphenylsulfonyl)-N-((2R)-2-(methoxycarbonyl)pyrrolidinocarbonylmethyl)]-aminobenzo-phenone This compound is obtained from the acid prepared in Example 10a–11a, Step A (3 g) to which are added 1.2 g of methyl (D)-prolinate and 2.8 g of BOP in 10 ml of DCM in the presence of 1.15 g of triethylamine. The mixture is left for 1 hours at RT and is then diluted with DCM, the organic phase is washed with sodium carbonate and with potassium hydrogensulfate, dried and concentrated. The crude product is chromatographed on silica, eluting with a DCM/AcOEt (95/5; v/v) mixture. The product obtained is then recrystallized from a DCM/isopropyl ether mixture.

M.p. = 140°–141° C.
$\alpha_D^{25} = +28.5$ (c=0.27; chloroform).

B)
5-Chloro-3-(2-chlorophenyl)-1-(3,4-dimethoxyphenyl-sulfonyl)-3-hydroxy-2-[(2R)-2-(methoxycarbonyl)pyrrolidinocarbonyl]indoline, cis isomer 1.5 g of the preceding compound is brought to reflux overnight in 5 ml of DCM in the presence of 360 mg of DBU. The mixture is chromatographed on alumina. The mixture DCM/AcOEt (95/5; v/v) elutes the least polar fraction (m=300 mg) which is recrystallized 2 times in a DCM/isopropyl ether mixture.

M.p. = 186°–188° C.
$\alpha_D^{25} = +245$ (c=0.4; chloroform).

This compound is the enantiomer obtained from (D)proline of that described in Example 27.

EXAMPLES 32a AND 32b

N-Methyl-N-methoxycarbonylmethyl-5-chloro-3-(2-chlorophenyl)-1-(4-ethoxyphenylsulfonyl)-3-hydroxy-2-indolinecarboxamide, trans isomer and cis isomer

A)
2′,5-Dichloro-2-[N-(4-ethoxyphenylsulfonyl)-N-(N′-methyl-N′-(methoxycarbonylmethyl)carbamylmethyl)]aminobenzophenone 5.7 g of 2′,5-dichloro-2-(4-ethoxyphenylsulfonamido)benzophenone are dissolved, under argon, in 40 ml of DMF and 400 mg of 80% sodium hydride are added at 0° C.; after 15 minutes, 4.3 g of methyl N-(bromoacetyl)sarcosinate are added. After 48 hours, the expected product is extracted in the usual way and is then purified by chromatography on silica by eluting with DCM/AcOEt (90/10; v/v) and recrystallizing in a DCM/isopropyl ether mixture.

M.p. = 158°–160° C.

B)
N-Methyl-N-methoxycarbonylmethyl-5-chloro-3-(2-chlorophenyl)-1-(4-ethoxyphenylsulfonyl)-3-hydroxy-2-indolinecarboxamide, trans isomer 1 g of the compound obtained in the preceding step is dissolved in 4 ml of DCM and treated for 90 minutes at RT with 312 mg of TBD. A solution of potassium hydrogensulfate is added, the DCM is evaporated under vacuum, the mixture is extracted with AcOEt and the extract is washed and dried over magnesium sulfate. The expected product is obtained by chromatography on silica gel by eluting with DCM/AcOEt (90/10; v/v).
m=590 mg.
M.p. = 168°–171° C. after recrystallizing from DCM/hexane.

C)
N-Methyl-N-methoxycarbonylmethyl-5-chloro-3-(2-chlorophenyl)-1-(4-ethoxyphenylsulfonyl)-3-hydroxy-2-indolinecarboxamide, cis isomer 2.96 g of the compound obtained in Step A are suspended in 20 ml of methanol and 10 ml of THF; 100 mg of sodium methylate are added and the mixture is then left for 7 hours in the refrigerator. Water is added, the mixture neutralized with a potassium hydrogensulfate solution and a part of the methanol is evaporated under vacuum. After extracting with AcOEt, the residue is chromatographed on alumina and is then eluted with a DCM/AcOEt (80/20; v/v) mixture. 850 mg of the expected product are obtained which are recrystallized from a DCM/isopropyl ether mixture.

Figure 6:
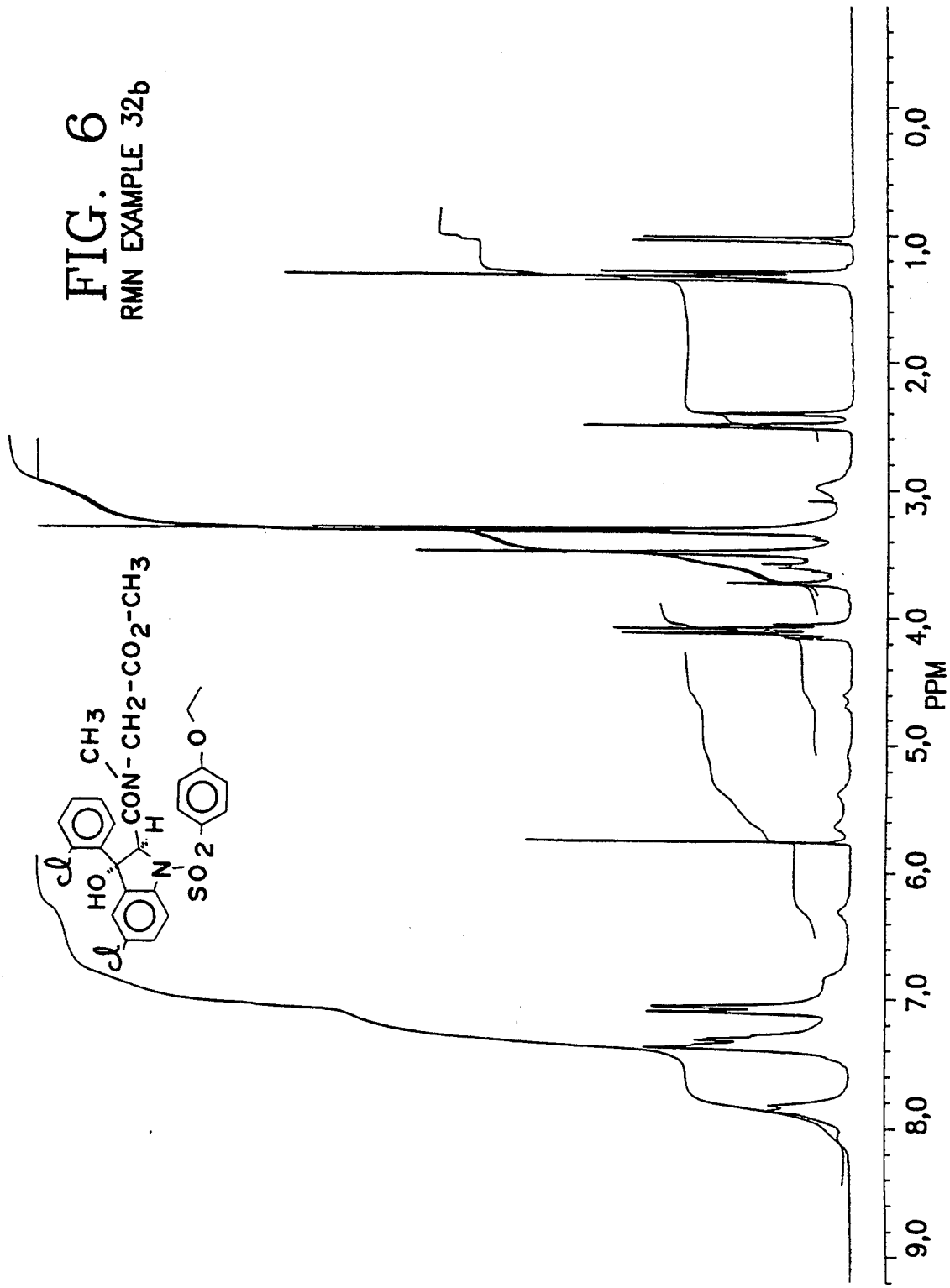
FIG. 6 is the nuclear magnetic resonance spectrum of the compound of Example 32b.

The NMR spectrum is given in FIG. 6.

By using methods similar to those described above, intermediate compounds (VI)′ for the synthesis of compounds (I)′ according to the invention were prepared.

The compounds (VI)′ prepared are described in Table 1A below.

The compounds (I)′ prepared are described in Table 2A below.

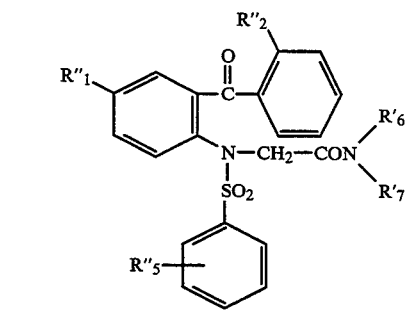

TABLE 1A

| | | | −N⟨$^{R'_6}_{R'_7}$ | |
|---|---|---|---|---|
| R″₁ | R″₅ | R″₂ | R′₇ | M.p. (°C.) or IR Solvent |
| Br— | 3,4-CH₃O | F— | CH₃<br>\|<br>—N—CH₂CO₂CH₂C₆H₅ | 82–83<br>DCM/isopropyl ether |

TABLE 1A-continued

| R"1 | R"5 | R"2 | $-N\binom{R'_6}{R'_7}$ | M.p. (°C.) or IR Solvent |
|---|---|---|---|---|
| Cl— | 3,4-CH₃O | Cl— | —N(CH₃)—CH₂CH₂CO₂CH₃ | 164–166 DCM/isopropyl ether |
| Cl— | 3,4-CH₃O | Cl— | —N(CH₃)—CH₂CH₂N(Et)—Et | 128 DCM/isopropyl ether |
| Cl— | 3,4-CH₃O | Cl— | —N(Et)—CH₂CH₂CO₂CH₃ | 105 DCM/isopropyl ether |
| Cl— | 2,4-CH₃O | Cl— | —N(piperazine)N—CO₂CH₂C₆H₅ | 142–143 MeOH |
| CH₃O— | 3,4-CH₃ | Cl— | —N(Et)—CH₂CH₂CO₂CH₃ | IR (1) |
| Cl— | 3,4-CH₃O | Cl— | —N(iPentyl)—CH₂CH₂CO₂CH₃ | 85 Isopropyl ether/DCM |
| Br— | 3,4-CH₃O | Cl— | —N(Et)—CH₂CH₂CO₂CH₃ | IR (2) |
| Cl— | 3,4-CH₃O | Cl— | —N(thiomorpholine)S | 199 DCM/isopropyl ether |
| Cl— | 3,4-CH₃O | Cl— | N(Pr)—CH₂CO₂CH₃ | 135 Isopropyl ether/ DCM/AcOH |
| Cl— | 3,4-CH₃O | Cl— | N(Pr)—CH₂CH₂—CO₂CH₃ | 113 DCM/isopropyl ether |
| Cl— | 3,4-CH₃O | Cl— | —N(Et)—CH₂—CO₂CH₃ | 160 isopropyl ether |
| Cl— | 3,4-CH₃O | Cl— | azetidinyl—NH—CO₂-tBu | 197–198 |
| Cl— | 3,4-CH₃O | Cl— | —N⟨—CO₂CH₂C₆H₅ | (3) |

IR (1) (DCM) 1740 cm⁻¹ fine  1680 cm⁻¹ broad
IR (2) (DCM) 1735 cm⁻¹ fine  1660–1680 cm⁻¹ split (3) This compound is characterized by its optical rotation:
$\alpha_D^{25} = -36.8$ (c = 0.44; chloroform).

TABLE 2A

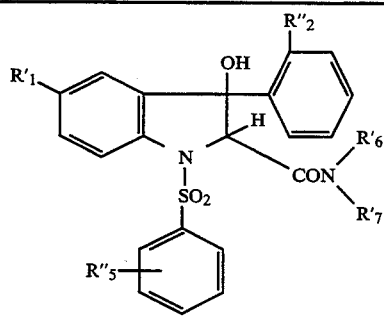

For each compound of formula (I)' which has the
substituents R'$_1$, R"$_5$, R"$_2$ and NR'$_6$R'$_7$ of the table below,
the cis isomerism is shown and then the trans isomerism,
except when otherwise indicated.

| Example | R'$_1$ | R'$_5$ | R'$_2$ | $-N\begin{smallmatrix}R_6\\R_7\end{smallmatrix}$ | M.p. (°C.) or NMR Solvent |
|---|---|---|---|---|---|
| 33a | Br— | 3,4-CH$_3$O | F— | CH$_3$<br>\|<br>—N—CH$_2$CO$_2$CH$_2$C$_6$H$_5$ | 87–95 |
| 34a | | | | | NMR |
| 35a | Cl— | 3,4-CH$_3$O | Cl— | CH$_3$<br>\|<br>—N—CH$_2$CH$_2$CO$_2$CH$_3$ | 100–103 |
| 36a | | | | | 154–157<br>DCM/isopropyl ether |
| 37a cis | Cl— | 3,4-CH$_3$O | Cl— | CH$_3$<br>\|<br>—N—CH$_2$CH$_2$CO$_2$H | 140–144<br>DCM/isopropyl ether |
| 38a mixture | Cl— | 3,4-CH$_3$O | Cl— | CH$_3$   Et<br>\|   \|<br>—N—CH$_2$CH$_2$N—Et | 222–225<br>DCM/isopropyl ether |
| 39a | Cl— | 3,4-CH$_3$O | Cl— | Et<br>\|<br>—N—CH$_2$CH$_2$CO$_2$CH$_3$ | NMR |
| 40a | | | | | NMR |
| 41a cis | Cl— | 3,4-CH$_3$O | Cl— | Et<br>\|<br>—N—CH$_2$CH$_2$CO$_2$H | 166<br>DCM/isopropyl ether |
| 42a | Cl— | 3,4-CH$_3$O | Cl— | —N⟨piperidine⟩—N(CH$_3$)$_2$ | 119<br>AcOEt/isopropyl ether |
| 43a | | | | | 228<br>MeOH |
| 44a cis | Cl— | 3,4-CH$_3$O | Cl— | CH$_2$C$_6$H$_5$   CH$_3$<br>\|   /<br>—N—CH$_2$CH$_2$N<br>  \\<br>  CH$_3$ | 179<br>DCM/isopropyl ether |
| 45a | Cl— | 3,4-CH$_3$O | Cl— | —N⟨piperazine⟩N—CH$_2$CO$_2$Et | 109<br>DCM/isopropyl ether |
| 46a | | | | | 196<br>DCM/isopropyl ether |
| 47a | Cl— | 2,4-CH$_3$O | Cl— | —N⟨piperazine⟩N—CO$_2$CH$_2$C$_6$H$_5$ | 134 (iPr)$_2$O |
| 48a | | | | | 195<br>DCM/isopropyl ether |
| 49a cis | Cl— | 3,4-CH$_2$O | Cl— | Et<br>\|<br>—N—CH$_2$CH$_2$CONH$_2$ | 236<br>isopropyl ether |
| 50a | CH$_3$ | 3,4-CH$_3$ | Cl— | Et<br>\|<br>—N—CH$_2$CH$_2$CO$_2$CH$_3$ | 154<br>isopropyl ether |
| 51a | | | | | 87<br>isopropyl ether |

TABLE 2A-continued

| | | | | | |
|---|---|---|---|---|---|
| 52a | Cl— | 2,4-CH₃O | Cl— | 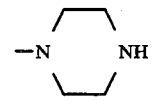 | 194<br>MeOH/isopropyl ether |
| 53a<br>cis | Cl— | 3,4-CH₃O | Cl— | iPentyl<br>\|<br>—N—CH₂CH₂CO₂CH₃ | 195<br>isopropyl ether/DCM |
| 54a<br>55a | Br—<br> | 2,4-CH₃O | Cl— | Et<br>\|<br>—N—CH₂CH₂CO₂CH₃ | 138–140<br>isopropyl ether<br>140<br>isopropyl ether |
| 56a<br>57a | Cl— | 3,4-CH₃O | Cl— | 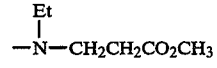 | 242–245<br>DCM/isopropyl ether<br>225<br>MeOH/isopropyl ether |
| 58a<br>58b | Cl— | 2,4-CH₃O | Cl— | 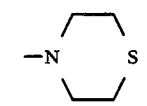 | 228<br>MeOH/isopropyl ether<br>221<br>DCM/MeOH |
| 59a<br>59b | Cl— | 3,4-CH₃O | Cl— | Et<br>\|<br>—N—CH₂CH₂CH₂CO₂CH₃ | 131–134<br>DCM/isopropyl ether/hexane<br>121<br>DCM/ether/hexane |
| 60a<br>61a | Cl— | 3,4-CH₃O | Cl— | iBu<br>\|<br>N—CH₂CH₂CO₂CH₃ | 162–166<br>DCM/isopropyl ether<br>130<br>DCM/isopropyl ether/hexane |
| 62a<br>63a | Cl— | 3,4-CH₃O | Cl— | Pr<br>\|<br>—N—CH₂CO₂CH₃ | 176<br>isopropyl ether/DCM<br>NMR |
| 64a<br>65a | Cl— | 3,4-CH₂O | Cl— | Pr<br>\|<br>—N—CH₂CH₂CO₂CH₃ | 148<br>isopropyl ether/DCM<br>122<br>isopropyl ether/DCM |
| 66a<br>67a | Cl— | 3,4-CH₃O | Cl— | Et<br>\|<br>N—CH₂CO₂CH₃ | NMR<br>168<br>isopropyl ether |
| 68a<br>cis | Cl— | 3,4-CH₃O | Cl— | iBu<br>\|<br>N—(CH₂)₂CO₂H | 179–182<br>DCM/isopropyl ether |
| 69a<br>cis | Cl— | 3,4-CH₃O | Cl— | Et<br>\|<br>N—CH₂CO₂H | 139<br>DCM/isopropyl ether |
| 70a<br>cis | Cl— | 3,4-CH₃O | Cl— | Pr<br>\|<br>N—CH₂CO₂H | 130<br>isopropyl ether |
| 71a<br>cis | Cl— | 3,4-CH₃O | Cl— | Et<br>\|<br>N—(CH₂)₃CO₂H | 136<br>DCM/isopropyl ether |
| 72a<br>cis | Cl— | 3,4-CH₃O | Cl— | Et<br>\|<br>N—CH₂—CONH₂ | 135<br>DCM/isopropyl ether |
| 73a<br>74a | Cl— | 3,4-CH₃O | Cl— | 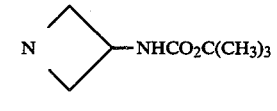 | 197<br>MeOH/isopropyl ether<br>211<br>MeOH |
| 75a<br>cis | Cl— | 3,4-CH₃O | Cl— | 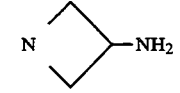 | NMR |

TABLE 2A-continued

| | | | | | |
|---|---|---|---|---|---|
| 76a cis | Cl— | 3,4-CH₃O | Cl— | (piperidine-NH₂ structure) | Fumarate 152–156 DCM/isopropyl ether |
| 76b 76c | Cl— | 3,4-CH₃O | Cl— | (indoline-CO₂CH₂C₆H₅ structure) | 137 isopropyl ether/MeOH/hexane 183–185 hexane |

EXAMPLE 34a

Analysis: calculated C:55.54; H: 4.24; N:3.93. Found C: 55.72; H: 4.57; N: 3.83.

NMR spectra at 200 MHz (DMSO: 2.5 ppm)

Figure 5:
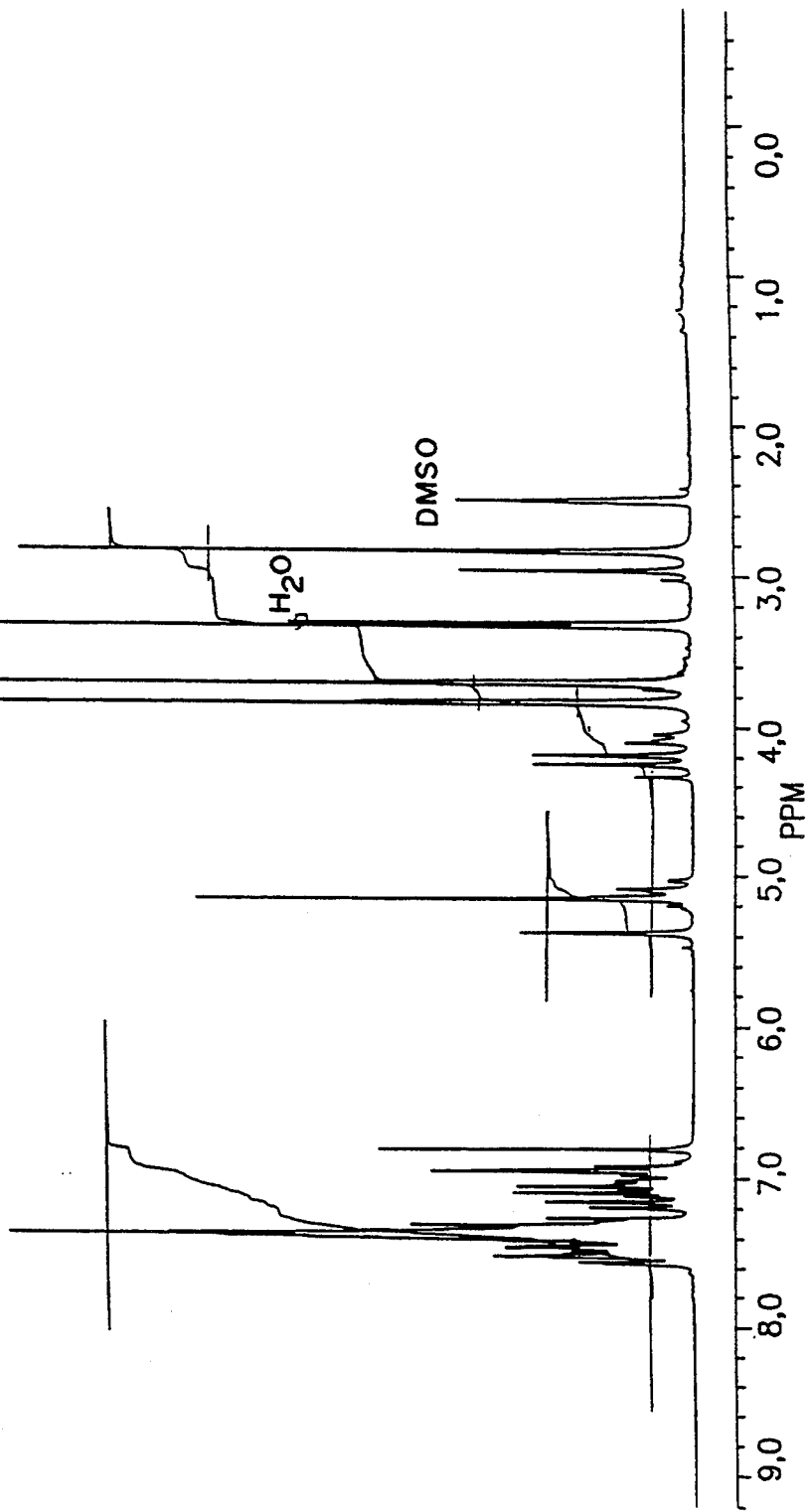

EXAMPLE 34a: FIG. 5

EXAMPLE 38a 0.7–1.1 ppm: m:6H:2CH₃(Et)
2–4 ppm:m:17H:2CH₂(Et), 2C$\underline{H_2}$—N, N—C$\underline{H_3}$, 2OC$\underline{H_3}$
5.2–5.7 ppm:3s:1H:H (indoline)
6.2–8.2 ppm:m:11H:O$\underline{H}$+aromatics

EXAMPLE 39 a 0.3–1.2 ppm:m:3H:CH₃ (Et)
1.5–4.3 ppm:m:15H:C$\underline{H_2}$—CO, CH₂ (Et), C$\underline{H_2}$—N, 2OC$\underline{H_3}$, CO₂C$\underline{H_3}$
5.2–5.6 ppm:3s:1H: H (indoline)
6.2–8.2 ppm:m:11H:O$\underline{H}$+aromatics

EXAMPLE 40a 0.8–1.1 ppm:m:3H:CH₃ (Et)
2.2–3.9 ppm:m:15H:CH₂CO, CH₂(Et), CH₂N, CO₂CH₃, 2OCH₃
5.3–5.7 ppm:2s:1H:H (indoline)
6.6–8.2 ppm:m:11H:O$\underline{H}$+aromatics

EXAMPLE 63a 0.4–1 ppm: split t:3H:CH₂—CH₂—C$\underline{H_3}$
5 ppm:m:2H:C$\underline{H_2}$—CH₂—CH₃
2.5–4.4 ppm:m:13H:C$\underline{H_2}$—CH₂—CH₃, NC$\underline{H_2}$COOCH₃, 2OC$\underline{H_3}$
5.2–5.8 ppm; bs:1H:H (indoline)
6.5–8.3 ppm:m:11H:O$\underline{H}$+aromatics

EXAMPLE 66a 0 to 1.5 ppm:m:3H:CH₂—C$\underline{H_3}$
2.3–5.8 ppm:m:14H:C$\underline{H_2}$—CH₃, NC$\underline{H_2}$COOC$\underline{H_3}$, 2OC$\underline{H_3}$, H (indoline)
6.1–8.3 ppm:m:11H:O$\underline{H}$+aromatics

EXAMPLE 75a 1.95 ppm:bs:2H:NH₂
2.7 to 5.3 ppm:m:12H:2OCH₃, 2NCH₂, H(indoline), CHNH₂
6 to 8.3 ppm:m:11H:O$\underline{H}$+aromatics

EXAMPLE 76b $\alpha_D^{25} = +102$ (c=0.35; chloroform)

EXAMPLE 76c $\alpha_D^{25} = -158$ (c=0.2; chloroform).

Some compounds according to the invention described in Table 2 are useful in the preparation of other compounds according to the invention. For example, compound 41a was obtained from compound 39a by treatment in basic medium in methanol MeOH/H₂O. Compound 49a was prepared from compound 41a by treatment with aqueous ammonia in the presence of DIPEA and BOP.

EXAMPLE 77a

N-Ethyl-N-(2-aminoethyl)-5-chloro-3-(2-chlorophenyl)-1-(3,4-dimethoxyphenylsulfonyl)-3-hydroxy-2-indolinecarboxamide, (cis isomerism)

500 mg of compound 49a are dissolved in 10 ml of acetonitrile and 10 ml of water and 252 mg of pyridine and 380 mg of bis(trifluoroacetoxy)iodobenzene are added. After stirring for 2 hours, the mixture is taken up in a solution of hydrochloric acid, extracted with ether, alkalized with dilute sodium hydroxide solution, extracted with DCM and the extract is dried and concentrated. An oil is obtained and the expected product then crystallizes from ether.

m=150 mg.
M.p.=164° C.

EXAMPLE 78a

N-Ethyl-N-[(1S)-1-(ethoxycarbonyl)ethyl ]-5-chloro-3-(2-chlorophenyl )
-1-(3,4-dimethoxyphenylsulfonyl)
-3-hydroxy-2-indolinecarboxamide, (cis isomerism)

A) N-[2-(2-Chlorophenylcarbonyl)-5-chlorophenyl ]-N-(3,4-dimethoxyphenylsulfonyl )glycine acid chloride A mixture containing 11 g of the acid prepared in Example 10a–11a, Step A) and 5 g of thionyl chloride in 10 ml of chloroform is heated for 1 hour at 60° C. The mixture is left to return to RT, concentrated under vacuum and the residue taken up in DCM (2 times). A yellow oil is obtained which is used as it is in the following step.

IR: 1800 cm⁻¹, (C=O).

B)
2',5-Dichloro-2-[N-(3,4-dimethoxyphenylsulfonyl)-N-(N'-ethyl-N'-((1S)
-1-(ethoxycarbonylethyl)ethoxycarbamoylmethyl)
]aminobenzophenone The preparation of this compound was carried out according to J. Org. Chem., 1985, 50, 945–950.

5.15 g of (L)-Boc(N-Et)AlaOEt is treated with 10 ml of TFA at 0° C. in order to remove the Boc group. The mixture is concentrated under vacuum, taken up in 20 ml of DCM, cooled to −78° C. and 2 equivalents of TEA and the acid chloride prepared in the preceding step, dissolved in DCM, are added. After 18 hours at RT, the mixture is extracted with DCM, the extract is washed with water and then chromatographed on silica by eluting with a DCM/AcOEt (90/10; v/v) mixture. The expected product crystallizes from isopropyl ether.
M.p.=112° C.
m=8 g.

C)
N-Ethyl-N-[(1S)-1-(ethoxycarbonyl)ethyl]-5-chloro-3-(2-chlorophenyl)-1-(3,4-dimethoxyphenylsulfonyl)-3-hydroxy-2-indolinecarboxamide, (cis isomerism)

The compound obtained in the preceding step is stirred at RT for 18 hours in 10 ml of THF and 20 ml of ethanol, in the presence of 1.46 g of DBU. The mixture is concentrated under vacuum, the residue is taken up in DCM, washed with water, concentrated and the product chromatographed on alumina by eluting with AcOEt/DCM (10/90; v/v).
NMR
0–0.9 ppm: split d:3H:CH—CH$_3$
0.9–1.7 ppm:m:6H:2CH$_3$ (ethyl)
2.6 to 5.8 ppm:m:12H:2OCH$_3$, NCH$_2$, OCH$_2$, NCH, COCH
6.1 to 8.3 ppm:m:11H:OH—10H aromatics

EXAMPLES 79a AND 80a

N,N-Di[2-(methoxycarbonyl)ethyl]-5-chloro-3-(2-chlorophenyl)-1-(3,4-dimethoxyphenylsulfonyl)-3-hydroxy-2-indolinecarboxamide, cis isomer and trans isomer

A) N,N-Di[2-(methoxycarbonyl)ethyl]benzylamine

Preparation according to J. Am. Chem. Soc., 1950, 72, 3298.

107 g of benzylamine in 200 ml of ethanol are cooled in an ice bath and 172.2 g of methyl acrylate in 250 ml of ethanol are slowly added. After 13 days at RT, the solvent is evaporated under vacuum and a part of the oily residue is then distilled.
B.p.=135°–140° C. at 0.6 mm Hg.
m=30 g.
IR: 1730 cm$^{-1}$.

B) N,N-Di[2-(methoxycarbonyl)ethyl]amine 27.9 g of the amine obtained in the preceding step, placed in 500 ml of methanol, are mixed with 3 g of 5% palladium on charcoal and are treated under hydrogen pressure for 1 hour. The mixture is filtered on Celite ®, rinsed with methanol and the solvent evaporated under vacuum; the residual oil is used as it is in the following step.

C) N,N-Di[2-(methoxycarbonyl)ethyl]bromoacetamide

A mixture containing 14.3 g of the amine prepared in the preceding step, 100 ml of DCM and 10.6 ml of TEA is cooled in an ice bath; 15.3 g of bromoacetyl bromide are added dropwise and the mixture is then left stirring for 48 hours at RT. The mixture is extracted with DCM, the extract is washed with water and then a chromatography is carried out on silica by eluting with a DCM/MeOH (97/3; v/v) mixture. The expected product is obtained in the form of an oil.
m=15.9 g.
IR: 1650 cm$^{-1}$ and 1730 cm$^{-1}$.

D)
2′,5-Dichloro-2-[N-(3,4-dimethoxyphenylsulfonyl)-N-[N′,N′-di(2-(methoxycarbonyl)ethyl)carbamoylmethyl]]-aminobenzo-phenone 14.3 g of 2′,5-dichloro-2-(3,4-dimethoxyphenylsulfonamido)benzophenone are placed in 180 ml of DMF and 1.1 g of sodium hydride are added in portions. After stirring for 1 hour at RT, the mixture is cooled in an ice bath and 14.3 g of the product prepared in the preceding step are added and the mixture is left stirring for 72 hours at RT. The mixture is extracted with DCM, the extract is washed with water and then chromatographed on silica by eluting with a DCM/AcOEt (93/7; v/v) mixture.
m=28.4g.
M.p.=130° C.

E) N,N-Di[2-(methoxycarbonyl)ethyl]-5-chloro-3-(2-chlorophenyl)-1-(3,4-dimethoxyphenylsulfonyl)-3-hydroxy-2-indolinecarboxamide, cis isomer 12 g of the compound prepared in the preceding step and 0.930 g of sodium methylate in 150 ml of methanol are mixed at 0 ° C. and the mixture is then left stirring overnight at RT. The reaction mixture is neutralized by addition of 5% KHSO$_4$ and the solvent is then evaporated under vacuum. The residue is chromatographed on alumina by eluting with a DCM/AcOEt (8/2; v/v) mixture. 2.4 g of the expected product are recovered which are crystallized from methanol.
M.p.=175° C.

F) N,N-Di[2-(methoxycarbonyl)ethyl]-5-chloro-3-(2-chlorophenyl)-1-(3,4-dimethoxyphenylsulfonyl)-3-hydroxy-2-indolinecarboxamide, trans isomer The chromatography of the preceding step is continued and elution is carried out with a DCM/MeOH (9.5/0.5; v/v) mixture. 1.82 g of the trans isomer is obtained which crystallizes from isopropyl ether.
M.p.=85° C.

EXAMPLES 81a, 82a AND 83a 2-((2R)-2-Carbamoylthiazolidinocarbonyl)-5-chloro-3-(2-chlorophenyl)-1-(3,4-dimethoxyphenylsulfonyl)-3-hydroxyindoline, (cis isomerism: 2 compounds and trans isomerism)

A) (L)-4-Thiazolidinecarboxamide

This compound is prepared according to J. Med. Chem., 1981, 24, 692.

B)
2′,5-Dichloro-2-[N-(3,4-dimethoxyphenylsulfonyl)-N-((2R)-2-carbamoylthiazolidinocarbonylmethyl)]-aminobenzophenone This compound is obtained by the usual methods from the acid prepared in Example 10a–11a, Step A).
M.p.=125° C. after crystallizing from ether.

C)
2-((2R)-2-Carbamoylthiazolidinocarbonyl)-5-chloro-3-(2-chlorophenyl)-1-(3,4-dimethoxyphenylsulfonyl)-3hydroxyindoline 4.3 g of the product obtained in Step B) are cyclized in 90 ml of MeOH at RT in the presence of 1 g of DBU. The mixture is concentrated, the residue is taken up in water and DCM, the layers are separated, the organic layer is washed with KHSO$_4$ and then dried and concentrated. The residue is chromatographed on alumina by eluting with DCM/MeOH (97/3; v/v). The compound is obtained in the cis form (mixture of 2 diastereoisomers): 1.5 g, and then in the trans form (mixture of 2 diastereoisomers): m=1 g.

a) The cis fraction is crystallized from MeOH/DCM in order to obtain cis compound 1.

M.p.=176° C. after crystallizing from isopropyl ether.

$\alpha_D$= +57 (c=0.1; chloroform).

b) The crystallization liquors of the preceding product are chromatographed on silica by eluting with AcOEt/DCM (30/70; v/v). The cis compound 2 obtained is recrystallized from ether.

M.p.=205° C.

$\alpha_D$= −185 (c=0.3; chloroform).

c) The trans fraction (mixture of 2 diastereoisomers) is recrystallized from isopropyl ether.

M.p.=170° C.

EXAMPLES 84a, 85a, 86a AND 86b

5-Chloro-3-(2-chlorophenyl)-1-(3,4-dimethoxyphenylsulfonyl)-3-hydroxy-2-[(2S)-2-(N,N-dimethylthiocarbamoyl)pyrrolidinocarbonyl]indoline, cis isomerism (2 compounds), (trans isomerism: 2 compounds)

A) (L)-(N'-Boc)-N,N-Dimethylprolinethioamide

This compound is prepared according to J. Med. Chem., 1989, 2178.

2.36 g of (N'-Boc)-N,N-dimethylprolinamide are heated in anhydrous toluene under argon at 80° C. for 4 hours in the presence of 2.3 g of Lawesson's reagent. After 24 hours, the solvent is evaporated and isopropanol is added. The precipitate formed is separated, the isopropanol is evaporated and the residue is chromatographed on silica by eluting with hexane/AcOEt (30/70; v/v). The product obtained is recrystallized while cold from DCM/isopropyl ether (30/70; v/v).

M.p.=62° C.

B)
2',5-Dichloro-2-[N-(3,4-dimethoxyphenylsulfonyl)-N-((2S)-2-(N',N'-dimethylthiocarbamoyl)pyrrolidinocarbonylmethyl)]aminobenzophenone 3 g of the product prepared in the preceding step are dissolved in 10 ml of DCM and treated at 0° C. for 2 hours with 10 ml of TFA. The mixture is evaporated to dryness, then 20 ml of DCM and 6.1 g of the acid prepared in Example 10–11, Step A) are added at 0° C. and the mixture is neutralized with 3 g of DIPEA. 5.15 g of BOP are dissolved in 30 ml of DCM and this solution is added to the preceding solution at 0° C. over 30 minutes; the pH is maintained at neutral by the addition of DIPEA and the mixture is left stirring for 3 hours at 0° C. After one night at RT, the mixture is extracted in the usual way and then chromatographed on silica by eluting with DCM/AcOEt (85/15; v/v). The product obtained is recrystallized from isopropyl ether.

M.p.=182°–185° C.

$\alpha_D$= −72° (c=0.32; chloroform).

C)
5-Chloro-3-(2-chlorophenyl)-1-(3,4-dimethoxyphenylsulfonyl)-3-hydroxy-2-[(2S)-2-(N,N-dimethylthiocarbamoyl)pyrrolidinocarbonyl]indoline (cis isomerism: 2 compounds, and trans isomerism: 2 compounds)

3.8 g of the compound obtained in the preceding step are dissolved in 10 ml of DCM and the mixture is heated at reflux for 36 hours in the presence of 850 mg of DBU.

The different isomers formed are separated by successive chromatographic runs on silica.

a) Using DCM/AcOEt (85/15; v/v), the expected compound is eluted first in the form of a mixture of 2 cis diastereoisomers. The least soluble diastereoisomer is crystallized 2 times from a DCM/isopropyl ether/methanol mixture and is then recrystallized from the minimum amount of DMF at 60° C. followed by addition of 2 volumes of ethanol.

M.p.=270° C.

$\alpha_D$= −278 (c=1; chloroform).

b) The crystallization liquors of the preceding mixture are taken up in and the second cis diastereoisomer crystallizes from a DCM/isopropyl ether mixture.

M.p.=249°–251° C.

$\alpha_D$= +42 (c=0.22; chloroform).

c) The chromatography fractions eluted last, as well as the crystallization mother liquors of fractions a) and b), are combined, and are chromatographed again on silica by eluting with hexane/AcOEt (20/80; v/v). Isolated first is a fraction which is recrystallized 3 times from a DCM/isopropyl ether mixture and an insoluble material is removed on a paper between each recrystallization. The trans isomer 1 is thus obtained.

M.p.=191–193.

$\alpha_D$= +74.5 (c=0.2; chloroform).

d) The second fraction contains trans isomer 2 which is recrystallized from a DCM/isopropyl ether mixture and crystallizes with ⅓ mole of isopropyl ether.

M.p.=170° C.

$\alpha_D$= −266 (c=0.14; chloroform).

EXAMPLES 87a, 88a AND 89a 2-((2S)-2-Carbamoylpyrrolidinocarbonyl)-5-chloro-3-cyclohexyl-1-(3,4-dimethoxyphenylsulfonyl)-3-hydroxyindoline, (cis isomerism: 2 compounds, trans isomerism)

A)
5-Chloro-2-[N-(3,4-dimethoxyphenylsulfonyl)amino]-cyclohexylphenone

A solution of 35.6 g of 2-amino-5-chlorocyclohexylphenone and 39.5 g of 3,4-dimethoxyphenylsulfonyl chloride in 340 ml of pyridine is left stirring for 24 hours at RT. The solvent is evaporated under vacuum and the residue is then washed with water and with an acid solution (0.5N HCl). The expected product crystallizes from ethanol.

M.p.=135° C.

m=56.1 g.

B)
2-[(N-Benzyloxycarbonylmethyl-N-(3,4-dimethoxyphenylsulfonyl))amino]-5-chlorocyclohexylphenone 3.2 g of sodium hydride are added in portions to 52.6 g of the compound prepared in the preceding step in 520 ml of DMF and the mixture is left stirring for 1 hour at RT. After cooling in the ice bath, 21 ml of benzyloxycarbonylmethyl bromide are added dropwise and the mixture is left stirring for 24 hours at RT. The solvent is evaporated under vacuum and the residue is taken up in water. It is extracted with DCM and the extract is washed with water; the product obtained is used as it is in the following step.

C)

N-(5-Chloro-2-(cyclohexylcarbonyl)phenyl)-N-(3,4-dimethoxyphenylsulfonyl)glycine The compound obtained in the preceding step is placed with 3.9 g of 5% palladium on charcoal in 700 ml of acetic acid under hydrogen (1 atmosphere). At the end of the reaction, the palladium is filtered on Celite ® and rinsed with hot acetic acid; the solvent is evaporated under vacuum and the residue is taken up in water. It is extracted with DCM and the extract is washed with water and then with a concentrated NaHCO$_3$ solution. The residue obtained is chromatographed on silica by eluting with a DCM/MeOH (97/3; v/v) mixture. The expected product crystallizes from ethanol.

M.p.=160° C.

m=22.4 g.

D)

5-Chloro-2-[N-(3,4-dimethoxyphenylsulfonyl)-N-((2S)-2-carbamoylpyrrolidinocarbonylmethyl)]-aminocyclohexylphenone A mixture containing 9.92 g of the acid prepared in the preceding step, 3 g of (L)-prolinamide hydrochloride and 3.5 ml of DIPEA in 75 ml of DCM is cooled to 0° C. 8.84 g of BOP in solution in DCM are added and the pH is maintained at 7 by addition of DIPEA. The mixture is left stirring for 24 hours at RT. The mixture is extracted with DCM, and the extract washed with a saturated NaHCO$_3$ solution, a saline solution, a 5% KHSO$_4$ solution and again with a saline solution. The product is chromatographed on silica by eluting with a DCM/MeOH (96/4; v/v) mixture. The expected product solidifies in isopropyl ether.

M.p.=110° C.

m=7.3g.

$\alpha_D$=−53.9 (c=1; chloroform)

E)

2-((2S)-2-Carbamoylpyrrolidinocarbonyl)-5-chloro-3-cyclohexyl-1-(3,4-dimethoxyphenylsulfonyl)-3-hydroxyindoline, cis isomerism (2 compounds), trans isomerism 5.9 g of the compound prepared in the preceding step and 1.67 g of DBU are placed in 60 ml of methanol with stirring at 0° C. for 48 hours. The solvent is evaporated under vacuum, water is added, the mixture is extracted with DCM and the extract is then washed with a 5% KHSO$_4$ solution. The product is chromatographed on alumina by eluting with DCM/MeOH (98/2; v/v).

a) The least polar fraction contains the 2 cis isomers. This fraction is recrystallized from methanol. The first compound thus obtained (cis 1) is pure by HPLC.

M.p.=185° C.

By recrystallization of the mother liquors from MeOH, a second compound is obtained (cis 2). HPLC purity: 75% (it contains 25% cis 1 ) .

M.p.=132° C.

b) The most polar fraction contains the trans isomer in the form of an apparently single compound which is obtained by recrystallizing from methanol.

M.p.=240° C.

$\alpha_D$=−55.1 (c=1; chloroform) .

EXAMPLE 89b 2-((2S)-2-Carbamoylpyrrolidinocarbonyl)-5-chloro-3-cyclohexyl-1-(3,4-dimethoxyphenylsulfonyl)-3-hydroxyindoline, cis isomerism (2 compounds), trans isomerism By using a procedure similar to that described for Examples 87a, 88a and 89a, an analogous compound in the (D)proline series is prepared.

The compound obtained after crystallizing from a DCM/MeOH mixture has the trans configuration.

M.p.=238° C.

$\alpha_D$+164 (c=0.245; chloroform/methanol, 8.2, v/v).

The NMR spectrum of this compound and of that described in Step E b) of the preceding example are identical.

EXAMPLE 90a

5-Chloro-3-(2-chlorophenyl)-1-(3,4-dimethoxyphenylsulfonyl)-2-[(2S)-2-(N-methylaminocarbonyl)pyrrolidinocarbonyl]-3-hydroxyindoline, cis isomer 920 mg of the compound prepared in Example 28a are placed, with stirring, in 20 ml of DCM containing 371 mg of BOP for 15 minutes, a stream of monomethylamine is bubbled through for 10 minutes and the stirring is maintained for an additional 30 minutes. The mixture is taken up in water, the layers separated, the organic layer washed with potassium hydrogensulfate and with sodium carbonate, dried and concentrated. The residue is chromatographed on silica by eluting with DCM/methanol (97.5/2.5; v/v). The expected product is collected which crystallizes from an isopropyl ether/DCM mixture.

m=750 mg.

M.p.=158° C.

$\alpha_D$=−216 (c=0.3; chloroform).

By operating as in the previously described examples (Examples 27a to 31a and 90a) and by using derivatives of (L)-proline (except when otherwise indicated), other intermediate compounds (VI)′ for the synthesis of the compounds (I)′ according to the invention were prepared.

The compounds (VI)′ prepared are described in Table 3A below.

The Compounds (I)′ prepared are described in Table 4A below.

TABLE 3A

[Structure: 5-chloro-2-[N-(arylsulfonyl)]aminobenzophenone with 2-chlorobenzoyl group, connected via N–CH₂–CO–NR'₆R'₇; R''₅ on sulfonylphenyl]

| R''₅ | —N(R'₆)(R'₇) | M.p. (°C.) | $\alpha_D^{25}$ (chloroform) |
|---|---|---|---|
| 3,4-CH₃O | (D)—N pyrrolidine, H, CONH₂ | | +4.5 c = 1.015 |
| 3,4-CH₃O | —N pyrrolidine, H, COOCH₃ | 161–163 DCM/isopropyl ether | −70.8 c = 0.48 |
| 2,4-CH₃O | —N pyrrolidine, H, COOCH₃ | 145–148 | −17.5 c = 3.36 |
| 3,4-CH₃O | —N pyrrolidine, H, COOCH₂—C₆H₅ | ≃110 DCM/isopropyl ether | |
| 3,4-CH₃O | —N pyrrolidine, H, CH₂COOCH₃ | 148 isopropyl ether/MeOH | |

TABLE 4A

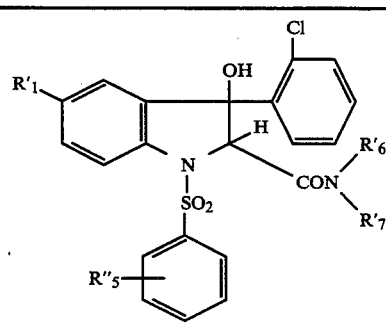

TABLE 4A-continued

| Example | R'$_1$ | R''$_5$ | -N(R'$_6$)(R'$_7$) | M.p. (°C.) | $\alpha_D^{25}$ (chloroform) |
|---|---|---|---|---|---|
| 91a cis 1 | Cl | 3,4-CH$_3$O | (D) pyrrolidine-CONH$_2$ | 115 MeOH | +188 c = 0.33 |
| 92a cis 2 | Cl | | | 204 MeOH/DMF | −114* c = 0.31 |
| 93a cis | Cl | 3,4-CH$_3$O | pyrrolidine-COOCH$_3$ | 198–201 DCM/isopropyl ether | |
| 94a cis | Cl | 2,4-CH$_3$O | pyrrolidine-COOCH$_3$ | 205–207 DCM/isopropyl ether | |
| 95a cis | Cl | 2,4-CH$_3$O | pyrrolidine-COOH | 221 DCM/isopropyl ether | −242 c = 0.254 |
| 96a cis | Cl | 3,4-CH$_3$O | pyrrolidine-COOCH$_2$-Ph | | −234 c = 0.32 |
| 97a cis | Cl | 3,4-CH$_3$O | pyrrolidine-CON(CH$_3$)$_2$ | | −214 c = 0.32 |
| 98a cis 1 | Cl | 3,4-CH$_3$O | pyrrolidine-CH$_2$COOCH$_3$ | 105–115 DCM/isopropyl ether | +174.6 c = 0.3 |
| 99a cis 2 | | | | 175 DCM/isopropyl ether | −214.6 c = 0.3 |
| 100a trans 1 | | | | 177 DCM/isopropyl ether | −155 c = 0.2 |
| 102a cis 1 | Cl | 3,4-CH$_3$O | pyrrolidine-CH$_2$COOH | 135 isopropyl ether | −162 |

TABLE 4A-continued

| Ex. | R | R' | Structure | mp | [α] |
|---|---|---|---|---|---|
| 103a cis 1 | Cl | 3,4-CH₃O | —N(pyrrolidine, H axial, CH₂CONH₂) | 145 DCM/isopropyl ether | −167 c = 0.4 |
| 103b cis 1 cis 2 | Cl | 3,4-CH₃O | —N(pyrrolidine, H, CH₂CONH₂) | | |
| 104a cis 1 | Cl | 3,4-CH₃O | —N(pyrrolidine, H axial, CH₂NH₂) | 210 ether | −177.5 c = 0.2 |
| 104b cis 1 cis 2 | Cl | 3,4-CH₃O | —N(pyrrolidine, H, CH₂NH₂) | | |
| 105a | CH₃O | 3,4-CH₃O | —N(pyrrolidine, H axial, CONH₂) | 200 EtOH | −195 c = 0.2 |
| 106a | | | | 215 MeOH c = 0.2 | +127 |
| 107a | CH₃O | 3,4-CH₃O | (D) —N(pyrrolidine, H, CONH₂) | 198 | −63.3 c = 0.117 (CHCl₃/MeOH) 8/2; v/v) |
| 108a | Cl | 2,4-CH₃O | —N(pyrrolidine, H axial, CONH₂) | 274 DCM/MeOH | −225 c = 0.372 (CHCL₃/MeOH 8/2; v/v) |
| 108b cis | Cl | 3,4-CH₃O | (D) —N(pyrrolidine, H axial, CONHOH) | | −198.7 c = 0.24 |

\*: Example 92a: Other measured optical rotation:
$a_D^{25} = -39.5$ (c = 0.17; CHCl₃/MeOH: 8/2:v/v).

The compound of Example 107a is the enantiomer of that of Example 106a.

The compound of Example 108b was prepared from the compound of Example 28a by reacting with hydroxylamine hydrochloride in DMF and by activating with the reagent BOP in the presence of DIPEA.

Some compounds according to the invention, described in Table 4A above, are useful for the preparation of other compounds. Thus, the compound of Example 99a makes it possible to obtain the compound of Example 101a, then that of Example 103aand finally that of Example 104a.

EXAMPLE 109a 2-((2S,4S)-4-Azido-2-(methoxycarbonyl)pyr-rolidinocarbonyl)-5-chloro-3-(2-chlorophenyl)-1-(3,4-dimethoxyphenylsulfonyl)-3-hydroxyindoline, cis isomer

A)

2',5-Dichloro-2-[N-(3,4-dimethoxyphenylsulfonyl)-N-((2S,4R)-4-hydroxy-2-(methoxycarbonyl)pyr-rolidinocarbonylmethyl)]amino-benzophenone 15 g of the acid prepared in Example 10a–11a, Step A) and 6.25 g of methyl (2S,4R)-4-hydroxyprolinate hydrochloride are heated to 0° C. in 150 ml of DCM in the presence of 7.4 g of DIPEA. A solution of 12.7 g of BOP in 30 ml of DCM is added dropwise over 30 minutes and the amount of DIPEA necessary to neutralize the solution is added. After one night at RT, the mixture is extracted in the-usual way and chromatographed on silica by elution with a DCM/AcOEt (60/40; v/v) mixture. The expected product crystallizes from a DCM/ether/isopropyl ether mixture.

M.p.=128°–131° C.

$\alpha_D$= +8.5 (c=0.38; chloroform).

B)

2',5-Dichloro-2-[N-(3,4-dimethoxyphenylsulfonyl)-N-((2S,4R)-4-mesyloxy-2-(methoxycarbonyl)pyr-rolidinocarbonylmethyl)]aminobenzophenone 2 g of the compound obtained in the preceding step are dissolved at 0° C. in 10 ml of DCM. 550 mg of triethylamine and then 550 mg of methanesulfonyl chloride are added and the mixture is left at 0° C. for 20 hours. Water is added and the organic layer is washed with 0.5N hydrochloric water, with water and then with a sodium bicarbonate solution, dried over magnesium sulfate and evaporated. The oil obtained is used as it is in the following step.

C)

2-[N-((2S,4S)-4-azido-2-(methoxycarbonyl)pyr-rolidinocarbonylmethyl)-N-(3,4-dimethoxyphenylsulfonyl)]amino-2',5-dichlorobenzophenone 11 g of the product prepared in the preceding step are heated in 60 ml of DMSO at 80°–90° C. in the presence of 2.7 g of sodium azide for 18 hours. The mixture is poured into water, extracted with ethyl acetate, the organic layer washed with water, dried and chromatographed on silica by eluting with a pentane/AcOEt (50/50; v/v) mixture. An oil (10 g) is obtained.

$\alpha_D$= −25.5 (c=0.39; chloroform, T=26° C.).

D)

2-((2S,4S)-4-Azido-2-(methoxycarbonyl)pyr-rolidinocarbonyl)-5-chloro-3-(2-chlorophenyl)-1-(3,4-dimethoxyphenylsulfonyl)-3-hydroxyindoline, cis isomer 3.38 g of the product obtained in the preceding step are cyclized under the usual conditions in the presence of DBU. The expected product is obtained which is recrystallized from DCM/isopropyl ether.

m=755 mg.

M.p. 200°–202° C.

$\alpha_D$= −176 (c=0.21; chloroform, T=26° C.).

EXAMPLE 110a

2-[(2S,4S)-4-(N-Benzyloxycarbonyl-N-methyl)amino-2-(methoxycarbonyl)pyrrolidinocarbonyl]-5-chloro-3-(2-chlorophenyl)-1-(3,4-dimethoxyphenylsulfonyl)-3-hydroxyindoline, cis isomer A) Methyl ester of (N-Boc)-4-hydroxyproline The starting material is the hydrochloride of the methyl ester of (2S,4R)-4-hydroxyproline.

19 g of this compound are suspended in 100 ml of THF, 22.9 g of (Boc)$_2$O are added and then the mixture is cooled to 0° C. 21.2 g of triethylamine in 25 ml of THF are added dropwise and then the mixture is stirred for 12 hours at 0° C. and 4 hours at 60° C. Water is added, the mixture is extracted with ethyl acetate, the organic layer is washed with water, with a potassium hydrogensulfate solution (4 times), with water and then with saline water. The solvent is evaporated and an oil (21.6 g) is isolated which contains a small amount of (Boc)$_2$O.

B) Methyl ester of (2S,4R)-(N-Boc)-4-mesyloxyproline

A solution of 22.9 g of the product prepared in the preceding step in 250 ml of DCM is cooled to 0° C. 22.9 g of mesyl chloride in 10 ml of DCM are added dropwise, then 9.4 g of triethylamine in 100 ml of DCM are added dropwise and the mixture is left to return to RT overnight. The mixture is evaporated to dryness, water is added, the mixture is extracted with AcOEt, the organic layer is washed with water and saline water and dried over magnesium sulfate. After a second evaporation, an oil is obtained which is used as it is in the following step.

C) Methyl ester of (2S,4S)-(N-Boc)-4-azidoproline

This compound is prepared from that obtained in Step B. 15.2 g of the methyl ester of (N-Boc)-4-mesyloxy-2-hydroxyproline are dissolved in 70 ml of DMSO and the solution is heated at 90° C. for 5 hours in the presence of 3.05 g of sodium azide. The mixture is cooled, water is added, the mixture is extracted with AcOEt, the organic layer is washed with water and saline water and dried over MgSO$_4$. The oil obtained is purified by chromatography on silica by eluting with the AcOEt/hexane (40/60; v/v) mixture.

$\alpha_D$= −37.8 (c=3; chloroform).

lit. $\alpha_D$= −36.6 (c=2.8; chloroform) D. J. Abrahamer et al., J. Med. Chem., 1983, 549, 26.

D) Methyl ester of (2S,4S)-(N-Boc)-4-aminoproline 8.45 g of the compound obtained in Step A are dissolved in 100 ml of methanol, 500 mg of 10% Pd/C are added and the mixture is hydrogenated at 40° C. for 18 hours. The catalyst is filtered off, half the methanol is evaporated, 100 ml of 0.5N HCl are added, the remainder of the methanol is then evaporated and the unreacted starting material is extracted with AcOEt. The aqueous phase is treated with sodium carbonate and the fraction containing the expected product (m=4.35 g) is extracted with AcOEt.

E) Methyl ester of (2S,4S)-(N-Boc)-4-(N'-benzyloxycarbonylamino)proline

The crude product obtained in the preceding step is dissolved in 15 ml of ether and 15 ml of DCM at 0° C. 2.3 g of DIPEA and then 3.03 g of benzyl chloroformate in 5 ml of DCM are added, over 70 minutes at 0° C. After 3 hours, the solvents are evaporated at RT under vacuum; water and ethyl acetate are added and the organic phase is washed successively with a potassium hydrogensulfate solution (3 times), with water (3 times), with a sodium carbonate solution (3 times), with water (3 times) and with saline water. The product is chromatographed on silica by eluting with hexane/AcOEt (40/60; v/v) mixture in order to obtain the expected product.

$\alpha_D = -16.4$ (c=0.3; chloroform).

F) Methyl ester of (2S,4S)-(N-Boc)-4-(N'-benzyloxycarbonyl-N'-methyl-)aminoproline 2 g of the compound obtained in the preceding step are dissolved in 20 ml of DMF at 0° C., under argon, in the presence of 2.25 g of methyl iodide. 170 mg of 80% sodium hydride are added in portions and then the mixture is stirred at 0° C. for 90 minutes. The mixture is extracted with water and ethyl acetate; the organic phase is washed with water and then saline water. The product is chromatographed on silica by eluting with a hexane/AcOEt (50/50; v/v) mixture. 1.55 g of the expected product is obtained.

$\alpha_D = -38.8$ (c=0.38; chloroform).

G) 2',5-Dichloro-2-[(2S,4S)-N-(3,4-dimethoxyphenylsulfonyl)-N-(4-(N'-benzyloxycarbonyl-N'-methyl)amino-2(methoxycarbonyl)pyrrolidinocarbonylmethyl)]-aminobenzophenone This product is obtained by the usual methods.
$\alpha_D = -22.4$ (c=0.37; chloroform).

H) 2-[(2S,4S)-4-(N-Benzyloxycarbonyl-N-methyl)amino-2-(methoxycarbonyl)pyrrolidinocarbonyl]-5-chloro-3-(2-chlorophenyl)-1-(3,4-dimethoxyphenylsulfonyl)-3-hydroxyindoline, cis isomer This product is obtained by cyclizing in the presence of DBU according to the usual methods. The crystals formed are crystallized from DCM/isopropyl ether.
M.p.=129° C.
$\alpha_D = -129$ (c=0.321; chloroform).
The isomeric purity by HPLC is 99%.

The compounds prepared in Examples 109a and 110a are used to prepare the compounds according to the invention 20 described in Table 5A below:

TABLE 5A

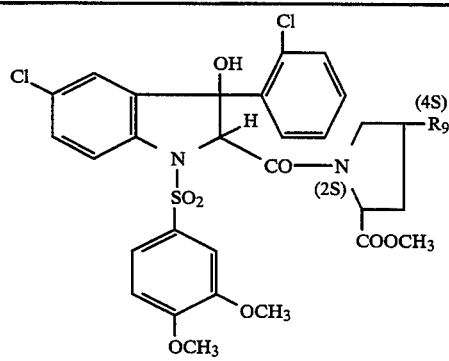

| Example | R9 | $\alpha_D$(chloroform) |
|---|---|---|
| 111a cis | —NH2 | −189.6 c = 0.4 |

TABLE 5A-continued

| Example | R9 | $\alpha_D$(chloroform) |
|---|---|---|
| 112a cis | —NHCOOCH2—C6H5 | −174 c = 0.24 |
| 113a cis | —NHCH3 | −152.6 c = 0.28 |
| 114a cis | —N(CH3)2 | −191 c = 0.19 |

The compound of Example 112a makes it possible to successively prepare the compounds of Examples 115a and 116a described in Table 6A below and the compound of Example 114a makes it possible to prepare the compound of Example 116b.

TABLE 6A

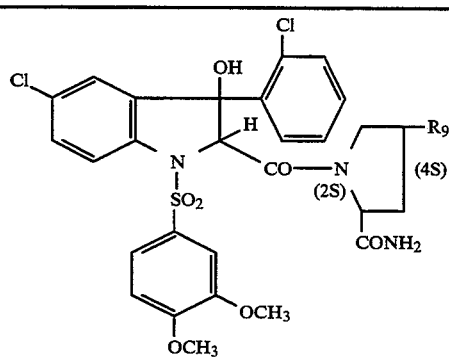

| Example | R9 | $\alpha_D$(chloroform) |
|---|---|---|
| 115a cis | —NHCOOCH2—C6H5 | −151 c = 0.27 |
| 116a cis | —NH2 | −161.4 c = 0.26 |
| 116b cis | —N(CH3)2 | |

The compound of Example 116b can be prepared either by conversion of the compound of Example 114a, or from (2S,4S)-(N-Boc)-4-(dimethylamino)prolinamide, the preparation of which is carried out as follows:

1) Methyl (2S,4S)-(N-Boc)-4-aminoprolinate is prepared from methyl (2S,4S)-4-azidoprolinate according to T. R. Webl in J. Org. Chem., 1991, 56, 3009.

2) Methyl (2S,4S)-(N-Boc)-4-(dimethylamino)prolinate.

4 g of the compound prepared in 1) are dissolved in 50 ml of acetonitrile, 12.8 ml of 30% formalin are added and then, over 5 minutes, 3 g of sodium cyanoborohydride. After the reactants have been in contact for 2 hours, acetic acid is added to bring the solution to a pH of 6. After 3 hours, the acetonitrile is evaporated, water, potassium carbonate and solid sodium chloride are added and the mixture is extracted with 4 volumes of ethyl acetate. The organic phase is evaporated, the residue is dissolved in 1N hydrochloric acid and extraction is carried out with AcOEt. Solid sodium carbonate and then solid sodium chloride are added to the aqueous phase and extraction is carried out with AcOEt. After evaporating, the residue is chromatographed on silica gel by eluting with a DCM/MeOH (95/5; v/v) mixture and an oil which solidifies is isolated.

m=2.1 g.

IR (DCM): 1755 cm$^{-1}$, 1695 cm$^{-1}$.

3) 534 mg of the ester prepared in 2) are dissolved in 4 ml of MeOH and are treated with sodium hydroxide (116 rag) in 1 ml of water for 48 hours at RT. The mixture is acidified with 0.5N hydrochloric acid to a pH of 3.5 and is evaporated to dryness. An azeotropic drying of the residue is carried out in the presence of benzene (5 times) and then the residue is dried under vacuum for 8 hours. 2 ml of DMF and 3 ml of DCM are then added and the mixture is cooled to 0° C. 865 mg of BOP, and DIPEA, are added to bring the reaction mixture to neutrality. After 15 minutes, a stream of gaseous ammonia is bubbled through 2 times for 30 minutes. After 2 hours at RT, the DCM is evaporated, carbonated water and sodium chloride are added and the mixture is extracted with 4 volumes of AcOEt. After evaporating, the residue is chromatographed on silica. The mixture (DCM/MeOH/NH$_4$OH; 84.5/15/0.5; v/v/v) elutes a solid (m=185 mg) which is recrystallized from a DCM/isopropyl ether mixture.

M.p.=183°-186° C.

$\alpha_D^{25}$= −63.1 (c=0.24; chloroform).

EXAMPLE 117a

Decarboxylation of N-(2-carboxyethyl)-N-ethyl-3-(2-chlorophenyl)-5-chloro-1-(3,4-dimethoxyphenylsulfonyl)-3-hydroxy-2-indolinecarboxamide, cis isomerism 630 mg of the compound prepared in Example 41a are placed in solution in 20 ml of THF under an argon atmosphere and then 101 mg of N-methylmorpholine at −15° C. and 118 mg of isobutyl chloroformate are added. After stirring for 5 minutes, 127 mg of N-hydroxy-2-pyridinethione and 101 mg of TFA are added, the mixture is held at −15° C. with stirring for 15 minutes, 900 mg of tert-butylmercaptan are then added and the mixture is left to return to RT. The reaction mixture is then irradiated for 1 hour 30 with a tungsten filament lamp (150 watts). The mixture is concentrated, taken up in water, extracted with DCM and the extract dried and concentrated. The residue is chromatographed on silica by eluting with DCM/AcOEt (95 / 5; v/v) . The expected product is obtained.

m=300 mg.

M.p.=215° C.

This compound is similar to that of Example 125 described in the European Patent Application EP 469984. It has the cis configuration around the 2,3 bond of the indoline as in the starting material.

EXAMPLE 118a

Decarboxylation of 2-((2R)-2-(carboxymethyl)pyrrolidinocarbonyl)-5-chloro-3-(2-chlorophenyl)-1-(3,4-dimethoxyphenylsulfonyl)-3-hydroxyindoline, cis isomer The operation is carried out as in the preceding example from the compound described in Example 102a.

The product obtained is recrystallized from a DCM/isopropyl ether mixture.

M.p.=215°-220° C.

$\alpha_D$= −214.5° (c=0.2; chloroform).

This compound is 2-((2S)-2-methylpyrrolidinocarbonyl)-5-chloro-3-(2-chlorophenyl)-1-(3,4-dimethoxyphenylsulfonyl)-3-hydroxyindoline, cis isomerism.

EXAMPLE 119a

Decarboxylation of 2-(2-carboxypyrrolidinocarbonyl)-5-chloro-3-(2-chlorophenyl)-1-(3,4-dimethoxyphenylsulfonyl)-3-hydroxyindoline, cis isomer The operation is carried out as in the preceding example by using the compound prepared in Example 28a as the starting material. The product obtained is recrystallized from an isopropyl ether/DCM mixture.

M.p.=263° C.

$\alpha_D$= −201.5° (c=0.2; chloroform).

This compound is 2-pyrrolidinocarbonyl-5-chloro-3-(2-chlorophenyl)-1-(3,4-dimethoxyphenylsulfonyl)-3-hydroxyindoline, cis isomer.

What is claimed is:

1. A compound of formula:

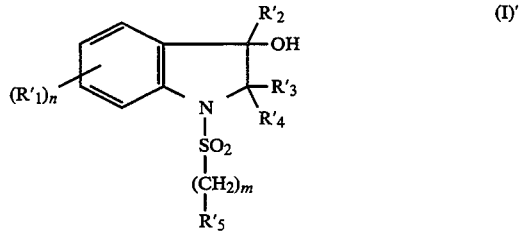

in which

R'$_1$ is a halogen atom, a C$_1$-C$_4$ alkyl, a hydroxyl, a C$_1$-C$_4$ alkoxy, a benzyloxy group, a cyano group, a trifluoromethyl group, nitro group or an amino group;

R'$_2$ is a C$_1$-C$_6$ alkyl, a C$_5$-C$_7$ cycloalkyl, a C$_5$-C$_7$ cycloalkene or a phenyl which is unsubstituted or monosubstituted or polysubstituted by a C$_1$-C$_4$ alkyl, a C$_1$-C$_4$ alkoxy, a halogen, a trifluoromethyl group or an amino group, or R'$_2$ is a nitrophenyl which is unsubstituted or monosubstituted by a trifluoromethyl group or monosubstituted or polysubstituted by a C$_1$-C$_4$ alkyl or a halogen;

R'$_3$ is a hydrogen atom;

R'$_4$ is a carbamoyl group of formula CONR'$_6$R'$_7$;

R'$_5$ is a C$_1$-C$_4$ alkyl; a 1-naphthyl; a 2-naphthyl; a 5-dimethylamino-1-naphthyl; a phenyl which is unsubstituted or substituted by one or more substituents selected from a halogen atom, a C$_1$-C$_4$ alkyl, a trifluoromethyl group, an amino group which is free or substituted by one or two C$_1$-C$_4$ alkyls, a hydroxyl, a C$_1$-C$_4$ alkoxy, a C$_2$-C$_4$ alkenoxy, a C$_1$-C$_4$ alkylthio, a trifluoromethoxy group, a benzyloxy group, a cyano group, a carboxyl group, a $C_1$–$C_4$ alkoxy carbonyl group, a carbamoyl group which is free or substituted by one or two $C_1$–$C_4$ alkyls or a $C_1$–$C_4$ alkylamino group, or $R'_5$ is a nitrophenyl which is unsubstituted or monosubstituted by a trifluoromethyl group or a $C_2$–$C_4$ alkenoxy or mono- or poly-substituted by a halogen, a $C_1$–$C_4$ alkyl, a $C_1$–$C_4$ alkoxy, a $C_1$–$C_4$ alkylthio, a trifluoromethoxy group or a benzyloxy group;

$R'_6$ is a $C_1$–$C_6$ alkyl or $R'_6$ is the same as $R'_7$;

$R'_7$ is a 4-piperidyl group or a 3-azetidinyl group, the said groups being substituted or unsubstituted on the nitrogen by a $C_1$–$C_4$ alkyl, by a benzyloxycarbonyl or by a $C_1$–$C_4$ alkoxycarbonyl; a group $(CH_2)_r$ which is itself substituted by a 2-, 3- or 4-pyridyl group, by a hydroxyl group or by an amino group which is free or substituted by one or two $C_1$–$C_4$ alkyls, a carboxyl group, a $C_1$–$C_4$ alkoxycarbonyl group, a benzyloxycarbonyl group or a carbamoyl group which is free or substituted by one or two $C_1$–$C_4$ alkyls;

or $R'_6$ and $R'_7$ together, with the nitrogen atom to which they are connected, form a heterocycle selected from the group consisting of:

morpholine;
thiomorpholine;
thiazolidine or 2,2-dimethylthiazolidine, unsubstituted or substituted by $R_8$;
piperazine, unsubstituted or substituted at the 4-position by a group $R''_8$; and
an unsaturated, 5-membered ring containing a single nitrogen atom and substituted by $R_8$ or a saturated, 3-, 4-, 6- or 7-membered ring containing a single nitrogen atom and substituted by $R_5$ and $R_9$;

$R_8$ is $R'_8$ or a group $(CH_2)_s$ which is itself substituted by a hydroxyl or by an amino which is free or substituted by one or two $C_1$–$C_4$ alkyls;

$R'_8$ is a group $(CH2)_q$ which is itself substituted by a carboxyl group, a $C_1$–$C_4$ alkoxycarbonyl group, a benzyloxycarbonyl group, a carbamoyl group which is free or substituted by a hydroxyl or by one or two $C_1$–$C_4$ alkyls or an aminocarbothioyl group which is free or substituted by one or two $C_1$–$C_4$ alkyls;

$R''_8$ is $R'_8$ or a group $(CH_2)_2NH_2$ which is free or substituted by one or two $C_1$–$C_4$ alkyls;

$R_9$ is hydrogen, a halogen, a group $(CH_2)_rOR_{10}$, a group $(CH_2)_rNR_{11}R_{12}$, a group $(CH_2)_5CONR_{11}R'_{11}$ or an azido group;

$R_{10}$ is hydrogen, a $C_1$–$C_4$ alkyl, a mesyl or a tosyl;

$R_{11}$, $R'_{11}$ and $R_{12}$ are each a hydrogen or a $C_1$–$C_4$ alkyl or $R_{11}$ is hydrogen and $R_{12}$ is a benzyloxycarbonyl or a $C_1$–$C_4$ alkoxycarbonyl;

n is 0, 1 or 2;

m is 0, 1 or 2;

q is 0, 1, 2 or 3;

r is 0, 1, 2 or 3, with the limitation that r is not zero when $R_5$ or $R_9$ is at the alphaposition of the intracyclic amide nitrogen;

s is 0 or 1;

as well as its possible salts.

2. A compound as claimed in claim 1 in $R'_4$ is $CONR'_6R'_7$ and $NR'_6R'_7$ is a piperidino group substituted at the 4-position by an amino group, a $C_1$–$C_4$ alkylamino or a $C_1$–$C_4$ dialkylamino.

3. A compound as claimed in claim 1 in which $R'_4$ is $CONR_6R'_7$ and $NR_6'R_7$ is a thiazolidino group substituted by a group $(CH_2)_q$ which is itself substituted by a carboxyl group or a carbamoyl group with q=0, 1,2 or 3.

4. A compound as claimed in claim 1 in which $R'_4$ is $CONR_6'R_7'$, $R'_6$ being a $C_1$–$C_4$ alkyl and $R_7'$ being a group $(CH_2)_r$ which is itself substituted by a carboxyl group or a carbamoyl group with r=1, 2 or 3.

* * * * *